US011287396B2

(12) United States Patent
Guzman

(10) Patent No.: US 11,287,396 B2
(45) Date of Patent: Mar. 29, 2022

(54) METHOD AND SYSTEM FOR SIMULTANEOUS DETERMINATION OF MULTIPLE MEASURABLE BIOMARKERS DURING THE DEVELOPMENT OF A COMMUNICABLE DISEASE

(71) Applicant: PRINCETON BIOCHEMICALS, INC, Princeton, NJ (US)

(72) Inventor: Norberto A. Guzman, Princeton, NJ (US)

(73) Assignee: PRINCETON BIOCHEMICALS, INC., Princeton, NJ (US)

( * ) Notice: Subject to any disclaimer, the term of this patent is extended or adjusted under 35 U.S.C. 154(b) by 0 days.

(21) Appl. No.: 16/894,316

(22) Filed: Jun. 5, 2020

(65) Prior Publication Data

US 2021/0382003 A1 Dec. 9, 2021

(51) Int. Cl.
*G01N 27/447* (2006.01)
*G01N 33/561* (2006.01)
(Continued)

(52) U.S. Cl.
CPC ....... *G01N 27/44756* (2013.01); *G01N 1/405* (2013.01); *G01N 27/44708* (2013.01);
(Continued)

(58) Field of Classification Search
CPC ........... G01N 27/44743; G01N 33/543; G01N 1/405; G01N 33/53; G01N 33/5302; G01N 27/44708; G01N 27/44756; G01N 33/54313; G01N 33/54353; G01N 33/561; G01N 2001/4038; G01N 2030/326; G01N 30/466; G01N 30/74; G01N 27/44726; G01N 27/44773; G01N 1/40; G01N 27/44704; G01N 33/54326;
(Continued)

(56) References Cited

U.S. PATENT DOCUMENTS 3,777,014 A 12/1973 Zichis
5,045,172 A 9/1991 Guzman
(Continued)

FOREIGN PATENT DOCUMENTS

EP 2898067 B1 1/2020
WO 2003049595 A2 6/2003
(Continued)

OTHER PUBLICATIONS

K. Watkins. Current Emergency and Hospital Medicine Reports vol. 6, pp. 86-93, 2018.
(Continued)

*Primary Examiner* — Dean Kwak
(74) *Attorney, Agent, or Firm* — Porzio Bromberg & Newman P.C.

(57) ABSTRACT

A diagnostic and prognostic method and system for sequentially analyzing in a biological fluid or tissue extract the presence of an antigenic infectious agent, infectious organism or its toxic product; an antibody response to the antigenic infectious agent, infectious organism or its toxic product; one or more biomarkers formed during infection in response to a communicable disease; and one or more biomarkers to assess the severity of the disease and to monitor the effectiveness of drug therapy or vaccination.

21 Claims, 8 Drawing Sheets

(51) Int. Cl.
*G01N 33/543* (2006.01)
*G01N 1/40* (2006.01)

(52) U.S. Cl.
CPC ..... *G01N 27/44743* (2013.01); *G01N 33/543* (2013.01); *G01N 33/561* (2013.01)

(58) Field of Classification Search
CPC ........... B01L 2200/027; B01L 2200/10; B01L 9/527; B01L 3/502715; B01L 2300/0636; B01L 2300/0663; B01L 2300/0816; B01L 2300/0861; B01L 2200/0668; B01L 2300/0627
See application file for complete search history.

(56) References Cited

U.S. PATENT DOCUMENTS

| | | | |
|---|---|---|---|
| 5,106,365 | A | 4/1992 | Hernandez |
| 5,295,979 | A | 3/1994 | Delaurentis et al. |
| 5,441,481 | A | 8/1995 | Mishra et al. |
| 7,220,852 | B1 | 5/2007 | Rota et al. |
| 7,329,388 | B2 | 2/2008 | Guzman |
| 7,850,677 | B2 | 12/2010 | Blake et al. |
| 8,465,941 | B2 | 6/2013 | Bergmann et al. |
| 8,663,927 | B2 | 3/2014 | Daunert et al. |
| 8,865,075 | B2 | 10/2014 | Guzman |
| 8,962,260 | B2 | 2/2015 | Sambursky et al. |
| 9,146,234 | B2 | 9/2015 | Guzman |
| 9,657,360 | B2 | 5/2017 | Stewart et al. |
| 9,696,299 | B2 | 7/2017 | Guzman |
| 9,759,720 | B2 | 9/2017 | Bjorck et al. |
| 10,408,789 | B2 | 9/2019 | Guzman |
| 10,517,538 | B2 * | 12/2019 | Burnett ................ A61B 5/1459 |
| 2003/0236454 | A1 | 12/2003 | Liska et al. |
| 2005/0119588 | A1 | 6/2005 | Model et al. |
| 2005/0155861 | A1 * | 7/2005 | Guzman .......... G01N 27/44743 204/451 |
| 2007/0248949 | A1 | 10/2007 | Inoue et al. |
| 2010/0311758 | A1 | 12/2010 | Roth et al. |
| 2011/0020459 | A1 * | 1/2011 | Achrol ................ A61K 35/12 424/520 |
| 2011/0111970 | A1 | 5/2011 | Tzean et al. |
| 2016/0287728 | A1 | 10/2016 | Norenberg |
| 2017/0303822 | A1 | 10/2017 | Allworth et al. |
| 2018/0280972 | A1 | 10/2018 | Guzman et al. |

FOREIGN PATENT DOCUMENTS

| | | |
|---|---|---|
| WO | 2005016132 A2 | 2/2005 |
| WO | 2015035260 | 3/2015 |

OTHER PUBLICATIONS

Asymptomatic carriers of COVID-19 disease infecting people in Iceland: https://www.cnn.com/2020/04/01/europe/iceland-testing-coronavirus-intl/index.html, published online on Apr. 3, 2020.
It's estimated 1 in 4 coronavirus carriers could be asymptomatic. Here's what we know: https://www.sciencealert.com/here-s-what-we-know-so-far-about-those-who-can-pass-corona-without-symptoms; published online on Apr. 3, 2020.
C. Rothe et al.—16 more authors. New England Journal of Medicine, vol. 382, pp. 970-971, 2020.
K.G. Andersen, A. Rambaut, W.I. Lipkin, E.C. Holmes, R.F. Garry. Nature Medicine. https://doi.org/10.1038/s41591-020-0820-9, published online on Mar. 17, 2020.
T. Singhal. The Indian Journal of Pediatrics, vol. 87, pp. 281-286, 2020.
R.L. Hodinka, L. Kaiser. Journal of Clinical Microbiology, vol. 51, pp. 2-8, 2013.
CDC Laboratory Testing for Middle East Respiratory Syndrome Coronavirus (MERS-CoV): https://www.cdc.gov/coronavirus/mers/lab/lab-testing.html.
R.M. Lequin, Clinical Chemistry vol. 51, pp. 2415-2418, 2005.
J. Gibbs, M. Vessels, M. Rothenberg. Application Note. https://www.corning.com/catalog/cls/documents/application-notes/CLS-DD-AN-458.pdf.
N.A. Guzman, D.E. Guzman. Journal of Chromatography B, vol. 1021, pp. 14-29, 2016.
K. Terato, C.T. Do, D. Cutler, T. Waritani, H. Shionoya. Journal of Immunological Methods, vol. 407, pp. 15-25, 2014.
A.L. Notkins. Trends in Immunology, vol. 25, pp. 174-179, 2004.
J. Tate, G. Ward. Clinical Biochemical Reviews, vol. 25, pp. 105-120, 2004.
I. Jovcevska, S. Muyldermans. BioDrugs, vol. 34, pp. 11-26, 2020.
S.M. Nimjee, R.R. White, R.C. Becker, B.A. Sullenberg. Annual Review of Pharmacology and Toxicology, vol. 57, pp. 61-79, 2017.
J. Hirabayashi, R. Arai. Interface Focus, vol. 9, doi.10.1098/rsfs.2018.0068, 2019.
T. Goda, D. Higashi, A. Matsumoto, T. Hoshi, T. Sawaguchi, Y. Miyahara. Biosensors and Bioelectronics, vol. 73, pp. 174-180, 2015.
T.M. Phillips, E. Wellner. Electrophoresis, vol. 34, pp. 1530-1538, 2013.
M. Müller. British Medical Journal, vol. 324, pp. 588-591, 2002.
S. Klaus, M. Heringlake, L. Bahlmann. Critical Care, vol. 8, pp. 363-368, 2004.
V.I. Chefer, A.C. Thompson, A. Zapata, T.S. Shippenberg. Current Protocols in Neuroscience, Chapter: Unit7.1, doi:10.1002/0471142301.ns0701s47, 2009.
K.J. Hersini, L. Melgaard, P. Gazerani, L.J. Petersen. Acta Dermatologica Venereologica, vol. 94, pp. 501-511, 2014.
D. Vandamme, W. Fitzmaurice, B. Kholodenko, W. Kolch. QJM International Journal of Medicine, vol. 106, pp. 891-895, 2013.
M. Gregus, F. Foret, P. Kuban. Electrophoresis, vol. 36, pp. 526-533, 2014.
M. van der Schee, H. Pinheiro, E. Gaude. Ecancermedicalscience, vol. 12: ed84; doi: 10.3332/ecancer.2018.ed84, 2018.
B. Abderrahman. Future Oncology, vol. 15, pp. 1679-1682, 2019.
P. Fabian, J. Brain, E.A. Houseman, J. Gern, D.K. Milton. Journal of Aerosol Medicine and Pulmonary Drug Delivery, vol. 24, pp. 137-147, 2011.
O. Lawal, W.M. Ahmed, T.M.E Nijsen, R. Goodacre, S.J. Fowler. Metabolomics, vol. 13, 110; doi: 10.1007/s11306-017-1241-8, 2017.
S. Das, M. Pal. Journal of The Electrochemical Society, vol. 167, 037562; doi:10.1149/1945-7111/ab67a6, 2020.
W. Miekisch, J.K. Schubert, G.F.E. Noeldge-Schomburg. Clinica Chimica Acta, vol. 347, pp. 25-39, 2004.
S.P. Humphrey, R.T. Williamson. The Journal of Prosthetic Dentistry, vol. 85, pp. 162-169, 2001.
M. Singh, U. Singhal, G.K. Bhasin, R. Panday, S.K. Aggarwal. Journal of Pharmaceutical and Biomedical Sciences, vol. 37, pp. 1932-1941, 2013.
S. Aliberti, L.C. Morlacchi, P. Faverio, R. Fernandez-Botran, R. Cosentini, M. Mantero, P. Peyrani, J. Ramirez, J. Bordon, F. Blasi. Pneumonia, vol. 8; doi: 10.1186/s41479-016-0009-7, 2016.
J.M. Betz, P.N. Brown, M.C. Roman. Filoterapia, vol. 82, pp. 44-52, 2011.
E.C. de Oliveira, E.I. Muller, F. Abad, J. Dallarosa, C. Adriano. Quimica Nova, vol. 33, pp. 984-987, 2010.
H. Chen, K. Liu, Z. Li, P. Wang. Clinica Chimica Acta, vol. 493, 138-147, 2019.
P. Mehta, D.F. McAuley, M. Brown, E. Sanchez, R.S. Tattersall, J.J. Manson. Lancet; https://doi.org/10.1016/S0140-6736(20)30628-0, 2020.
J.M. Street, E.H. Koritzinsky, D.M. Glispie, R.A. Star, P.S. Yuen. Advances in Clinical Chemistry, vol. 78, pp. 103-122, 2017.
D. Demonchy, C. Cias, E. Fontas, E. Berard, J. Breaud, P.S. Rohrlich, F. Dubos, C. Fortier, J. Desmontils, A.L. Herisse, D. Donzeau, H. Haas, A. Tran. Trials, vol. 20, 783; https://doi.org/10.1186/s13063-019-3914-2, 2019.
L.E. Nicolle. Antimicrobial Resistance and Infection Control, vol. 3, 23; doi.10.1186/2047-2994-3-23, 2014.
A.A.H. Gadalla, I.M. Friberg, A. Kift-Morgan, J. Zhang, M. Eberl, N. Topley, I. Weeks, S. Cuff, M. Wooton, M. Gal, G. Parekh, P.

(56) References Cited

OTHER PUBLICATIONS

Davis, C. Gregory, K. Hood, K. Hughes, C. Butler, N.A. Francis. Scientific Reports (Nature), vol. 9, 19694; https://doi.org/10.1038/s41598-019-55523-x, 2019.
J-C. Lagier, S. Edouard, I. Pagnier, O. Mediannikov, M. Drancourt, D. Raoult. Clinical Microbiology Reviews, vol. 28, pp. 208-236, 2015.
R.C.L. Feneley, I.B. Hopley, P.N.T. Wells. Journal of Medical Engineering & Technology, vol. 39, pp. 459-470, 2015.
D.J. Stickler. Journal of Internal Medicine, vol. 276, pp. 120-129, 2014.
L. Liu, L. Chen, N. Zhao, C. Yuan, Y. Cao, M. Chen. Medicine, vol. 97, p. 35-e12030, 2018.
O.L. Tavano, A. Berenguer-Murcia, F. Secundo, R. Fernandez-Lafuente. Comprehensive Reviews in Food Science and Food Safety, vol. 17, pp. 412-436, 2018.
R.J. Martinez, J.H. Shaper, N.P. Lundh, P.D. Bernard, A.N. Glazer. Journal of Bacteriology, vol. 109, pp. 1239-1246, 1972.
S.M. Lemon, E. Amphlett, D. Sangar. Journal of Virology, vol. 65, pp. 5636-5640, 1991.
F. Roux-Dalvai, C. Gotti, M. Leclercq, M-C. Helie, M. Boissinot, T.N. Arrey, C. Dauly, F. Fournier, I. Kelly, J. Marcoux, J. Bestman-Smith, M.G. Bergeron, A. Droit. Molecular & Cellular Proteomics, vol. 18, pp. 2492-2505, 2019.
J. Lin, J. Li, B. Huang, J. Liu, X. Chen, X-M. Chen, Y-M. Xu, L-F. Huang, X-Z. Wang. The Scientific World Journal, vol. 2015, http://dx.doi.org/10.1155/2015/657086, 2015.
D.L. Sampson, B.A. Fox, T.D. Yager, S. Bhide, S. Cermelli, L.C. McHugh, T.A. Seldon, R.A. Brandon, E. Sullivan, J.J. Zimmerman, M. Noursadeghi, R.B. Brandon. Scientific Reports—Nature, vol. 7, 2914, doi:10.1038/s41598-017-02325-8, 2017.
M.J. Binnicker. Clinical Chemistry, 0:0, 1-3; doi:10.1093/clinchem/hvaa071, 2020.
M. Ye, D.T. Rossi, C.E. Lunte, Journal of Pharmaceutical and Biomedical Analysis, vol. 24, pp. 273-280, 2000.
A. Zapata, V.I. Chefer, T.S. Shippenberg. Current Protocols in Neuroscience, chapter—unit7.2, doi.10.1002/0471142301.ns0702s47, 2009.
X. Kou, G. Chen, S. Huang, Y. Ye, G. Ouyang, J. Gan, F. Zhu. Journal of Agricultural and Food Chemistry, vol. 67, pp. 2120-2126, 2019.
L. Carteron, P., P. Bouzat, M. Oddo. Frontiers in Neurology, vol. 8, 601; doi.10.3389/fneur.2017.00601, 2017.
J.E. van der Mast, M.W. Nijsten, J.C. Alffenaar, D.J. Touw, W. Bult. Pharmacology Research and Perspectives, vol. 7, e00483, doi:10.1002/prp2.483.eCollection, 2019.
J-Z. Pan, P. Fang, X-X Fang, T-T. Hu, J. Fang, Q. Fang. Scientific Reports (Nature), vol. 8:1791; doi:10.1038/s41598-018-20058-0, 2018.
N. Mavrogiannis, M. Ibo, X. Fu, F. Crivellary, Z. Gagnon. Biomicrofluidics, vol. 10, 034107; doi:10.1063/1.4950753, 2016.
L. Ashkenazi-Hoffnung, K. Oved, R. Navon, T. Friedman, O. Boico, M. Paz, G. Kronenfeld, L. Etshtein, A. Cohen, T.M. Gottlieb, E. Eden, I. Chistyakov, I. Srugo, A. Klein, S. Ashkenazi, O. Scheuerman. The European Journal of Clinical Microbiology and Infectious Diseases, vol. 37, pp. 1361-1371, 2018.
S-T. Yu, C.T. Bui, D.T.H. Kim, A.V.T. Nguyen, T.T.T. Trinh, S-J. Yeo, Scientific Reports (Nature), vol. 8, 13468, doi:10.1038/s41598-018-31786-8, 2018.
X. Jia, P. Zhang, Y. Tian, J. Wang, H. Zeng, J. Wang, J. Liu, Z. Chen, L. Zhang, H. He, K. He, Y. Liu. medRxiv (preprint), doi: https://doi.org/10.1101/2020.02.28.20029025, 2020.
A. Tahamtan, A. Ardebili. Expert Review of Molecular Diagnostics, vol. 2020, pp. 1-2, 2020.
C.P. West, V.M. Montori, P. Sampathkumar. Mayo Clinic Proceedings, https//doi.org/10.1016/j.mayocp.2020.04.004, 2020.

Z.Z. Rashid, S.N. Othman, M.N. Abdul Samat, U.K. Ali, K.K. Wong. Malaysian Journal of Pathology, vol. 42, pp. 13-21, 2020.
AdvaMedDx, https://dx.advamed.org/sites/dx.advamed.org/files/resource/advameddx-policy-primer-on-diagnostics-june-2011.pdf, 2011.
R.L.C. Voeten, I.K. Ventouri, R. Haselberg, G.W. Somsen. Analytical Chemistry, vol. 90, pp. 1464-1481, 2018.
J.S. Toraño, R. Ramautar, G. de Jong. Journal of Chromatography B, vol. 1118-1119, pp. 116, 136, 2019.
R.B. Yu, J.P. Quirino. Molecules, vol. 24, 1135, doi:10.3390/molecules24061135, 2019.
J.P. Shah, T.M. Phillips, J.V. Danoff, L.H. Gerber. Journal of Applied Physiology, vol. 99, pp. 1977-1984, 2005.
J. Dong, W. Ning, W. Liu, M.L. Bruening. Analyst, vol. 142, pp. 2578-2586, 2017.
Bailey, W.J., Ulrich, R. Expert Opinion in Drug Safety 2004, vol. 3, pp. 137-151.
Pham, H., Pham, D.H. Concurrency and Computation Practice and Experience 2019, https://doi.org/10.1002/cpe.5467 (2019).
Vazquez, Y., Gonzalez, L., Noguera, L., Gonzalez, P.A., Riedel, C.A., Bertrand, P., Bueno, S.M. Frontiers in Immunology 2019, vol. 10, 1154, doi:10.3389/fimmu.2019.01154.
Holub, M., Lawrence, D.A., Andersen, N., Davidova, A., Beran, O., Maresova, V., Chalupa, P. Mediators of Inflammation 2013, vol. 2013, 190145, http://dx.doi.org/10.1155/2013/190145.
Lam, C.W.K., Chan, M.H.M., Wong, C.K. The Clinical Biochemist Reviews 2004, vol. 25, pp. 121-1323.
Sun, X., Wang, T., Cai, D., Hu, Z., Chen, J., Liao, H., Zhi, L., Wei, H., Zhang, Z., Qiu, Y., Wang, J., Wang, A. Cytokine & Growth Factor Reviews 2020, https://doi.org/10.1016/j.cytogfr.2020.04.002.
George, P.M., Wells, A.U., Jenkins, R.G. The Lancet-Respiratory Medicine 2020, https://doi.org/10.1016/S2213-2600(20)30225-3.
Desogere, P., Tapias, L.F., Hariri, L.P., Rotile, N.J., Rietz, T.A., Probst, C.K., Blasi, F., Day, H., Mino-Kenudson, M., Weinreb, P., Violette, S.M., Fuchs, B.C., Tager, A.M., Lanuti, M., Caravan, P. Science Translational Medicine 2017, vol. 9, eaaf4696, doi:10.1126/scitranslmed.aaf4696.
Prockop, D.J., Kivirikko, K.I., Tuderman, L., Guzman, N.A. The New England Journal of Medicine 1979, vol. 301, pp. 13-23 and 77-85.
Schaade, L., Kleines, M., Hausler, M. Journal of Clinical Microbiology 2001, vol. 39, pp. 3902-3905.
Zhou, B., She, J., Wang, Y., Ma, X. Research Square 2020, doi:10.21203/rs.3.rs-18079/v1.
Lippi, G., Plebani, M. Clinica Chimica Acta 2020, vol. 505, pp. 190-191.
Hamblin, J. The Atlantic-Health Apr. 21, 2020.
Felsenstein, S., Herbert, J.A., McNamara, P.S., Hedrich, C.M. Clinical Immunology 2020, vol. 215, 108448, doi:10.1016/j.clim.2020.108448.
Holmberg—Interactions between surfactants and hydrolytic enzymes, Colloids and Surfaces B: Biointerfaces 168(2018)169-177.
Hedegus et al.—TiO2-Mediated Photocatalytic Mineralization of a Non-Ionic Detergent: Comparison and Combination with Other Advanced Oxidation Procedures.
Pan et al.—Exosomes in diagnosis and therapy of prostate cancer, Oncotarget, 2017, vol. 8, (No. 57), pp. 97693-97700.
Scavo et al.—Exosomes for Diagnosis and Therapy in Gastrointestinal Cancers Int. J. Mol . . . Sci. 2020, 2/, 367; doi:10.3390/ijrns21010367.
Akuma et al.—Naturally Occurring Exosome Vesicles as Potential Delivery Vehicle for Bioactive Compounds, Frontiers in Sustainable Food Systems, published: Apr. 16, 2019 doi: 10.3389/fsufs.2019.00023.
Kalluri et al.—The biology, function, and biomedical applications of exosomes, Science. Feb. 7, 2020; 367(6478).

\* cited by examiner

METHOD AND SYSTEM FOR SIMULTANEOUS DETERMINATION OF MULTIPLE MEASURABLE BIOMARKERS DURING THE DEVELOPMENT OF A COMMUNICABLE DISEASE

BACKGROUND OF THE INVENTION

Field of the Invention

The present invention relates generally to the analysis of infectious agents, infectious organisms or their toxic products, and biomarkers related to the infection, in biological fluids or tissue extracts using an affinity-capture-separation instrument capable of analyzing simultaneously a plurality of analytes from a single biological sample in a sequential order. More particularly, it relates to a method and system used as diagnosis of a communicable disease, a dysfunction, condition, or ailment that is affecting an individual due to the infection. The disclosure further relates to methods of detecting immunogenic compounds and biomarkers or predictors associated with the severity of the disease and to monitor the effectiveness of drug therapy or vaccination.

Description of Related Art

A communicable disease is an illness due to a specific infectious agent, infectious organism or its toxic products that arises through transmission of that agent, organism or its products from an infected person, animal, or inanimate surface or reservoir to a susceptible host; either directly or indirectly through an intermediate plant or animal host, vector, or the inanimate environment. All communicable diseases are infectious, but not all infections are communicable. Tetanus, for example, can cause an infection, but a person with tetanus cannot spread it to other people.

An infectious agent is an organism, such as virus, rickettsia, bacteria, fungus, protozoan, helminth, or its products, that is capable of producing infection or infectious disease. The ability of the disease agent to enter, survive and multiply in the host is referred as infectivity.

Although many of the major communicable diseases have become extinct, several other communicable diseases still occur, but they do occur infrequently. The rarity of these diseases makes their recognition more difficult, in particular when it becomes a deadly disease beginning with inflammation in one organ in particular and eventually becoming a multiple organ failure. New emerging infectious diseases are unpredictable and are becoming a major challenge to the medical community with potential for epidemics or even a pandemic (K. Watkins. Current Emergency and Hospital Medicine Reports volume 6, pages 86-93, 2018).

Conventional laboratory tests have been used to confirm the presence of an infectious disease; however, not all tests are simple and usually they are performed in different platforms. In fact, many tests can be time consuming, slow in getting the results, expensive, having low specificity and sensitivity, not always available to deal with a large population as it may happens in a pandemic, and in some cases the tests maybe prone to yield false positive or false negative results. A negative result does not exclude the possibility that a patient has the disease.

Some communicable diseases can be disseminated rapidly from person to person, in particularly in an area with widespread community transmission, and some people may be carriers of the infection without having symptoms of the disease. As a consequence, many asymptomatic carriers can infect other people without even knowing they are causing substantial amounts of infection. A study in Iceland, which tested a large segment of its population for the possibility of having the COVID-19 disease found 50% of the people who tested positive had no symptoms of the disease (https://www.cnn.com/2020/04/01/europe/iceland-testing-coronavirus-intl/index.html, published online on Apr. 3, 2020). Preventive self-quarantine is an effective way to contain the spread of the virus and to protect the most vulnerable from contracting a communicable disease.

In case of first responder workers, such as health personnel (physicians, nurses, technicians), policemen, firefighter, and others, it is of the utmost importance to test them as possible carriers of a communicable disease. Asymptomatic carriers are a well-known phenomenon. However, when an infectious agent or organism is a new pathogen, it may complicate efforts to detect cases and to curb transmission of the disease. There is no question that someone who is without symptoms and carrying a virus, such as HIV or coronavirus, can transmit the virus to someone else. Asymptomatic carriers are important factors in an outbreak, because they can shed the highest amount of the virus into the environment (https://www.sciencealert.com/here-s-what-we-know-so-far-about-those-who-can-pass-corona-without-symptoms; C. Rothe et al.—16 more authors. New England Journal of Medicine, volume 382, pages 970-971, 2020). Absence of evidence is not evidence of absence. People without symptoms are rarely tested, in particular in a pandemic where the numbers of tests are not available to a large population. In most cases, the tests are expensive and time consuming. The results can be obtained up to 7 days or more.

The discovery of a number of diagnostic and prognostic biomarkers for various diseases has significantly progressed in the past decade. The ability to correlate patient diagnosis and prognosis through quantification of specific biomarkers present in patient's biological fluids has been and continue to be an invaluable information in the clinical setting, particularly when symptoms of diseases are very similar, and when little is known about a disease. For example, with the pandemic due to the coronavirus SARS-CoV-2 (severe acute respiratory syndrome coronavirus 2, also known as HCoV-19) and responsible for the novel pneumonia known as coronavirus disease 2019 or COVID-19 little is known about the virus and its effect. It appears that day after day, physicians and scientists are learning new information about the transmissibility and severity of the epidemic. A disease can be highly transmissible, but not necessarily severe. Of all 7 coronavirus known to infect humans, only 3 of them, SARS-CoV-2, MERS-CoV and SARS-CoV cause severe disease in humans (K. G. Andersen, A. Rambaut, W. I. Lipkin, E. C. Holmes, R. F. Garry. Nature Medicine. https://doi.org/10.1038/s41591-020-0820-9, published online on Mar. 17, 2020). These viruses are imposing substantial mortality, morbidity and economic burden on human populations. SARS-CoV-2 infections spread rapidly and are more fatal. Furthermore, cytokine profiles are usually perturbed during viral infection. In the case of individuals with SARS-CoV-2 infection, the level of inflammatory cytokines is not only significantly higher than normal, but there is a significant correlation between cytokines levels and the severity of the disease. When an excessive or uncontrolled release of proinflammatory cytokines occurs, known as cytokine storm, a local inflammation starting in one organ can become systemic producing multi-organ dysfunction, systemic sepsis or sepsis syndrome (T. Singhal. The Indian Journal of Pediatrics, volume 87, pages 281-286, 2020).

Most diagnostic tests are carried out in different platforms by dedicated units or protocols. Traditionally, the isolation and identification of bacterial, viral or parasite infections has been performed using various types of microscopic testing, which are performed with the help of fluorescent-labeled antibodies. Cell culture tests are mostly performed for bacteria and virus, allowing the microorganisms obtained from a biosample, or clinical specimen material, to multiply and propagate in a controlled environment and conditions. The growth is slow and often the results are obtained in a couple of days. Once the microorganism causing a disease has multiplied, other tests can be carried out. For example, a susceptibility test is performed for bacteria to help to determine which antibiotic will be most effective in treating the infection. For a physician, there is nothing more disheartening than to invest considerable time, labor, and resources in test systems that yield less-than-adequate results in a less-than-timely fashion (R. L. Hodinka, L. Kaiser. Journal of Clinical Microbiology, Volume 51, pages 2-8, 2013).

Conventional diagnostic tests include molecular tests and serology tests. For example, the most common molecular test to detect viral ribonucleic acid (RNA) in clinical samples is the real-time reverse-transcription polymerase chain reaction (real-time RT-PCR). However, the success of real-time RT-PCR testing depends on several factors, including the experience and expertise of laboratory personnel, laboratory environment (e.g., avoidance of contamination), and the type and condition of specimens being tested (https://www.cdc.gov/coronavirus/mers/lab/lab-testing.html). For this real-time RT-PCR assay, the Centers for Disease Control and Prevention (CDC) recommends collecting multiple specimens for viral testing, including lower (bronchoalveolar lavage, sputum and tracheal aspirates) and upper (e.g., nasopharyngeal and oropharyngeal swabs) respiratory samples, serum, and stool specimens. Even though these molecular tests are popular and measure directly the infectious agent, in many instances the test must be repeated because a single negative result does not completely rule out an infection. These tests, in a qualitative or quantitative format, are useful and sophisticated but costly, and depending on the automation and technology utilized the results may be obtained in one day. However, there are concerns expressed in the medical community that molecular testing is not still for the majority of clinical laboratories. Issues of assay availability and accessibility remain, in particular in times of a pandemic when the volume of testing is larger of what a laboratory can provide. Furthermore, laboratory-developed assays and analyte-specific reagents are still commonly used and require considerable expertise and the equipment must undergo extensive verification and validation (R. L. Hodinka, L. Kaiser. Journal of Clinical Microbiology, Volume 51, pages 2-8, 2013).

The serology testing is usually performed to detect antibodies against the infectious agent, infectious organism or its toxic product in a person exposed to such an infectious agent, infectious organism or its toxic product. These tests are very useful for the identification of asymptomatic carriers. For example, although the person can be infected, not necessarily will develop an infectious disease. Numerous factors contribute to the development of an infectious disease. People at risk with a pre-existing disease or having more than one disease (comorbidity or multimorbidity), and usually older than 65 years of age are more susceptible to develop an infectious disease. Their immunological system maybe weak and not have enough defense mechanisms to stop the formation of the disease. Sometimes the person could be young and healthy, but the number of infectious agents causing infectivity can be very high and thus not allowing the immunological system to produce enough defenses. In other cases, the quantity of antibodies produced is more than enough to produce a strong mechanism of defense in which a person can recover of the disease, or it will not develop the infectious disease. Some people may not even be aware that they contracted the disease, because it was never developed, but they could be a carrier of the infectious agent or infectious organism and infect other people.

The most common immunoassay used primarily as a screening test is the enzyme-linked immunosorbent assay (ELISA) to determine if an antibody formed against an infectious agent is capable of blocking an infection by binding to the infectious agent. There are other assays that are performed in the laboratory which can serve as confirmation tests for a result obtained by the ELISA test. For example, the microneutralization assay is performed to measure neutralizing antibodies that binds to an infective virus which are capable of blocking a viral replication in vitro (https://www.cdc.gov/coronavirus/mers/lab/lab-testing.html). A certain group of cells are allowed to grow in cell culture, either in a plastic dish or in a flask. When a virus infectious agent is added to the cell culture and replicate, then after a certain period of time the viruses will kill the cells. These visible changes are called cytopathic effects. This visual assay is used to determine whether a serum sample contains antibodies that block a virus infection. A serum sample is mixed with virus before infecting the cells. If the serum contains antibodies that block viral infection, then the cells will survive, as determined by using a microscope or by staining the cells with a dye. If no antiviral antibodies are present in the serum, the cells will die. This assay can be quantitative or semi-quantitative; however, it is time consuming and expensive.

The sandwich ELISA test, the most frequently performed assay in the laboratory; it consists of measuring an antigen between two layers of antibodies (capture and detection antibody). The target antigen must contain at least two antigenic sites capable of binding to antibodies. The capture antibody is coated into the walls of microtiter plate. A biological fluid containing an antigen to which to antibody will bind is isolated and concentrated from the complex mixture. The antigen can be an infectious agent. After washing the excess amount of matrix, a second antibody or detection antibody, containing an immobilized enzyme is added to the microwell together with a specific substrate. After incubation, a color or fluorescence signal will be formed as a result of the enzyme-substrate reaction. The intensity of the color or fluorescence will represent the concentration of the antigen in the sample (R. M. Lequin, Clinical Chemistry volume, 51, pages 2415-2418, 2005; J. Gibbs, M. Vessels, M. Rothenberg. Application Note. https://www.corning.com/catalog/cls/documents/application-notes/CLS-DD-AN-458.pdf). The ELISA test is a mono-dimensional technique and although, in most cases, uses specific monoclonal antibodies may be prone to generate false positive results due to the polyreactivity of antibodies. The technique is performed once, and the microtiter plate is discarded after use. The ELISA test is time consuming and depending on the type of reagents it can be expensive.

Despite the increase in sensitivity and specificity of enzyme-linked immunosorbent assay (ELISA) and other immunoassay techniques, analytical interference remains to be major area of concern. Immunoaffinity capillary electrophoresis (IACE) technology, a two-dimensional immuno-capture-separation technique, overcomes many of the limitations of mono-dimensional immunoassays, such as the sandwich ELISA test, in particular the frequent incidence of false-positive and false-negative results for numerous molecules (N. A. Guzman, D. E. Guzman. Journal of Chromatography B, volume 1021, pages 14-29, 2016; K. Terato, C. T. Do, D. Cutler, T. Waritani, H. Shionoya. Journal of Immunological Methods, volume 407, pages 15-25, 2014). False-negative and false-positive results may be the result of the polyreactive nature of a significant number of antibodies, which bind not only to structurally related targets but also to structurally unrelated targets. Polyreactive antibodies are a major component of the natural antibody repertoire. In contrast to monoreactive antibodies, polyreactive antibodies have a low binding affinity for antigens, but the antigen-binding pocket of these antibodies are thought to be more flexible than the monoreactive antibodies and thereby can accommodate different antigenic configurations (A. L. Notkins. Trends in Immunology, volume 25, pages 174-179, 2004). Interfering substances that arise from properties of the specimen and interfere with the reaction of an intended target antigen and reagent antibodies can generate inaccurate results (J. Tate, G. Ward. Clinical Biochemical Reviews, volume 25, pages 105-120, 2004). Consequently, misinterpretation of diagnosis can lead to the wrong course of treatment.

U.S. Pat. No. 8,865,075 describes the development of a portable-point-of-care LACE biomarker analyzer instrument which makes it possible to improve the conditions of binding between the affinity-capture molecule immobilized to the analyte concentrator-microreactor (ACM) device, and the target analyte to be tested. For example, small amounts of a detergent, such as Nonidet P-40, can help the binding. Other factors are also crucial to optimize binding, such as the control of temperature, buffer concentrations and pH, time of reaction, use of a microwave pulse or acoustic micromixing system, and minor sample dilution with an appropriate conditioning buffer can improve binding and reproducibility of the assay. One major advantage of the design of biomarker analyzer instrument is that if the affinity molecules (e.g., antibody, antibody fragments, lectin, aptamer, others) are covalently immobilized with a well-defined orientation, and if they are stable, they can be reutilized multiple times. This advantage permits the use of well-oriented multiple affinity-capture agents, with high affinity and selectivity, in order to secure the binding of the target analyte. Particularly, in cases in which the binding of the antigen to the affinity-capture agent is weak and may generate false negative results.

The accuracy, sensitivity, and reproducibility of the tests obtained by the two-dimensional IACE technology are higher than the conventional mono-dimensional immunoassays such as ELISA. There is basically no possibility of false-negative or false-positive results when using IACE, which with some frequency can be obtained with ELISA. For example, due to the polyreactivity of antibodies, capable of interacting with related and non-related substances, if the mono-dimensional ELISA test captures non-related immunoreactive compounds, a false-positive result will be obtained. If a similar situation happens with the two-dimensional IACE technology, capturing related and not related immunoreactive compounds, there still exists the possibility of confirming the identity of each separated peak using additional tools and detectors capable of providing partial or complete characterization of the separated analytes. For example, by spiking the sample with internal standards, determining the corresponding migration time of each peak, getting absorption spectral profile and mass spectrometry for each separated compound as described in U.S. Patent Publication No. 2018/0280972.

With the advent of advanced technologies offering powerful bioengineering tools it is possible to create new affinity-recognition-capture molecules with improved and unique binding capabilities. For example, nanobodies, or single domain variable fragments of camelid heavy chain-only antibodies, have been successfully engineered as highly selective reagents, with high affinity, minimal size, low cost, and improved stability. Nanobodies are used as research tools and in medicine (I. Jovcevska, S. Muyldermans. BioDrugs, volume 34, pages 11-26, 2020). Similarly, aptamers which are short, single-stranded oligonucleotides that bind to specific target molecules have been described as affinity-recognition-capture and therapeutic reagents (S. M. Nimjee, R. R. White, R. C. Becker, B. A. Sullenberg. Annual Review of Pharmacology and Toxicology, volume 57, pages 61-79, 2017). Another group of affinity-recognition-capture reagents are lectins. Lectins are a widespread group of sugar-binding proteins occurring in all types of organisms including animals, plants, bacteria, fungi and even viruses. They are used as an effective tool for the targeting, separation, and reliable identification of glycoprotein molecules. Changes in glycoprotein and glycopeptide content, altered glycosylations, and aberrant glycan structures are increasingly recognized as cancer hallmarks (J. Hirabayashi, R. Arai. Interface Focus, volume 9, doi.10.1098/rsfs.2018.0068, 2019).

Examples of the use of two or more affinity-recognition-capture ligands or reagents has been demonstrated to improve the affinity binding to a molecule with multiple epitopes, such as thrombin (T. Goda, D. Higashi, A. Matsumoto, T. Hoshi, T. Sawaguchi, Y. Miyahara. Biosensors and Bioelectronics, volume 73, pages 174-180, 2015). Two different oligomeric DNA aptamers that can recognize different epitopes in thrombin were used in a potentiometric biosensor. The dual aptamer-immobilized configuration yield better results than the one with a single aptamer when tested for the detection of tiny amounts of thrombin. Another application employing multiple affinity-capture agents has been reported by using 6 different antibodies to capture 6 different immunoreactive chemokines in samples of cerebral spinal fluid collected from premature babies. Immunoaffinity capillary electrophoresis in microchips was used to determine the degree of brain trauma in birth traumatized premature babies. The quantification of 6 different chemokines were able to provide information of diagnosis and prognosis of the good and poor state of the babies with head trauma (T. M. Phillips, E. Wellner. Electrophoresis, volume 34, pages 1530-1538, 2013). Other examples of using multiple antibodies to capture several biomarkers have been reported by N. A. Guzman, D. E. Guzman. Journal of Chromatography B, volume 1021, pages 14-29, 2016).

The technique of microdialysis enables sample collection using a rigid or flexible probe or catheter of small molecular weight substances from brain, interstitial tissue fluid from skin, from blood, and it can be adapted to collect samples from other tissues and organs. Some of the most commonly collected target analytes are neuropeptides, neurotransmitters, hormones, but depending of the semi-permeable membrane use many substances can be collected, including cytokines. Microdialysis applications are moving slowly from preclinical evaluation and validation to clinical application (M. Müller. British Medical Journal, volume 324, pages 588-591, 2002; S. Klaus, M. Heringlake, L. Bahlmann. Critical Care, volume 8, pages 363-368, 2004; V. I. Chefer, A. C. Thompson, A. Zapata, T. S. Shippenberg. Current Protocols in Neuroscience, Chapter: Unit 7.1, doi: 10.1002/0471142301.ns0701s47, 2009; K. J. Hersini, L. Melgaard, P. Gazerani, L. J. Petersen. Acta Dermatologica Venereologica, volume 94, pages 501-511, 2014).

The human body and the diseases it develops embody enormous levels of complexity. The use of a plurality of biomarkers in the day-to-day medical practice would be advantageous for monitoring and treating diseases. It has been described that by monitoring a large number of molecules, a more comprehensive view on the development of a disease can be obtained, not only linking it to risk factors but also being able to predict when the risk would manifest itself as disease (D. Vandamme, W. Fitzmaurice, B. Kholodenko, W. Kolch. QJM International Journal of Medicine, volume 106, pages 891-895, 2013).

Traditionally diagnostic tests are based on biological fluids that utilize blood and urine for most biomarkers needed to monitor wellness and disease. For specialized tests, cerebrospinal fluids, feces, peritoneal fluid, drainage fluid, and seldom saliva, sweat, and tears can be utilized. With less frequency, biomarkers extracted from tissue biopsy, hair and nails are also utilized. Urine and saliva as biological fluids are gaining wider acceptance for diagnosing diseases. The growing interest in urine and saliva as biological fluids is due to their noninvasiveness, ease of use, cost-effectiveness, multiple sample collection, and minimal risk to health care professionals of contracting infectious organisms. Another biological fluid that provide additional biomarker information is exhaled breath condensate. For example, breath analyzer systems have been reported for the determination of organic volatile compounds and ionic content in exhaled breath condensate (M. Gregus, F. Foret, P. Kuban. Electrophoresis, volume 36, pages 526-533, 2014; M. van der Schee, H. Pinheiro, E. Gaude. Ecancermedicalscience, volume 12: ed84; doi: 10.3332/ecancer.2018.ed84, 2018; B. Abderrahman. Future Oncology, volume 15, pages 1679-1682; PCT Patent WO 03/049595; U.S. Patent US 2017/0303822). Studies of exhaled breath have demonstrated that humans generate fine particles during tidal breathing. Micron and submicron particle sizes have been detected in exhaled breath of normal and pathological people (P. Fabian, J. Brain, E. A. Houseman, J. Gem, D. K. Milton. Journal of Aerosol Medicine and Pulmonary Drug Delivery, volume 24, pages 137-147, 2011). Exhaled breath sampling and analysis has long attracted interest in the areas of medical diagnosis and disease monitoring (O. Lawal, W. M. Ahmed, T. M. E Nijsen, R. Goodacre, S. J. Fowler. Metabolomics, volume 13, 110; doi: 10.1007/s11306-017-1241-8, 2017; S. Das, M. Pal. Journal of The Electrochemical Society, volume 167, 037562; doi:10.1149/1945-7111/ab67a6, 2020); however, progress from laboratory settings to routine practice has been slow. One main reason is the number of technical problems encountered for sampling and analysis, and the lack of normalization and standardization leading to significant variations that exist between results of different studies (W. Miekisch, J. K. Schubert, G. F. E. Noeldge-Schomburg. Clinical Chimica Acta, volume 347, pages 25-39, 2004).

Mouth exhaled breath/oral fluid contains not only volatile organic compounds, but many other small and large molecules, as well as cellular and subcellular particles, including food debris. These biomolecular and cellular entities are originating from the airway, from oral cavity and gut by bacterial action, and from mucus, serous and bronchial-nasal secretions, and saliva (S. P. Humphrey, R. T. Williamson. The Journal of Prosthetic Dentistry, volume 85, pages 162-169, 2001; M. Singh, U. Singhal, G. K. Bhasin, R. Panday, S. K. Aggarwal. Journal of Pharmaceutical and Biomedical Sciences, volume 37, pages 1932-1941, 2013). Among the many substances found in exhaled breath/oral fluid are inflammatory cytokines. It is well known that inflammation is part of the host's protective immune response against microorganisms; on the other hand, if excessive, inflammation can be detrimental and increases patients' morbidity and mortality. Disregulation between pro- and anti-inflammatory has been found in exhaled breath obtained from patients with community-acquired pneumonia (S. Aliberti, L. C. Morlacchi, P. Faverio, R. Fernandez-Botran, R. Cosentini, M. Mantero, P. Peyrani, J. Ramirez, J. Bordon, F. Blasi. Pneumonia, volume 8; doi: 10.1186/s41479-016-0009-7, 2016).

The more measurements of a sample are carried out the better the precision, the smaller the error will be (J. M. Betz, P. N. Brown, M. C. Roman. Filoterapia, volume 82, pages 44-52, 2011). Internal and external standards are used as correction factors. For example, an internal standard is a chemical substance that is added in constant amount to samples, the blank and calibrations standards in a chemical analysis. An external standard is not added to the unknown, but rather is run alone, as a sample, and usually at different concentrations generating a standard curve (E. I. Muller, F. Abad, J. Dallarosa, C. Adriano. Quimica Nova, volume 33, pages 984-987, 2010). It has been suggested that point-of-care testing for infectious diseases provide actionable results near the patient under study serving as a personal "radar" (H. Chen, K. Liu, Z. Li, P. Wang. Clinica Chimica Acta, volume 493, 138-147, 2019).

In general, it is known that a panel of biomarkers may improve predictive performance over individual biomarkers, because a panel of biomarkers has the potential to detect cases missed by the use of only or a few biomarkers. This can be the case for the accurate diagnosis of infectious diseases, whether bacterial, viral, or other origin presenting acute and chronic stages of inflammation. Early detection remains the key challenge to survival of contagious infectious diseases that may spread rapidly from one organ to another and can cast a storm over the whole body ending in multiple organ failure. A cytokine storm syndrome having an hyperinflammation and characterized by elevated levels of cytokines in biological fluids can be predictors of fatality. In particular, increased levels of interleukin-2, interleukin-7, granulocyte-colony stimulating factor, interferon-gamma inducible protein 10, monocyte chemo-attractant protein 1, macrophage inflammatory protein 1-alpha, and tumor necrosis factor-alpha have been associated to mortality due to virally driven hyperinflammation, for example, in coronavirus disease 2019 (COVID-19) (P. Mehta, D. F. McAuley, M. Brown, E. Sanchez, R. S. Tattersall, J. J. Manson. Lancet; https://doi.org/10.1016/S0140-6736(20)30628-0, 2020). A complete panel of biomarkers may include not only small molecules and biomolecules, but also cellular and subcellular particles. The particles can be microorganisms such as bacteria, viruses, and others, including exosomes considered to be a trove of biomarkers (J. M. Street, E. H. Koritzinsky, D. M. Glispie, R. A. Star, P. S. Yuen. Advances in Clinical Chemistry, volume 78, pages 103-122, 2017).

Although urine is considered a convenient biological fluid to determine a panel of biomarkers, because it can be obtained using a noninvasive and safest protocol, it is not always easy to obtain a urine specimen from an infant, an older person, someone that is incapacitated, or from an individual undergoing major surgeries. Therefore, other techniques have been designed to obtain urine in difficult conditions, such as bladder stimulation and urinary catherization in infants with febrile urinary tract infection (D. Emonchy, C. Cias, E. Fontas, E. Berard, J. Breaud, P. S. Rohrlich, F. Dubos, C. Fortier, J. Desmontils, A. L. Herisse, D. Donzeau, H. Haas, A. Tran. Trials, volume 20, 783; https://doi.org/10.1186/s13063-019-3914-2, 2019). Urinary catheters are used as a help to empty the bladder, usually when a person is unable to urinate. The catheter is a sterile and flexible tube that is inserted into the bladder. Often urinary catheters are used during surgery, as the patient is unable to control their ability to urinate during anesthesia. In most cases the catheter is intended to stay in place for a long period of time. Urine drains from the bladder through the tube and into a collection bag to create a closed drainage system. In addition to urinary retention and during surgery, the catheter is also used in many patients staying in intense care units (ICU) in a hospital, who are too sick to use a bedpan. Some complications such as urinary tract infections, may arise when catheters are used for an extended period of time (L. E. Nicolle. Antimicrobial Resistance and Infection Control, volume 3, 23; doi.10.1186/2047-2994-3-23, 2014). In most cases, urinary tract infections are commonly treated with empirical antibiotics, resulting in overuse of antibiotics, which promotes antimicrobial resistance. It has been found that when urine from patients suffering of urinary tract infection is cultured, approximately only one in three patients are found to have urinary tract infection as defined by positive bacterial culture. (A. A. H. Gadalla, I. M. Friberg, A. Kift-Morgan, J. Zhang, M. Eberl, N. Topley, I. Weeks, S. Cuff, M. Wooton, M. Gal, G. Parekh, P. Davis, C. Gregory, K. Hood, K. Hughes, C. Butler, N. A. Francis. Scientific Reports (Nature), volume 9, 19694; https://doi.org/10.1038/s41598-019-55523-x, 2019. Bacterial culture may take from one to three days, or more, to get the results, depending of the type of bacteria (J-C. Lagier, S. Edouard, I. Pagnier, O. Mediannikov, M. Drancourt, D. Raoult. Clininical Microbiology Reviews, volume 28, pages 208-236, 2015).

For more than 3500 years, urinary catheters have been used to drain the bladder when it fails to empty. The Foley catheter was introduced in the 1930's. A number of publications and patents have reported urine bladder drainage tubes and collection devices or bags or apparatuses to collect urine and may be coupled or connected to a Foley catheter collection system or a modification to this system, having valves or coating materials to avoid infections (R. C. L. Feneley, I. B. Hopley, P. N. T. Wells. Journal of Medical Engineering & Technology, volume 39, pages 459-470, 2015; D. J. Stickler. Journal of Internal Medicine, volume 276, pages 120-129, 2014; L. Liu, L. Chen, N. Zhao, C. Yuan, Y. Cao. Medicine, volume 97, page 35-e12030; U.S. Pat. Nos. 5,295,979; 7,850,677).

The application of proteolytic enzymes has been reported of utility in many areas, such as biotechnology, textile, detergent-cleaning, and others (O. L. Tavano, A. Berenguer-Murcia, F. Secundo, R. Fernandez-Lafuente. Comprehensive Reviews in Food Science and Food Safety, volume 17, pages 412-436, 2018). The effects of proteolytic enzymes on the structural components of bacteria or viruses has been reported (R. J. Martinez, J. H. Shaper, N. P. Lundh, P. D. Bernard, A. N. Glazer. Journal of Bacteriology, volume 109, pages 1239-1246, 1972; S. M. Lemon, E. Amphlett, D. Sangar. Journal of Virology, volume 65, pages 5636-5640, 1991), and bacterial species identification in urine has been reported using liquid chromatography coupled to mass spectrometry (F. Roux-Dalvai, C. Gott, M. Leclercq, M-C. Helie, M. Boissinot, T. N. Arrey, C. Dauly, F. Fournier, I. Kelly, J. Marcoux, J. Bestman-Smith, M. G. Bergeron A. Droit. Molecular & Cellular Proteomics, volume 18, pages 2492-2505, 2019). Tetraspanins are recognized as specific exosomal biomarkers, as well as microRNAs (J. Lin, J. Li, B. Huang, J. Liu, X. Chen, X-M. Chen, Y-M. Xu, L-F. Huang, X-Z. Wang. The Scientific World Journal, volume 2015, http://dx.doi.org/10.1155/2015/657086, 2015). Specific biomarker signatures discriminate systemic inflammation due to viral infection versus other etiologies (D. L. Sampson, B. A. Fox, T. D. Yager, S. Bhide, S. Cermelli, L. C. McHugh, T. A. Seldon, R. A. Brandon, E. Sullivan, J. J. Zimmerman, M. Noursadeghi, R. B. Brandon. Scientific Reports-Nature, volume 7, 2914, doi:10.1038/s41598-017-02325-8, 2017). Although many of these methods are useful, they can be also time-consuming, having elaborated protocols, and expensive.

There is always uncertainty how to manage patient care of patients that may be a potential carrier of a contagious disease, such as during the COVID-19 pandemic. A patient under investigation is often placed in conservative precautions, and healthcare teams may defer or avoid certain procedures, which may have otherwise performed in other patients (M. J. Binnicker. Clinical Chemistry, 0:0, 1-3; doi:10.1093/clinchem/hvaa071, 2020). The Centers for Disease Control and Prevention (CDC) issued interim laboratory biosafety guidelines for handling specimens from suspect cases carrying a contagious disease. The guidelines are designed to prevent further transmission of the disease. Conversely, any delay in establishing a diagnosis has the potential to negatively impact patient outcomes (M. J. Binnicker. Clinical Chemistry, 0:0, 1-3; doi:10.1093/clinchem/hvaa071, 2020).

Blood is the most frequent biological fluid that can provide higher concentrations of most biomarkers, when compared with saliva, for example, that has 100- to 1000-fold less concentration of many biomarkers. However, sample collection may be an impediment when frequent monitoring is needed, and most people feel uncomfortable, fear of needles, difficult to obtain blood because of fragile or delicate veins, or difficult to locate the veins. Because of poor venous access to draw blood, or those patients who receive chemotherapy or therapy for blood disorders, they may need to be implanted with a port. However, there is some concern that routine use of implanted venous access devices predisposes the patient to complications, such as occlusion or blockage of the line or damage to the port. Another alternative is to use microdialysis probes containing a semipermeable membrane at the tip of the probe, allowing exchange of soluble molecules between the probe and the surrounding tissue where the probe is inserted, or directly into a blood vessel (M. Ye, D. T. Rossi, C. E. Lunte, Journal of Pharmaceutical and Biomedical Analysis, volume 24, pages 273-280, 2000; M. Muller, British Medical Journal, volume 324, pages 588-591, 2002; A. Zapata, V. I. Chefer, T. S. Shippenberg. Current Protocols in Neuroscience, chapter-unit 7.2, doi.10.1002/0471142301.ns0702s47, 2009; X. Kou, G. Chen, S. Huang, Y. Ye, G. Ouyang, J. Gan, F. Zhu. Journal of Agricultural and Food Chemistry, volume 67, pages 2120-2126, 2019; L. Carteron, P., P. Bouzat, M. Oddo. Frontiers in Neurology, volume 8, 601; doi.10.3389/fneur.2017.00601, 2017; U.S. Pat. Nos. 5,106,365; 5,441,481; US 2003/0236454; US 2005/0119588). Given the developments in microdialysis techniques over the past few years, it seems likely that microdialysis will become available for a broad range of diagnostic applications, including the monitoring of therapeutic drugs in the intense care unit (ICU) (J. E. van der Mast, M. W. Nijsten, J. C. Alffenaar, D. J. Touw, W. Bult. Pharmacology Research and Perspectives, volume 7, e00483, doi:10.1002/prp2.483.eCollection, 2019).

With the advent of small size components, it is possible to fabricate miniaturized conventional or microchip capillary electrophoresis instrumentation designed to obtain results in approximately 5 to 15 minutes (N. A. Guzman, D. E. Guzman. Journal of Chromatography B, volume 1021, pages 14-29, 2016; J.-Z. Pan, P. Fang, X-X Fang, T-T. Hu, J. Fang, Q. Fang. Scientific Reports (Nature), volume 1791; doi:10.1038/s41598-018-20058-0, 2018). Also, the price of the individual components has decreased significantly, which facilitate the manufacture of accessories or attachments needed for an easy control and for maintaining an optimal operation of the system (N. Mavrogiannis, M. Ibo, X. Fu, F. Crivellary, Z. Gagnon. Biomicrofluidics, volume 10, 034107; doi:10.1063/1.4950753, 2016). Speed of analysis, high sensitivity, high specificity, and high accuracy are crucial for clinical decision-making in the diagnosis and prognosis of a disease. In particular in cases of bacterial and viral infections, which often present with similar symptoms. Misdiagnosis of disease etiology may alter the trajectory of patient care, including over and under use of antibiotics. The isolation and characterization of a panel of host-protein biomarkers yields significantly superior performance for diagnosing bacterial versus viral infections. In particular in cases of adenovirus infection, which can trigger bacterial-like responses leading to misdiagnosis (L. Ashkenazi-Hoffnung, K. Oved, R. Navon, T. Friedman, O. Boico, M. Paz, G. Kronenfeld, L. Etshtein, A. Cohen, T. M. Gottlieb, E. Eden, I. Chistyakov, I. Srugo, A. Klein, S. Ashkenazi, O. Scheuerman. The European Journal of Clinical Microbiology and Infectious Diseases, volume 37, pages 1361-1371, 2018).

Numerous methods and systems have been disclosed for the diagnosis of infectious diseases. Typical embodiments are described in U.S. Pat. No. 7,220,852 and in European Patent EP 2 898 067, which disclose the use of a method to isolate coronaviruses from humans. Another method described in Australian Patent AU 2012308092 refers to the determination of microRNA in biological samples associated with virus infection in a patient infected with Henipavirus. A method for combined detection of viral and bacterial infections is described in U.S. Pat. No. 8,962,260. A method related to the agglutination of erythrocytes by viruses is described in U.S. Pat. No. 3,777,014. A method of diagnosing a bacteria-related condition in a subject using quorum sensing is described in U.S. Pat. No. 8,663,927. A method shown an increased levels of heparin-binding protein (HBP) in individuals with acute bacterial meningitis has been described in U.S. Pat. No. 9,759,720). The use of a DNA microchip for identifying fungal species is described in U.S. Patent 2011/0111970. The detection of proteins secreted by inflammatory cells in diseases characterized by symptoms of inflammation are described in U.S. Patent 2010/0311758, and in U.S. Pat. No. 8,465,941. Diagnostic tools to image tissue being infected by microorganisms are described in U.S. Patent 2016/0287728. Systems, methods, and devices for detecting infections in a clinical sample are provided in PCT Patent WO 2015/035260. Diagnostics for SARS virus are described in PCT Patent WO 2005/016132. European Patent EP 1706506 describes a sensitive and specific test to detect SARS coronavirus.

Many of the tests described in these patents have numerous shortcomings. They can be time-consuming, labor intense, usually requiring highly trained personnel, costly, limited in sensitivity, specificity and selectivity, low throughput, low accuracy, may employ radioactive materials, used only once, may be prone to false positive or false negative results, and are performed in separated platforms having different principles and utilizing numerous set of reagents.

Diagnostic tests vary in their uses and their complexity, in particular for infectious diseases. For example, in the COVID-19 disease, immunoglobulin M (IgM) is usually the first specific antibody type generated in the body in response to infection, even when there is no presence of symptoms. Then, the immunoglobulin G (IgG) type is generated and replaces IgM as the predominant antibody in the response to infection. IgM and IgG fight infections by targeting specific antigens on the surface of the SARS-CoV-2 virus. Some of the rapid diagnostic tests used to determine IgM and IgG, or for direct determination of a virus, are based on a rapid fluorescent immunochromatographic strip test (FICT). The FICT technology has been applied for the determination of influenza A virus (H1N1) (S-T. Yu, C. T. Bui, D. T. H. Kim, A. V. T. Nguyen, T. T. T. Trinh, S-J. Yeo, Scientific Reports (Nature), volume 8, 13468, doi:10.1038/s41598-018-31786-8, 2018), and the determination of IgM and IgG test for the diagnosis of highly suspected COVID-19 infected individuals (X. Jia, P. Zhang, Y. Tian, J. Wang, H. Zeng, J. Wang, J. Liu, Z. Chen, L. Zhang, H. He, K. He, Y. Liu. medRxiv (preprint), doi: https://doi.org/10.1101/2020.02.28.20029025, 2020). The determination of immunoglobulins IgM and IgG alone does not confirm the presence of virus in the system of a suspected individual with the disease. It is only a screening test to indicate that a suspected individual may has been exposed to the infectious virus. To further confirm the presence of a virus in the system of a suspected individual, a molecular genetic-based test is needed to be carried out.

The reverse transcriptase polymerase chain reaction (RT-PCR) is a popular test for the determination of the SARS-CoV-2 virus. Unfortunately, both the serological tests to measure antibodies and the molecular tests to determine the presence of the virus itself are prone to yield false positive and/or false negative results (A. Tahamtan, A. Ardebili. Expert Review of Molecular Diagnostics, volume 2020, pages 1-2, 2020; C. P. West, V. M. Montori, P. Sampathkumar. Mayo Clinic Proceedings, (https//doi.org/10.1016/j.mayocp.2020.04.004, 2020; Z. Z. Rashid, S. N. Othman, M. N. Abdul Samat, U.K. Ali, K. K. Wong. Malaysian Journal of Pathology, volume 42, pages 13-21, 2020). The overall test performance characteristics have not been reported clearly or consistently in the medical literature.

Technological advances are changing not only the way diagnostic tests are performed, but also the practice of medicine itself. Laboratory innovations have resulted in many new tests that are more efficient and automated, and less subject to user error. In addition, many tests have become less invasive or easier to administer, causing less discomfort to patients. Key trends in diagnostic test innovation include detecting disease before symptoms appear when they often can be best treated; predicting beneficial and adverse treatment effects; enabling personalized treatment regimens; facilitating point-of-care testing; and enabling rapid testing at a centralized laboratory, the hospital bedside, the physician's office, the clinic, the workplace, and even the home of an individual (AdvaMedDx, https://dx.advamed.org/sites/dx.advamed.org/files/resource/advameddx-policy-primer-on-diagnostics-june-2011.pdf, 2011).

Based on these deficiencies, there exists a need for an immunoaffinity capillary electrophoresis biomarker analyzer instrument having multi-functional capability, high sensitivity, selectivity, and accuracy for analyzing a plurality of biomarkers in a single biological specimen, and leading to the diagnosis of a communicable disease, the prognosis of the disease, and the monitoring of treatment using a single instrument platform. As a result, there is a need to develop a system and method for accurately and rapidly diagnosing or detecting an infectious agent, organism or its toxic product in a subject in order to detect an outbreak as early as possible so as to control the spread of disease among the population at risk. Furthermore, there is a need to develop a comprehensive system and method capable of providing additional information to assess the severity of the disease and the effectiveness of drug treatment and vaccination.

In the fast-paced medical world of wanting or needing an immediate and accurate diagnosis, a traditional microbiology test has lost its place and relative importance to save the life of a patient. A host can fight infections using their immune system, responding first with acute inflammation as a protective and healing mechanism, but when the immune system keeps fighting indefinitely it become a chronic inflammation. New rapid and accurate tests are needed not only to detect a microorganism, but to differentiate and quantify many different infectious agents or organisms of medical importance. It is desirable to provide a method and system for rapid analysis of infectious agents, infectious organisms or their toxic products, and biomarkers related to the infection, in biological fluids or tissue extracts which can be used for testing people that are infected or potential carriers, especially the frontline healthcare workers.

Early, accurate, and comprehensive diagnosis of diseases generally increases the chances for successful treatment by focusing on detecting crucial biomarkers in symptomatic and asymptomatic patients as early as possible. Laboratory testing is desirable at the front lines, whenever feasible and safe. It is desirable to provide physicians with answers they need to manage patients effectively during a pandemic.

SUMMARY OF THE INVENTION

In one aspect, the present invention provides an improved portable miniaturized electrophoresis apparatus for analyzing a plurality of biomarkers in biological fluids and matrices, cellular and subcellular entities and their internal and external contents, and in tissue extracts of individuals that harbor an infectious agent or microorganism or toxins secreted by an organism causing an illness, syndrome, inflammation, or communicable or non-communicable life-threating disease.

In another aspect, the present invention provides an improved portable miniaturized electrophoresis apparatus for analyzing a plurality of biomarkers in biological fluids and matrices, cellular and subcellular entities and their internal and external contents, and in tissue extracts of individuals who harbor an infection-causing agent or an infection-causing microorganism but are asymptomatic carriers of the infectious agent or microorganism and display no signs or symptoms of the disease.

In another aspect, the present invention provides a portable miniaturized electrophoresis apparatus for analyzing a plurality of biomarkers in biological fluids and biological matrices, cellular and subcellular entities and the internal and external contents, and tissue extracts of individuals who have a contagious disease due to an infection-causing agent or and infection-causing microorganism and need to be in an isolated healthcare facility or environment.

In a further aspect, the present invention provides a portable miniaturized electrophoresis apparatus adapted to obtain biological specimens directly from contagious individuals using long flexible sterile tubing connected through quick-acting fittings or connectors made to be connected and disconnected conveniently and repeatedly as needed.

In yet another aspect, the present invention provides a portable miniaturized electrophoresis apparatus adapted to obtain urine specimens directly from contagious individuals using long flexible sterile tubing connected to a modified Foley catheter or to a modified collection bag coupled to the Foley catheter.

In an additional aspect, the present invention provides a portable miniaturized electrophoresis apparatus adapted to obtain exhaled breath and/or oral specimens directly from contagious individuals using long flexible sterile tubing connected to an object-shaped as face mask, or a modified pacifier-like or soother buccal adaptor, or a modified endotracheal intubation tubing.

In yet another aspect, the present invention provides a portable miniaturized electrophoresis apparatus adapted to obtain intravenous blood sampling directly from contagious individuals using long flexible sterile tubing connected to a modified flexible, microdialysis probe system comprising a cellulose hollow fiber formed of an inert silicone elastomer.

Another aspect of the present invention is to provide a portable miniaturized electrophoresis apparatus adapted to obtain biological specimens directly from contagious individuals using long flexible sterile tubing connected through quick-acting fittings or connectors that can be operated by valves monitored by a robotically-assisted computer-controlled automatic work station system localized at a remote distance.

In a further aspect, the present invention provides a portable miniaturized electrophoresis apparatus adapted to obtain biological specimens directly from contagious individuals where the electrophoresis apparatus is localized in a containment or restricted area design to prevent the release of an infection-causing agent or an infection-causing microorganism in the event of an accident.

In an additional aspect, the present invention provides a portable miniaturized electrophoresis apparatus having at least one transport passage or capillary, at least one separation passage or capillary and an analyte concentrator-microreactor device positioned there between, at least one container to introduce a biological specimen at the inlet side of the transport passage or capillary, at least one container to introduce optimization and cleaning buffers or solutions, or buffers or solutions containing derivatizing reagents or modifiers, at the inlet side of the transport passage or capillary, at least one container to introduce separation and elution buffers or solutions at the inlet side of the separation passage or capillary, and at least one container at the outlet sides of the transport and separation passages or capillaries to receive or contain the buffers or solutions for operation of the system, or serve as waste collectors of the biological specimens, buffers or solutions.

In yet another aspect, the present invention provides a portable miniaturized electrophoresis apparatus localized in a containment or restricted area where the inlet and outlet sides of the transport and separation passages or capillaries are connected to containers hermetically sealed providing the appropriate sample carrier buffers or solutions, the appropriate optimization and cleaning buffers or solutions, and the appropriate separation and elution buffers.

In an additional aspect, the present invention provides a portable miniaturized electrophoresis apparatus localized in a containment or restricted area and positioned at a distance from the infected patient through a protective and transparent wall creating a shielded and safe environment for the patient and the healthcare personnel.

In another aspect, the present invention provides a portable miniaturized electrophoresis apparatus that can be completely operated and controlled by a computer-controlled system remotely operating at a distance from the portable miniaturized electrophoresis apparatus.

In yet another aspect, the present invention provides a portable miniaturized electrophoresis apparatus in which reliable, accurate, and scrutinized data information can be shared by secured and confidential numerical codes to other medical institutions via telemedicine during an unfolding health emergency for the benefit to global health security during an epidemic or pandemic.

In yet a further aspect, the present invention provides a portable biological fluid collection system able to store and transport a biological specimen or biosample safely from a remote location to a central laboratory and the system is capable of preserving the biological activity of immobilized biorecognition affinity ligands and target analytes present in the biological specimen.

The present invention relates to a method and system for simultaneous determination of multiple measurable biomarkers during the development of a communicable disease. The present invention provides a biomarker analyzer electrophoresis apparatus which is a portable-point-of-care immunoaffinity biomarker analyzer apparatus based on two-dimensional technology of immunoaffinity capillary electrophoresis (IACE) which overcomes many of the limitations of mono-dimensional immunoassays. The system for simultaneous determination of multiple measurable biomarkers can be implemented with devices or complementary attachments, such as sample collection systems, to provide a panel of molecular, cellular and sub-cellular biomarkers for generating comprehensive information for accurate diagnosis and prognosis of communicable or non-communicable inflammatory diseases.

Samples can be collected in a less invasive, less intrusive sample collection procedure separately and independently in a sequential order. In one embodiment, samples can be collected from long and flexible tubing connected through adapters or connectors to a portable exhaled breath device or system to collect volatile, semi-volatile and non-volatile organic compounds, including cellular and subcellular entities or particulate matter emanated from exhaled breath. In one embodiment, samples can be collected from long and flexible tubing connected through adapters or connectors to a modified exhaled breath/oral fluid collection device to collect volatile, semi-volatile and non-volatile organic compounds, including cellular and subcellular entities in mucus and saliva. In one embodiment, samples can be collected from urine specimens with long and flexible tubing connected through adapters or connectors to a modified Foley catheter or to a modified collection bag or depository. In addition, a flexible silicone microdialysis probe can be used for intravenous sampling collection, comprising a tubular dialysis membrane with inlet and outlet tubes for perfusion and sampling collection.

Individually collected samples from either an exhaled breath and/or oral biopsy collecting system, or a modified Foley catheter or collection bag, or a modified intravenous microdialysis probe collection system is passed through a relatively large-bore transport passage or capillary orthogonal positioned to a plurality of smaller-bore separation passages or capillaries. An analyte concentrator-microreactor area or device is positioned at each intersection of the transport passage or capillary and separation passages or capillaries. The collection of samples is made through hydrostatic pressure or gravity in a patient that is bedridden, or by an assisted procedure when a patient cannot exhale or urinate independently, installing a vacuum pump installed at the outlet side of the transport passage or capillary that provide a controlled minimum vacuum pressure to generate a very slow suction of a sample with the help of a miniaturized regulator and valve, to avoid blockage or perturbate the collection of sample, passing through the transport passage or capillary and through the analyte concentrator-microreactor area or device to a collecting reservoir or trapping system.

The one or more analyte concentrator-microreactor devices, with one or more affinity ligands or reagents immobilized to the inner surfaces, having one or more chemical binding principles for optimal reaction with the target analyte(s) with the purpose to concentrate the target analyte present in the biological specimen, or perform a micro-reaction, such as molecular digestion or cleavage, in order to reduce the molecular size of the target analyte, biomolecule or particulate structures or entities, or to modify the target analyte for improvements of the assay performance and/or detection sensitivity.

All reactions described above can be performed in an electrophoresis apparatus containing a format that includes either capillaries or channels. In addition, the migration of analytes can be accomplished by an electrical or mechanical pump, or a combination of both.

The present invention is able to generate accurately large amounts and different types of data in a single platform with low manufacturing costs to allow it to be affordable and readily available in the clinic. Determining a panel of host-protein signature biomarkers by a point-of-care IACE biomarker analyzer in the platform of the present invention in conjunction with clinical assessments and other laboratory findings can be used to differentiate bacterial from viral infection in a rapid, accurate, sensitive and cost-effective manner.

Advances in technology have brought down the cost of molecular and serological assays significantly and the instruments are becoming small enough to fit in a briefcase. This has made it easier for a large number of samples to analyzed around the world. However, a significant amount of the data obtained is not accurate, and still the results can be false positive or false negative. Conventional systems and methods have not been universally standardized due to the use of multiple and different testing platforms, different principles of operations, heterogeneity of reagents, or not enough specificity and sensitivity. In an era of a pandemic, such as with coronavirus disease (COVID-19) caused by the severe acute respiratory syndrome coronavirus 2 (SARS-CoV-2) there is a need for fast and accurate diagnostic test for infectious diseases having uniformity in sample collection, testing, and complete standardization to be able to compare values of diagnostic, prognostic, response to therapy to share by telemedicine and artificial intelligence. This process provides more understanding about the incubation period (time of exposure to the development of the symptoms) of the virus, the time of developing neutralizing antibodies for protection, whom are carriers of the disease without symptoms, and whom will develop the disease with mild symptoms, and severe symptoms. The biomarker analyzer electrophoresis apparatus of the present invention being a miniaturized, portable point-of-care IACE bioanalyzer electrophoresis apparatus provides fast and accurate test results.

In addition, the biomarker analyzer electrophoresis apparatus can be implemented to be used, in conjunction with telemedicine in remote places including a central processing unit (CPU) system that executes instructions using electronic circuitry and a computer which can be combined in an artificial intelligence system. Accurate data sharing can lead to faster-than-ever outbreak research.

A more complete understanding of embodiments of the present disclosure will be afforded to those skilled in the art, as well as a realization of additional advantages thereof, by a consideration of the following detailed description of one or more embodiments.

Figure 1:
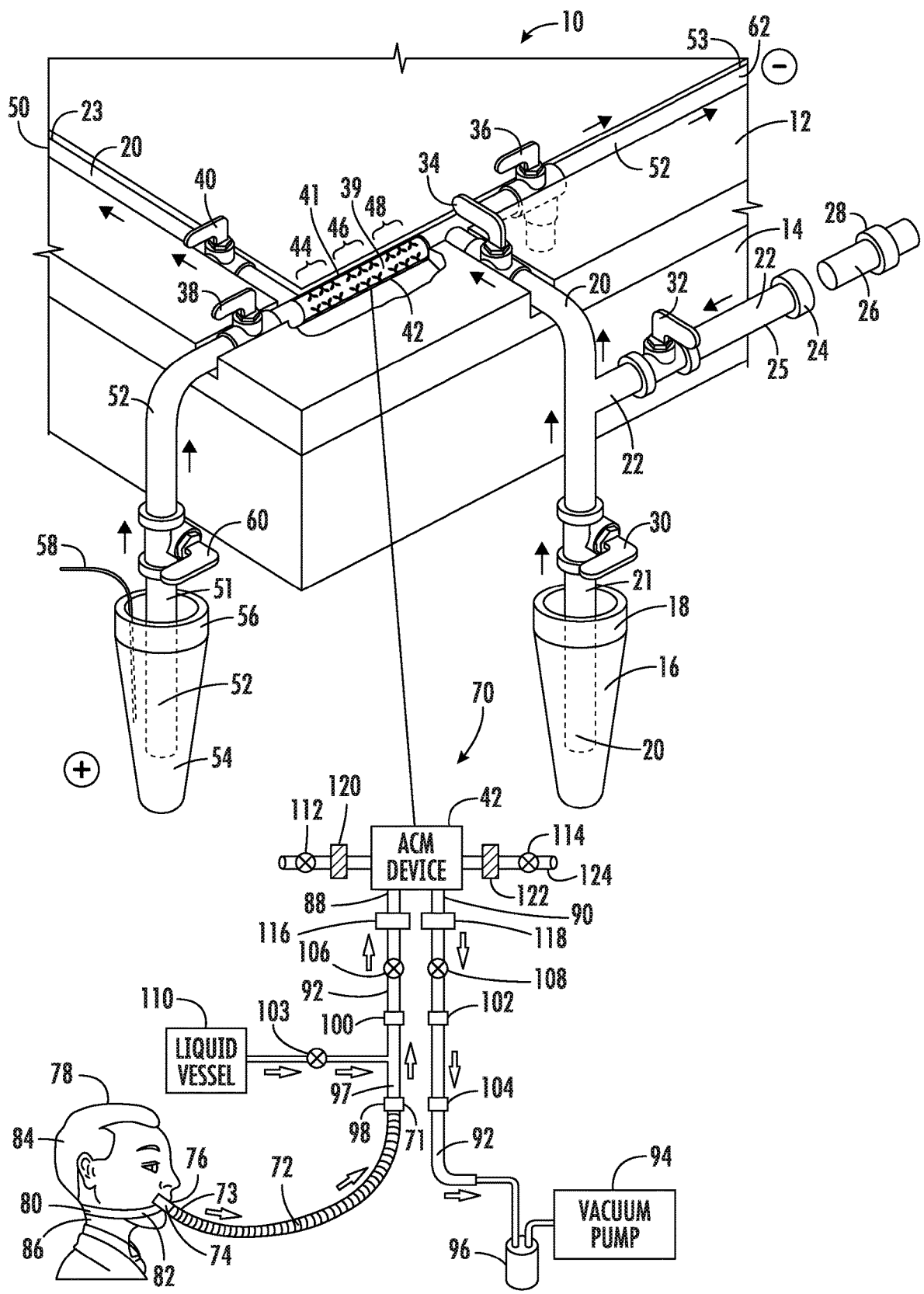
FIG. 1 is a schematic view of a portable biomarker analyzer electrophoresis apparatus to analyze one or a panel of biomarkers, and a portable exhaled breath and oral fluid collection system to collect volatile, semi-volatile and non-volatile organic compounds, including cellular and subcellular entities or particulate matter emanated from exhaled breath or present in oral fluid, mucus, serous and bronchial-nasal secretions, and saliva, containing target biomarkers to be analyzed.

Embodiments of the present disclosure and their advantages are best understood by referring to the detailed description that follows. It should be appreciated that the figures may not be necessarily drawn to scale.

DETAILED DESCRIPTION

Reference will now be made in greater detail to a preferred embodiment of the invention, an example of which is illustrated in the accompanying drawings. Wherever possible, the same reference numerals will be used throughout the drawings and the description to refer to the same or like parts.

FIG. 1 illustrates portable biomarker analyzer electrophoresis apparatus 10 of the present invention. Portable biomarker analyzer electrophoresis apparatus 10 can perform single or multiple sample studies analyzing one or a plurality of chemical, biological, cellular, subcellular and/or particulate material biomarkers present in simple and complex chemical or biological matrices. Suitable and representative analytes can include: ions, small molecules, such as metabolites and peptides; biomolecules, such as glycoproteins and polysaccharides; cellular entities, such as bacteria and blood cells; subcellular entities, such as mitochondria and ribosomes; particulate agents, nanoparticles or microvesicles, such as viruses or exosomes; and substances or entities having simple and complex structures.

As shown in FIG. 1, portable biomarker analyzer electrophoresis apparatus 10 includes platform 12 having side wall 14. Container 16 can include tube cap 18. Container 16 can be a cup. Container 16 can contain a sample or a buffer. Container 16 is mounted laterally on side wall 14. Transport passage or capillary 20 transports a biological specimen or cleaning-washing buffers from inlet side 21 of transport passage or capillary 20 positioned in container 16 to outlet side 23 of transport passage or capillary 20 connected to waste container 50. For example, transport passage or capillary 20 can be a large bore capillary having a length in the range of about 100 to about 800 mm, and an inner diameter in the range of about 200 to about 3000 µm. Fluid transported through transport passage or capillary 20 passes through analyte concentrator-microreactor (ACM) device 42. The direction of passage of fluid in portable biomarker analyzer electrophoresis apparatus 10 is controlled by micro-valves 30, 32, 34, 36, 38 and 40. Micro-valves 30, 32, 34, 36, 38 and 40 can be operated manually or by a motorized system operated by a computer. In one embodiment, analyte concentrator-microreactor (ACM) device 42 serves as a solid support immobilization framework where one or more chemical and/or biological biorecognition compounds or affinity ligand molecules can be attached with the purpose of binding or capture of one or more biomolecules, such as simple-structured biomolecules, or entities having complex biological structures, such as cellular or smaller size entities, present in a biological specimen or biosample and containing more than one epitope or binding site to where a selective binding will occur. Analyte concentrator-microreactor (ACM) device 42 can contain a beaded or a porous polymeric-monolithic matrix in its inner cavity where chemical and biological affinity ligands can be immobilized, or alternatively immobilization of affinity ligands can also be performed directly to the inner surface of analyte concentrator-microreactor (ACM) device 42. In one embodiment, affinity ligands or biorecognition molecules can be immobilized onto magnetic beads that can be retained within analyte concentrator-microreactor (ACM) 42 by one or more magnets. Representative analyte concentrator-microreactor (ACM) devices having a staggered configuration where a plurality of different microstructure matrices, containing immobilized affinity ligands, can be installed or deposited in an inner cavity or immobilization to an inner surface of the analyte concentrator-microreactor (ACM) device have been described in U.S. Pat. Nos. 7,329,388; 9,146,234; 9,696,299; and 10,408,789, hereby each incorporated by reference into this application. In one embodiment, affinity ligands or biorecognition molecules can be immobilized onto non-magnetic matrix substrates that can be retained within analyte concentrator-microreactor (ACM) 42. Suitable non-magnetic matrix substrates can be made from glass, plastic or other polymeric materials, ceramic or metallic compositions, and mixtures thereof. Suitable magnetic matrix substrates can be magnetic metal-containing matrix substrates.

Analyte concentrator-microreactor (ACM) device 42 can contain more than one affinity ligand immobilized to chemical groups localized on a surface of the solid support matrix, which can be positioned within internal cavity 39 or to a surface of inner wall 41. Affinity ligands 44, 46 and 48 immobilized in an oriented position to capture the corresponding target analytes, can have affinity binding specificity for three different analytes or can have affinity for three different epitopes of a single biomolecule, cellular or biological particle or vesicle. Weak affinity ligands may lead to a false negative result. Multiple affinity ligands to various epitopes can firmly secure the binding to the target analyte, providing accurate results and avoiding negative results. Affinity ligands 44, 46 and 48 can be preferentially antibodies, antibody fragments, lectins, aptamers, or any chemical and biological molecule or entity of any size and chemical structure that have an attraction for a target analyte originated from natural sources or that can be made artificially using chemical or biological synthesis protocols. Suitable affinity ligands 44, 46 also include metal ion, dye, biotin, avidin, cellular receptor, protein A, protein G, protein L, hormone, poly-A (multiple adenosine monophosphates), boronate, recombinant protein, fusion protein, chemically or biologically modified protein or nucleic acid, cellular or subcellular entity, cellular vesicle, vitamin, enzyme cofactor, enzyme inhibitor, enzyme substrate analog, natural or synthetic small molecule, metabolite, polysaccharide, modified polysaccharide, natural or synthetic biopolymer, complementary base sequence, histones, carrier protein, cytokines, ferritin, heparin, triazine, or cellular membrane.

Container 16, having cover cap 18, can receive biological specimens such as urine, saliva, plasma, serum, cerebrospinal fluid, tears, sweat, peritoneal or ascitic fluid, lavage fluids, exhaled breath condensates, and extracted material from biopsies, tissues, organs, nails, hair, feces, or the source of various tissue or organ lavages such as bronchoalveolar lavage fluid samples. All biological fluid specimens are centrifuged and/or filtered to eliminate aggregates and large particle materials if the target analytes are chemical and biochemical molecules, and transported hydrodynamically by pressure or vacuum through transport passage or capillary 20 all the way to outlet side 23 of transport passage or capillary 20 connected to waste container 50, or a trap reservoir coupled to a controlled-suction vacuum pump. A sequence of selective porosity filters can be used with the biological fluid specimens to retain larger aggregates but allowing bacteria and virus to pass or even blood cells if the target analyte is a particle entity. Alternatively, biological fluid specimens contained in a specimen collecting container having coupling tube 26 can be hermetically connected to transport passage or capillary 22 with adapters or connectors 24 and 28. The biological fluid specimen can be transported through transport passages or capillaries 20 and 22, passing through analyte concentrator-microreactor (ACM) device 42, all the way to the outlet end 23 of transport passage or capillary 22 connected to waste container 50.

The transport of fluid through transport passages or capillaries 20 and 22 is coordinated by the opening and closing of microvalves 30, 32, 34, 36, 38, and 40 operated manually or by computer control. A first set of microvalves 32, 36 and 38 are closed and microvalves 30, 34, and 40 are open. A biological fluid specimen containing target analytes is transported from inlet side 21 of transport passage or capillary 20 placed in container 16 to outlet side 23 of transport passage or capillary 20, passing through analyte concentrator-microreactor (ACM) device 42 containing affinity-capture ligands or reagents 44, 46, and 48 to retain one or more target analytes. Container 16 can be replaced by a buffer or solution container (not shown). This replacement step can be made manually or by a computer controlled rotatable table, turntable, or carrousel mechanism of the type described in U.S. Pat. No. 5,045,172 which is hereby incorporated by reference into this application. Thereafter, a quantity of cleaning or washing buffer or solution is introduced into transport passage or capillary 20 to remove excess of salts and all unwanted substances or materials non-specifically bound to the inner walls of transport passage or capillary 20 and to the area of analyte concentrator-microreactor (ACM) device 42. At this stage, microvalves 30, 32, 34, and 40 manually operated or computer-controlled are closed and microvalves 36, 38, and 60 are open.

In one embodiment, container 54 can contain a separation buffer. A first end at inlet side 51 of separation passage or capillary 52 is initially placed in container 54, having cover cap 56, followed by filling separation passage or capillary 52 with separation buffer hydrodynamically (pressure or vacuum) from inlet side 51 to outlet side 53 of separation passage or capillary 52 to waste container area 62, serving as a grounding zone for grounding electrode (not shown). A second end at outlet side 53 of separation passage or capillary 52 is placed in a second separation cup (not shown), an area where one or more detectors are localized and connected on-line or off-line to separation passage or capillary 52 using different principles of detections.

Similarly, the biological fluid specimen introduced hydrodynamically (pressure or vacuum) through secondary transport passage or capillary 22 follow the same technical procedure as the sample introduced through main transport passage or capillary 20, except that microvalve 30 is closed and microvalve 32 is open when the biological fluid specimen is introduced from coupling tube 26 to inlet 25 and connecting side of separation passage or capillary 22 to flow to outlet end 23 of transport passage or capillary 20 where waste container 50 is localized. The entire system is hermetically sealed to avoid leakage of fluid out of the system and formation of air bubbles at the entrance of air. Container 54 is localized at inlet side 51 of separation passage or capillary 52. Tube 58 can be associated with separation buffer container 54 where a platinum-iridium electrode can be placed and also an inert gas can be introduced to container 54 to generate a pressured sample introduction and also pressure for sample separation. Outlet side 53 of separation passage or capillary 52 containing another separation cup with another platinum-iridium electrode (not shown) and where waste container area 62 is localized and serves as a ground or earth connection reservoir of the electrical circuit.

The protocol for sample introduction or sample separation of the released or desorbed target analytes bound reversibly to one or more of the immobilized affinity ligands can be made by electrical motion, electroosmotic flow, mechanical pressure, or a combination of electroosmotic flow and mechanical pressure. In a similar way, a small amount or plug of a desorption or elution buffer or solution is introduced into the separation passage or capillary to release bound substances in a batch or stepwise elution fashion or in a sequential elution order using a radiation or thermal or chemical method, followed by a separation buffer to separate the released target analytes in separation passage or capillary 52. The elution buffer or solution can also contain one or more tagging substances or chromophores to tag or derivatize the bound analyte at the same time that is released from the immobilized biorecognition affinity ligand. Derivatized target analytes can have enhanced detectability and can be detected at a much lower concentrations than those analytes not derivatized, and also can have a different selectivity separating the molecules at different migration times than the non-derivatized counterpart molecule. The separation process starts at the switching-on of the high-voltage power supply, localized near container cup 54, which can be made manually, or computer controlled. As the bound target analytes are released from their respective immobilized affinity ligands, they are separated individually in separation passage or capillary 52, they can be detected, quantified, and characterized by one or several detectors positioned on-line/in-line or off-line, including UV-Vis absorption spectrometric, fluorescence, amperometric, contactless conductivity, electrochemiluminescence, radiometric, circular dichroism, nuclear magnetic resonance, and mass spectrometry. The high separation power of capillary electrophoresis, by adjusting voltage and amperage, is accomplished in conjunction with appropriate buffers containing additives to improve separation, for example addition of cyclodextrins as chiral selectors to separate enantiomeric pairs, and maintaining the separation buffer or background electrolyte under optimal conditions of concentration of salts, pH, temperature, and viscosity (R. L. C. Voeten, I. K. Ventouri, R. Haselberg, G. W. Somsen. Analytical Chemistry, volume 90, pages 1464-1481, 2018; J. S. Torano, R. Ramautar, G. de Jong. Journal of Chromatography B, volume 1118-1119, pages 116, 136, 2019; R. B. Yu, J. P. Quirino. Molecules, volume 24, 1135, doi:10.3390/molecules24061135, 2019). In some instances, a gently shaking of magnetic beaded matrices or use of a microwave or acoustic micromixing system can aid in improving the efficiency of the binding process and even may accelerate the binding process to occur in a short period of time. Separation passage or capillary 52 can be connected to an auxiliary tube or capillary, as shown in U.S. Pat. Nos. 7,329,388; 9,146,234; 9,696,299; 10,408,789, each of which is hereby incorporated by reference into this application, allowing the entrance of an optimal separation buffer or solution compatible with mass spectrometry, such as certain volatile buffers as ammonium bicarbonate, ammonium acetate, ammonium formate and others.

After the entire process of separation has been completed, transport and passages or capillaries 20, 22 and separation passage or capillary 52 can be reconditioned to start a new cycle of analysis for a new sample. Site-selective orientated immobilization of biorecognition molecules is the key to develop efficient diagnostic and separation tools for many applications, including quality control, primarily in the pharmaceutical industry, clinical diagnosis, forensic science, food and beverage, cosmetic, artistic and historic conservation works, chemical warfare, and environmental monitoring. There are many advantages to use suitable immobilization approach, one of them is the maximum functionality of the immobilized antibody, lectin, aptamer or fragments of these biorecognition molecules by site-directed and the other is the re-utilization of the immobilized affinity ligand molecules.

Portable biomarker analyzer electrophoresis apparatus 10 can be used as a miniaturized, portable IACE point-of-care bioanalyzer electrophoresis instrument. Portable biomarker analyzer electrophoresis apparatus 10 can be manufactured for use with tubular fused-silica capillaries or tubular plastic capillaries as conventional capillary electrophoresis system, or it can be adapted for use with polymeric plastic channels as microchip capillary electrophoresis system. Portable biomarker analyzer electrophoresis apparatus 10 can be manufactured to operate with high-voltage power supplies having independent positive or negative polarities, or operate with high-voltage power supply having a reversed-polarity system. The power supplies can operate manually, or computer controlled.

FIG. 1 also illustrates portable exhaled breath and oral fluid collection system 70 that complements the functionality of biomarker analyzer electrophoresis apparatus 10 of the present invention. Transport passage or capillary 92 is coupled to inlet side entrance port 88 of modular and portable analyte concentrator-microreactor (ACM) device 42, and the other end is coupled to end 71 of tube 72 through adapter or connector 98, 100 and 116. Oral adapter or connector 74 is connected to end 73 of tube 72. End 73 of tube 72 is adapted to be received in mouth 76 of individual 78 exhaling or emanating a breath/oral fluid matrix, a complex mixture of condensate of exhaled gas, various sizes of micron and sub-micron particles/droplets that are aerosolized, containing volatile (water soluble volatiles that are exhaled and absorbed into the condensing breath), semi-volatile, and non-volatile compounds. Controlled suction generated from vacuum pump 94 can aid the mobilization of saliva as well, generating a collection of a plurality of cellular, subcellular, particles, globules, and vesicular entities such as bacteria, viruses, fungi, other microorganisms, exosomes, and their contents, as well as organic and inorganic compounds, such as ions, proteins, allergens, lipids, cortisol, nitric oxide, mucins, immunoglobulins, enzymes, cytokines and many others. Fastener device system 80 is configured to maintain tubing 72 to mouth 76 of individual 78 through adapter or connector 74. Fastener device system 80 can include band 82. Band 82 extends around head 84 or neck 86 of individual 78 and is connected to adapter or connector 74. Individual 78 can be a person or animal.

Many volatile, semi-volatile, and non-volatile compounds may be difficult to extract from a fluid, in particular when derived from complex biological and non-biological fluids. Some of these compounds fall into different chemical classes, such as acidic, basic, neutral, halogenated, oxygenated, polar, non-polar, low-boiling, and high-boiling compounds. Liquid container or vessel 110 can be connected to transport passage or capillary 92 to provide an appropriate extraction or dissolution buffer or solution containing non-denaturing high-quality detergents with the minimal amounts of peroxide and aldehyde contaminants to facilitate breakdown, extraction and dissolution of cellular, subcellular, globules, particles and vesicular entities as well as aggregated complexes and viscous solutions. The extraction-dissolution buffer or solution can also contain chelating compounds and digestive enzymes if necessary, to breakdown larger biopolymers and particle entities. Additionally, liquid container or vessel 110 can be adapted to provide a range of controlled temperatures to the entire system to maintain at maximum solubility all components and substances present in the biological fluid mixture obtained from portable exhaled breath and oral fluid collection system 70. Temperature regulated buffer or solution containing the extracted/dissolved materials and compounds can also facilitate the binding of biomarkers to the biorecognition affinity ligands immobilized to analyte concentrator-microreactor (ACM) device 42.

Liquid container or vessel 110 is connected to transport passage or capillary 92 through adapter or connector 97 and couplers 98 and 100. Adapter or connector 97 can be a T shaped connector tube. Outlet end 90 of transport passage or capillary 92 can be connected directly to trap or waste container 96 and vacuum pump 94 or through adapters or connectors 118, 102 and 104. Vacuum pump 94 can generate a controllable vacuum maintaining a uniform flow from the collecting area of portable exhaled breath and oral biopsy collection system 70 starting at mouth 76 with adapter or connector 74 to outlet side of transport passage or capillary 92 ending in trap or waste container 96. As the collected sample is transported within portable exhaled breath and oral fluid collection system 70 to trap or waste container 96, it can be mixed with an optimized extraction or dissolution buffer or solution stored in liquid container or vessel 110 containing several aid components, including detergents, to dissolve as much as possible materials without altering the binding properties of the target analytes that will be trapped at analyte concentrator-microreactor (ACM) device 42 and to overcome differences in surface tension, density, and viscosity. In addition to avoid clogging of inner space of analyte concentrator-microreactor (ACM) device 42 adapter or connector 116 is equipped with porous filters derived from cellulose material, carbon, or polymeric plastics to retain non-dissolved materials facilitating a smooth transport of filtered materials passing through analyte concentrator-microreactor (ACM) device 42. The filters can be coated with different chemical and/or biochemical components. For example, if it is necessary to eliminate digestive enzymes from the extraction or dissolution buffer or solution because of altering or digesting some of the immobilized affinity ligands, they can be immobilized on membranes of adapter or connector 116. Alternatively, or additionally, adapter or connector 97 can also contain immobilized one or a mixture of digestive enzymes in its inner surface, and the inner portion of transport passage or capillary 92 localized between adapter or connector 100 and adapter or connector 116.

For the transport of exhaled breath and oral fluid to occur under optimal conditions, adapter or connector 74 can be positioned in mouth 76 with the aid of a fastener system 80. Microvalves 112 and 114 are closed, and microvalves 106, 108 are open. Once the aspiration system is working smoothly, microvalve 103 is opened to allow the extraction or dissolution buffer or solution in liquid container or vessel 110 to enter at adapter or connector 97, where the mixing of particle structures, materials or entities, and/or chemical or biochemical compounds of the exhaled breath/oral liquid with the extraction/dissolution buffer or solution will occur. Separation passage or capillary 124 corresponds to an area where the exhaled breath/oral biopsy collection system can be coupled to biomarker analyzer instrument 10, in replacement of transport capillary or passage 52 and container 54, or another similar analytical separation instrument such a high-performance liquid chromatography or a similar capillary electrophoresis system.

Portable exhaled breath and oral fluid collection system 70 can be adapted for the determination volatile, semi-volatile and non-volatile organic compounds in other biological fluids derived from nasal and nasopharyngeal aspirate fluids, airway secretions, nipple aspirate fluids, and fluids derived from washes, lavages, and aspirates, and from skin emanation. The sample specimen exhaled breath and oral fluid, such aaerosolized droplets, saliva or sputum, urine, plasma, serum, sweat, tears, bile, tissue-organ lavages, cerebrospinal fluid, amniotic fluid, pericardial, fluid, pleural fluid, abdominal fluid, ear fluid, or extracted material from fresh or frozen semen, ovum, nail, hair, feces, vomit, whole blood or dry blood spots, buccal swab, throat swab, nasopharynx swab, suprapubic aspirate, vagina fluid, vagina swab, endocervical swab, urethra discharge, mucus, rectal swab, lesion/wound/abscess swab, tissue biopsy, organ biopsy, umbilical cord, placenta, skin scrape, bone marrow, stem cells, circulating cells, exosomes, necropsy tissue, microorganisms-parasites-fungus-virus, and/or food residues found in the sample specimen can be collected, processed and/or stored by a number of protocols for conditions of preserving the specimen, including anti-bacterial growth chemicals, slightly acidic solutions of nitrite, chelating reagents, hydrochloric acid, acetic acid, oxalic acid, tartaric acid, boric acid, chlorhexidine, ethyl paraben, thymol, sodium propionate, bicarbonate salts, merthiolate or thimerosal, iodine, formalin, polyvinyl alcohol, copper, zinc, a cocktail of these substances, and/or paraffin. Portable exhaled breath and oral liquid fluid collection system 70 can be adapted to be used for the determination volatile, semi-volatile and non-volatile organic compounds in non-biological fluids derived from aqueous, soil and air samples or emanated by or derived from flowers, plants, allergens, food or materials that may be of relevance to the fragrance and flavors industries, textile and/or coloring industries, and environmental pollution.

Analyte concentrator-microreactor (ACM) device 42 preserves stability of the biorecognition affinity ligands immobilized to analyte concentrator-microreactor (ACM) device 42 when stored, exposed to changes of temperature, or transported for longer periods of time from remote locations to a central laboratory where the analysis will be performed. Adapters or connectors 116, 118, 120, 122 can secure the total hermetic sealing of analyte concentrator-microreactor (ACM) device 42 and the convenience of smoothly coupling together to the corresponding adapters of portable biomarker analyzer electrophoresis apparatus 10 of the present invention.

Figure 2:
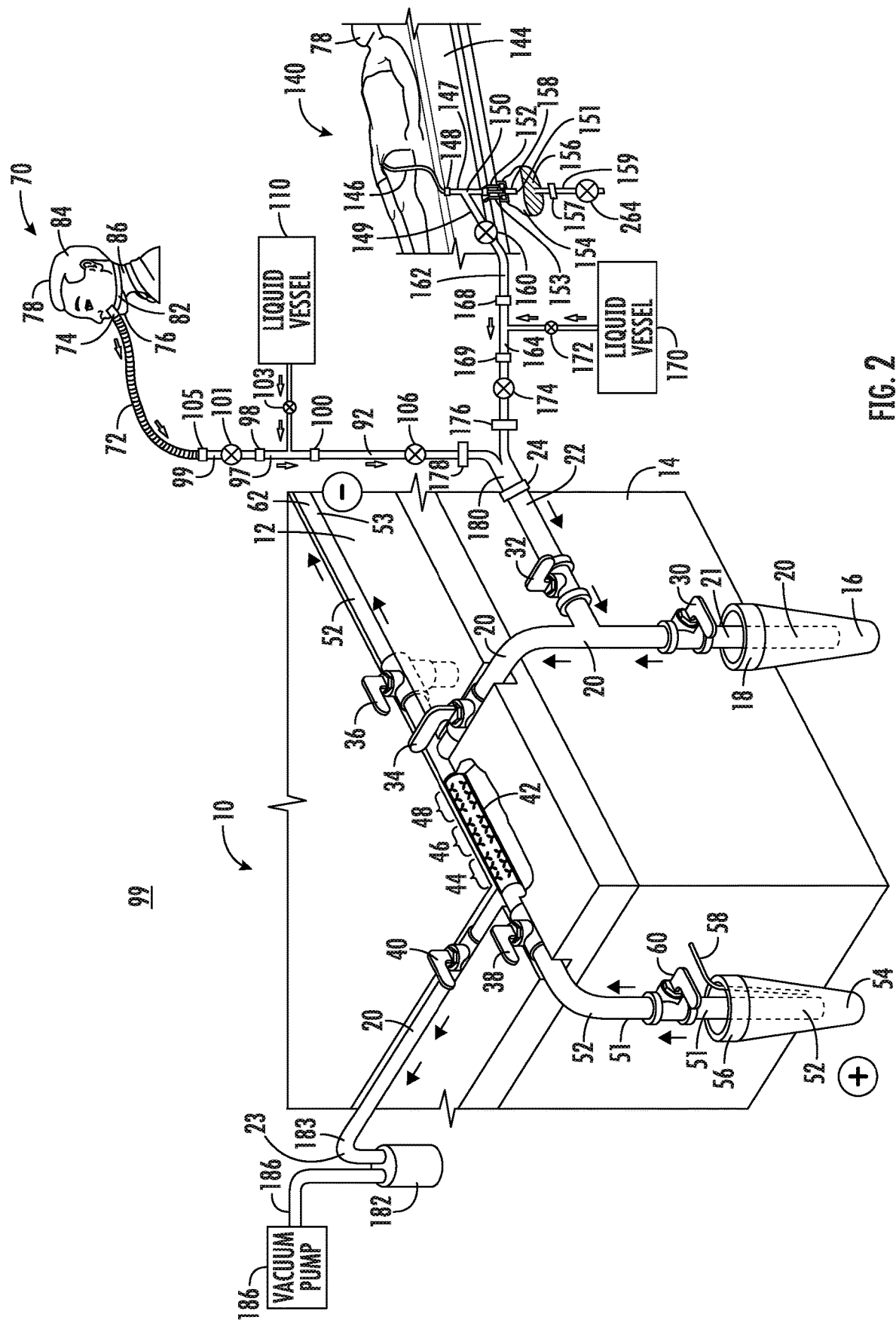
FIG. 2 is a diagrammatic perspective view that illustrates an embodiment of the portable biomarker analyzer electrophoresis apparatus including a portable exhaled breath and oral fluid collection system, and a Foley catheter urine collection system, connected to each other by a coordinated hermetic and dynamically coupling system using appropriate couplers and adapters, and also connected to an additional reservoir containing a detergent-containing solution to facilitate the passage and solubility of the biological fluid components.

FIG. 2 illustrates an embodiment of three separate and independent operating systems or apparatus connected together and capable of functioning in coordination and sequentially to provide an integrated and comprehensive healthcare information by generating a panel of biomarkers accurately, rapidly and reliable. Portable integrated multidisciplinary biomarker analyzer system 99 comprises portable biomarker analyzer electrophoresis apparatus 10, portable exhaled breath and oral fluid collection system 70, and Foley catheter urine collection system 140, connected to each other by a coordinated hermetic and dynamically coupling system using appropriate couplers and adapters. Portable integrated multidisciplinary biomarker analyzer system 99 enables assessment of a comprehensive and representative number of biomarkers or a panel of biomarkers to provide rapid, sensitive, selective, reliable and accurate diagnostic tests which enables physicians to provide prompt and effective therapy. In the context of infectious diseases time and accuracy is crucial. While certain microorganisms, such as infectious viruses that can replicate very quickly, attacking and killing cells in all cases, they can also trigger a powerful and counterproductive overreaction by the immune system, accelerating an inflammatory damage that can end in a "cytokine storm", multiple organ failure and death. Portable integrated multidisciplinary biomarker analyzer system 99 is designed to perform near patient testing, in particular for critically ill patients, as reliable and accurate as possible. Traditionally, diagnostic tests have the shortcoming of not providing complete certainty, and the veracity of diagnosis is always an approximation. Such incomplete or erroneous diagnosis may be due to the limited number of biomarkers tested, poor sensitivity and selectivity of the assay, and/or the several platforms used for performing each individual assay having different standardized guidelines and protocols. Portable integrated multidisciplinary biomarker analyzer system 99 includes coupling of portable biomarker analyzer electrophoresis apparatus 10 having a single platform to two biological fluid or biosample collecting systems, portable exhaled breath and oral biopsy fluid collection system 70 and Foley catheter urine collection system 140, in order to provide the capability of assaying a panel of useful biomarkers yielding a more complete discriminative ability to differentiate a healthy individual from an ill patient, and predict accurately the degree of severity of a disease in a relatively short period of time.

Portable biomarker analyzer electrophoresis apparatus 10, and portable exhaled breath and oral fluid collection system 70 are described in FIG. 1 when functioning separately and independently. Referring to FIG. 2, portable biomarker analyzer electrophoresis apparatus 10, and portable exhaled breath and oral fluid collection system 70 work coupled to each other and in conjunction with Foley catheter urine collection system 140. Foley catheter 146 of Foley catheter urine collection system 140 is configured to collect urine from individual 78 lying down in bed 144 and Foley catheter 146 has been placed through his/her urethra, the opening through which urine passes, into the bladder. Foley catheter 146 can be formed of a rubber, plastic or silicone tube. Foley catheter 146 helps drain urine from the bladder and is conventionally used by some patients who have had urological or gynecological surgery, or who have a condition that makes urination difficult. Foley catheter 146 can be used indwelling or intermittent for a short or long period of time. Foley catheter 146 is connected with adapter or connector 148 to angle connector 150. Angle connector 150 is connected to tubing 158 using adapter or connector 152. Angle connector 150 can have a 45-degree angle connecting to valve 160. Outlet portion 151 of tubing 158 ends inside urine collection or drainage bag 154 where urine 156 is collected. All parts of the connecting system related to urine collection or drainage bag 154 is hermetically sealed and sterilized to avoid any kind of leakage and to prevent infection. Any excess amount of urine can be eliminated from urine collection or drainage bag 154 using tube 159 controlled by valve system 264 containing an adjacent filter 157. It is typically not possible or convenient to sterilize plastic urine collection bags after they have been used in a catheter for a certain amount of time. Urine collection or drainage bag 154 can be replaced after use for a certain period of time. Alternatively, catheter valves can be used without urine collection or drainage bag 154 for reducing the possibility of catheter blockage. Support or holder device 153 can be attached to bed 144, a wheelchair, or to a leg of individual 78 to prevent urine collection or drainage bag 154 from moving or shaking. Urine collection or drainage bag 154 is retained in a gravity position to avoid reflux of urine from urine collection or drainage bag 154 into the bladder, and maximum hygiene must be maintained at all times to avoid any kind of infection. Adapter or connector 152 connects angle connector 150 to support or holder device 153.

Adapter or connector 164 can be a T shaped connector to connect liquid vessel 170 to transport passage or capillary 162. Adapters or connectors 168 and 169 are positioned in transport passage or capillary 162. Adapter or connector 176 is positioned between transport passage or capillary 162 and transport passage or capillary 22. Adapter or connector 178 is positioned between transport passage or capillary 92 and transport passage or capillary 22. Adapter or connector 180 can be a splitter connector for connecting transport or capillary 92 with transport or capillary 162 and transport or capillary 22. Adapters or connectors 24, and 176 can have sequential filters of different porous sizes or a membrane filtration system to avoid any larger aggregated or particles to enter into transport passage or capillary 22, but still may allow to pass small and large molecules, free circulating cells, viruses, subcellular particles, and exosomes.

Valve 160 is positioned between angle connector 150 and transport passage or capillary 162. Valve 172 is positioned between liquid container or vessel 170 and transport passage or capillary 162. Valve 174 is positioned between transport passage or capillary 162 and transport passage or capillary 22. For collection of a urine sample from Foley catheter urine collection system 140, valves 160, 174, 32, 34, and 40 are open, and valves 264, 172, 106 30, 36, and 38 are closed. When vacuum pump 186 is activated to generate a controlled and smooth suction, chemical, biochemical, cellular, sub-cellular, and particle compounds or entities passed through analyte concentrator-microreactor (ACM) device 42 all the way through transport passages or capillaries 162, 22, and 20, and adapters or connectors 164 and 180, to outlet end 183 of transport passage or capillary 20. To facilitate free and smoothly passage, valve 172 is opened to allow the mixing of the detergent-containing buffer or solution stored in liquid container or vessel 170 with the urine collected from the Foley catheter urine collection system 140. This detergent-containing buffer or solution aid to maintain solubility of analytes in the urine. Adapter or connector 164 and adapter or connector 180 can also contain digestive enzymes immobilized to their surfaces to aid to maintain solubility of analytes present in the urine of individual 78 by cleaving large biomolecules into smaller molecular components. The absence of digestive enzymes in the detergent-containing solubility buffer and the presence of immobilized enzymes in adapters or connectors 97, 178, 164, 176, and 24 also serve as aid to digest larger aggregates of materials or compounds, and to avoid any clogging of the various passages, tubes, or capillaries permitting a smooth and freely passing of fluids obtained from the Foley catheter urine collection system 140 or from the exhaled breath/oral fluid collection system 70. The immobilization of digestive enzymes protects the one or more biorecognition affinity ligands immobilized to the analyte concentrator microreactor device from being digested and losing their complete structures and functionalities by proteolytic enzymes in solution. Most digestive enzymes obtained from natural sources are rarely obtained as 100% pure materials, there is always some small amount of contamination with other digestive enzymes. At less, the digestive enzymes are made artificially using biotechnological methods and further purified to homogeneity. The preservation of the immobilized affinity ligands in their active forms allows re-using the affinity ligands several times, making the system and method a cost-effective protocol. Suitable digestive enzymes include a proteolytic enzyme or protease, such as pepsin, trypsin, papain, bromelain, or kallikrein; a peptidase, such as aminopeptidase or carboxypeptidase; a nucleic acid digestive enzyme or nuclease, such as exonuclease, deoxyribonuclease, or ribonuclease; a carbohydrate digestive enzyme such as amylase, maltase, lactase, pectinase, cellulase, glucanase, or sucrase; a lipid digestive enzyme or lipase, artificial enzymes or synzymes.

The two sample collection systems of oral fluid collection system 70 and Foley catheter urine collection system 140 are merged with portable biomarker analyzer electrophoresis apparatus 10 and portable biomarker analyzer device 190 and portable integrated multidisciplinary biomarker analyzer system 400 shown in FIGS. 1, 2, 3 and 7, to form a single operating unit, but working sequentially, independently, and alternatively as separated sample collection modules. The same framework designed to collected biomarkers from urine and breath and oral specimens, can be used also to analyze biomarkers present in a dialysate fluid obtained from blood utilizing a continuous intravenous microdialysis blood sampling system with a flexible microdialysis probe and coupled to an analytical separation system. A minimally invasive microdialysis probe sample collection technique allows the measurement of multiple compounds of various molecular sizes in the dialysate. The size-selected biomarkers can be obtained by the use of semi-permeable membranes positioned at the tip of the microdialysis probe having different molecular cut-off as shown in FIG. 8.

Independently and sequentially collected exhaled breath and oral fluid collected from oral fluid collection system 70 and urine collected from Foley catheter urine collection system 140 are transported through passages or capillaries 22 and 20 all the way to outlet end 183 to trap or waste collecting system 182 with the aid of a controlled smooth vacuum using vacuum pump 186. The vacuum aspiration system of the present invention provides for freely and smooth passing of urine and exhaled breath and oral fluids through analyte concentrator-microreactor (ACM) device 42 with the purpose to capture selectively and specifically a panel of biomarkers for acquiring rapidly and effectively a comprehensive, accurate, and reliable diagnosis and prognosis molecular signature profile for measuring the severity of an ill individual 78, ideally before any symptom is manifested. When samples are passing through analyte concentrator-microreactor (ACM) device 42, constituents of the breath, oral fluid or urine can selectively and specifically be captured by one or more immobilized biorecognition molecules or affinity ligands 44, 46, 48 directed to different epitopes of the same biomolecule or to different biomolecules. The number of biorecognition affinity ligands immobilized to ACM device 42 can be more than the three illustrated in the figure, or additional ACM devices can be placed in staggered configuration as described in U.S. Pat. Nos. 7,329,388; 9,146,234; 9,696,299; 10,408,789 and shown in FIG. 7.

Once the target analytes present in the exhaled breath, oral fluid or urine specimens have been captured by the biorecognition affinity ligands immobilized to the analyte concentrator-microreactor (ACM) device 42, a process of elution and separation starts from inlet side 51 of separation passage or capillary 52. Container 54 with cap 56 can be removably replaced and used as an individual source for a separate buffer or solution, or an elution buffer or solution containing a chromophore, or a separation buffer. Tube 58 has a double function, it can be used as a guide for a platinum-iridium electrode connected to a high-voltage power supply with positive or negative polarity, and also a guide to introduce preferentially an inert gas, such as argon or helium, to create pressure for introduction of a plug of elution buffer alone or with a chromophore, and a separation buffer. Four options can be applied to the introduction of buffers or solutions: electrical motion, electroosmotic motion, mechanical pressure motion created by the inert gas, and motion by a combination of electroosmotic flow and mechanical pressure. At outlet side 53 of separation passage or capillary 52 is positioned another platinum-iridium electrode or grounding electrode, serving as the ground or earth side to complete the electrical circuit and for safety reasons. Also, at outlet side 53 of separation passage or capillary 52 are positioned, for detection, quantification and characterization, one or more on-line and/or off-line detectors, including UV-Vis absorption spectrometric, fluorescence, amperometric, contactless conductivity, electrochemiluminescence, radiometric, circular dichroism, nuclear magnetic resonance, and mass spectrometry.

When the entire sequential cycle process of capture of target analytes, cleaning, washing, elution, separation and detection is finished, transport passage or capillary 20 and separation passage or capillary 52 can be cleaned and conditioned from container 16 with cap 18 containing either cleaning, washing, and conditioning buffers or solutions and transported through transport passage or capillary 20 all the way to outlet end 183 to trap or waste container 182 with suction provided by vacuum pump 186. Container 16 with cap 18 can also be an alternative as a source of a solution containing a tagging or chromophore agent or substance or protecting separation passage of capillary 52 from non-specific binding to an inner surface of separation passage or capillary 52 of an excess amount of chromophore. The introduction of a chromophore from container 16 through transport passage or capillary 20 can interact and derivatize the bound target analytes to analyte concentrator-microreactor (ACM) device 42. Once derivatization occurs, a cleaning buffer can be transported through transport passage or capillary 20 to remove excess amount of chromophore in transport passage or capillary 20 and in analyte concentrator-microreactor (ACM) device. After the cleaning process, the protocol of sample elution and separation is started, followed by detection, quantification, and characterization as described above.

The synchronization of the sequential use of the valves is performed according to the following steps: 1) cleaning, washing and optimization of transport passage or capillary 20 and separation passage or capillary 52. A cleaning buffer or solution has a mild chemical constitution with low concentration of detergent and neutral pH, while a washing solution is much stronger and can have higher concentrations of detergents and some higher or lower pH conditions. Both of these buffers or solutions are applied for a short period of time, by mechanical pressure generated by the inert gas applied to the containers or 16 or 54 or by controlled vacuum provided by vacuum pump 186, in order to avoid any structural damage and loss of functionality to the biorecognition affinity ligands immobilized to the ACM device 42. To accomplish the passage of buffers or solutions through the transport passage or capillary 20 from inlet side 21 positioned in container 16 to the outlet side 23, valves 32, 36, and 38 and closed and valves 30, 34, and 40 are open. To accomplish the passage of buffers or solutions through the separation passage or capillary 52 from inlet side 51 positioned in container or vessel 54 to outlet side 53, valves 34 and 40 are closed and valves 60, 38, and 36 are open; 2) after the transport passage or capillary 20 and separation passage or capillary 52 are washed and/or cleaned, a conditioning buffer, which provides all the necessary ingredients and optimal conditions to protect and enhance binding activity of the biorecognition affinity ligands immobilized to analyte concentrator-microreactor (ACM) device 42, is passed through transport passage or capillary 20 and separation transport passage or capillary 52 following the same protocol described in step 1; 3) To activate the exhaled breath and oral fluid collection system 70, valves 174, 30, 36, and 38 are closed and valves 103, 106, 32, 34, and 40 are open, in order to smoothly move the fluid through the transport passages or capillaries 20, 22, 92 and 180 or tubing 72 from the adapter or connector—74 in mouth 76 of individual 78 all the way to outlet end 183 into trap or waste container 182 by smooth and controlled vacuum suction provided by vacuum pump 186. The suction is performed slowly to allow the constituents of the fluid, or target analytes, to interact under optimal binding interaction conditions with the biorecognition affinity ligands immobilized to analyte concentrator-microreactor (ACM) device 42. After this procedure is finished, valve 32, 36, and 38 are closed, then valves 30, 34, and 40 are open to allow for the cleaning buffer or solution to pass through transport passage capillary 20 to remove excess amount of salts or unwanted materials non-specifically bound to the inner wall of the transport passage or capillary 20 and analyte concentrator-microreactor (ACM) device 42. Once the analyte concentrator-microreactor (ACM) device 42 is saturated with the one or more target analytes and the system is clean, a separation buffer is introduced into separation passage or capillary 52 and the process of elution and separation starts as described above. For the elution and separation process valves 34 and 40 are closed and valves 36, 38 and 60 are open; 4) To activate Foley catheter urine collection system 140, valves 264, 106, 30, 36, and 38 are closed and valves 160, 172, 174, 32, 34, and 40 are open. The rest of the procedure is identical to the one described for the collection of exhaled breath and oral fluid, including the isolation, concentration, derivatization (if needed), detection, quantification and characterization of target analytes present in the urine; 5) A protocol for cleaning adapters or connectors 24, 176 and 178 is carried out by closing valves 101, 160, 30, 36, and 38 and to open valves 103, 106, 172, 174, 32, 34, and 40. Cleaning and/or washing buffers or solutions stored in liquid containers or vessels 110 and 170 are passed through transport passages or capillaries 92, 180, 22, and 20 all the way to trap or waste container 182, with the aid of vacuum pump 186 using mild and controlled suction; 6) Once the entire protocol has been finished a regeneration of all passages, tubes, and capillaries is performed as described in step 1. The reuse of the entire system is possible for several analyses if the biorecognition affinity ligands immobilized to the analyte concentrator-microreactor (ACM) device 42 are in full capacity of binding, and the filters in operation are not clogged.

Diagnosis tests play a crucial role in the management of health and disease. Accuracy of a diagnostic is the most vital parameter to obtain a precise and reliable diagnosis, free of false-positive or false negative results. An erroneous result can lead to a wrong diagnosis, wrong prognosis, and wrong therapy that can result in severe damage to a patient and even death. In clinical terms, accuracy can be determined through the evaluation of specificity and sensitivity. A very specific test would provide negative results for all (or almost all) patients who are disease free, and a very sensitive test would identify all (or almost all) patients who have the disease. However, from an analytical point of view accuracy is defined as the closeness of a result to the true value and is commonly obtained by the mean value of several repeated measurements. Precision expresses the degree of reproducibility or agreement between repeated measurements. In the present invention, it is possible to use one or more biorecognition affinity ligands immobilized to analyte concentrator-microreactor (ACM) device 42 to target one or more known substances, and use them as internal standards to evaluate many times that analyte concentrator-microreactor (ACM) device 42 attains reproducible results, to correct for migration times of the separated analytes, to determine the maximum capacity of capturing the known target analyte, and the effect of the constituents of the buffers and solutions in the capture, elution, derivatization and separation of target analytes present in a sample. It is also possible to use, in addition to the one or more internal standards, one or two external standards incorporated in the elution buffer or solution. The purpose of adding internal and/or external standards is to monitor the entire process of reproducibility of the protocol, as a quality control to obtain results of one or more target analytes present a sample of interest with the highest accuracy, sensitivity, specificity and reliability possible, avoiding false positive and/or false negative information.

Analyte concentrator-microreactor (ACM) device 42 can also be used as microreactor where a chemical or biochemical reaction can occur, such as the immobilization to its inner surface of proteases to digest proteins into peptides. A tandem of analyte concentrator-microreactor (ACM) device 42 as a microreactor with an analyte concentrator-microreactor (ACM) device 42 as a concentrator can facilitate the analysis of peptides biomarkers in biosamples. Microreactors can harbor specialized cells, simulating an entire piece of an organ or creating an artificial organ (organ tissue equivalents from any organism source), to study microorganism infection on cells, the effect of drugs on the infection, predicting bioavailability of the drug, pharmacokinetic and pharmacodynamic studies, drug efficacy and toxicity, without have to involve animals in the process. Multiple analyte concentrator-microreactor (ACM) devices 42 in tandem, each containing a different organoid can generate a "body" system to study the metabolites of a single pharmaceutical drug from a single biological sample from an animal or organism.

Figure 3:
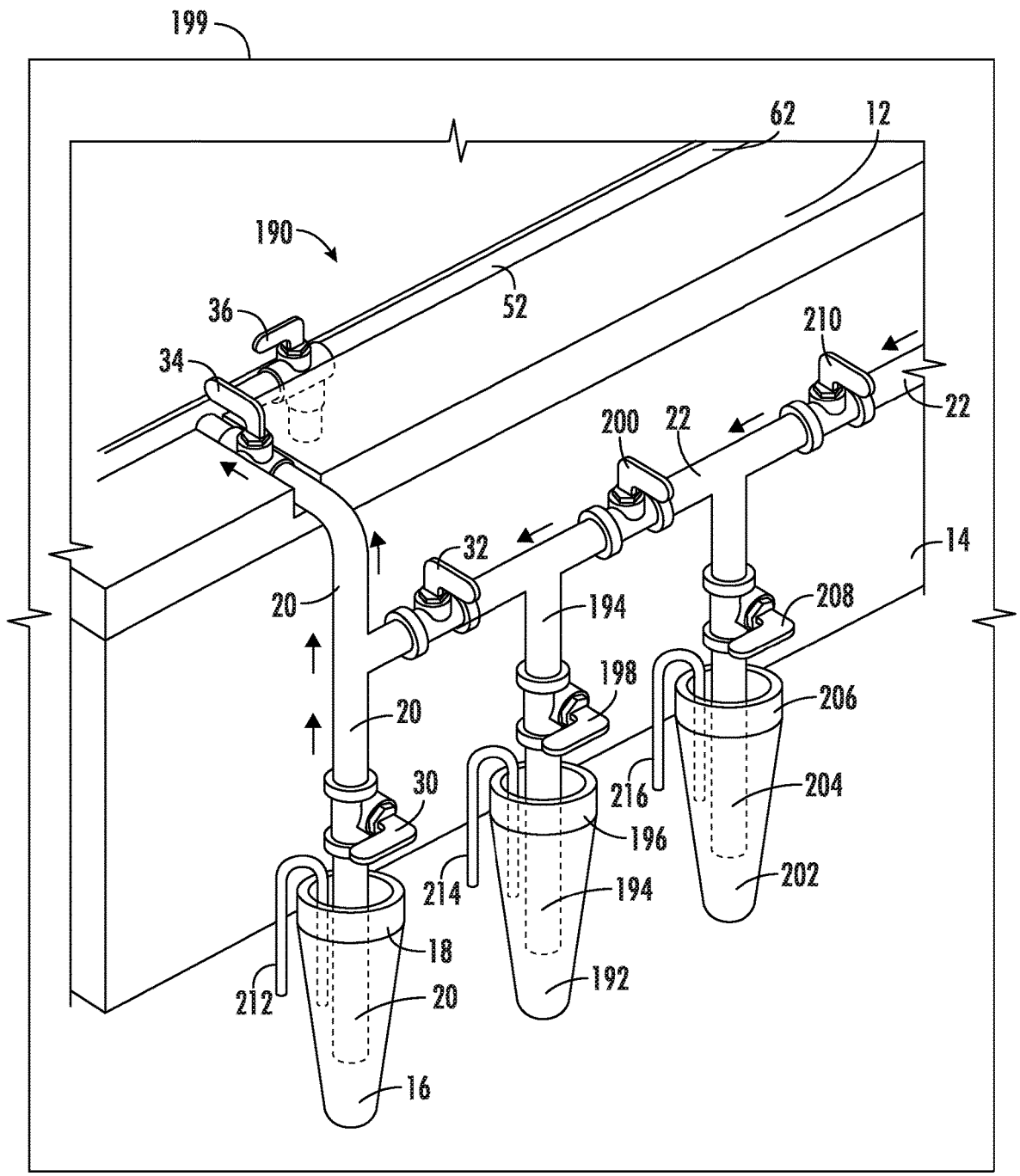
FIG. 3 is an enlarged perspective view of a container or reservoir sampling system where two or more containers are positioned in parallel and each container separately and independently carries a different chemical composition buffer or solution and they operate separately and independently in coordination with the transport passage or capillary.

FIG. 3 illustrates an enlarged perspective view of a portion of a portable biomarker analyzer device 190 showing a container or reservoir sampling system where fluid containers or vessels 16, 192, and 202 are positioned in parallel and each container separately and independently carry a different chemical composition buffer or solution and they operate separately and independently in coordination with the transport passages or capillaries 20 and 22.

One of the main goals of using portable biomarker analyzer device 190, coupled to portable exhaled breath and oral fluid collection system 70, and also coupled to portable Foley catheter urine collection system 140, as shown in FIG. 2, is for the purpose of assaying a panel of biomarkers derived from the urine and from the exhaled breath/oral fluid obtained from individual 78 who is suffering of a contagious infectious disease and is kept in an isolation unit or ward of a hospital or clinic, or potentially staying at home under the supervision of a healthcare professional. A number of conditions or forms of isolation procedures must be implemented in a healthcare facility where a patient with contagious disease is kept in an attempt to reduce the spread of healthcare associated infections, such as contact with blood, other body fluids, or secretions and excretions.

The portable biomarker analyzer device 190 can be placed near to individual 78, portable exhaled breath and oral fluid collection system 70, and portable Foley catheter urine collection system 140, as shown in FIG. 2, within biosafety container 199 as shown in FIG. 3. Biosafety container 199 can be transparent. Since the portable biomarker analyzer device 190 is a portable miniaturized instrument, not much space is needed for maintaining the device in a containment area. Precautions for a possible failure of each modular component of portable biomarker analyzer device 190 can be implemented. For example, fluid containers or vessels 16, 192, and 202 with container caps 18, 196 and 206 can be filled with cleaning, washing, and conditioning buffers or solutions. When used, containers or vessels 16, 192, and 202 can be filled again with their respective buffers or solutions using tubes 212, 214, and 216 respectively. With respect to micro-valves 30, 32, 34, 36, 198, 200, 208, and 210 they can be operated by a separate and independent computer-controlled system in case one of the two switch on-off mechanisms to operate each valve fails. Similar micro-valve operating double-control system can be used for individually computer controlled micro-valves 38, 40, 60, 101, 103, 106, 160, 172, and 174 shown in FIG. 2. Adapters or connectors 24, 176, and 178 shown in FIG. 2 can be multi-layer porous filters for filtration and can be tailored with different network porosities controlling structure-composition can be of significant aid in retaining larger aggregates but permitting a smooth passing of certain cells, subcellular structures, viruses and exosomes. Furthermore, with the aid of digestive enzymes that can be immobilized to inner walls of angle connector 150 and adapter or connector 164 and adapter or connector 180, as shown in FIG. 2, many large aggregates and large biomolecules can be broken down to smaller molecules and be captured by a biorecognition affinity ligand immobilized at analyte concentrator-microreactor (ACM) device 42. Avoiding clogging of the various passages and capillaries can also be accomplished by the use of a microwave or acoustic micromixing system, which in addition to be used in the area of analyte concentrator-microreactor (ACM) device 42 to improve the efficiency of the binding process and the speeding of the binding process to occur in a short period of time, it can also be positioned along the various passages and capillaries near the multi-layer filter-sieving network to remove molecular agglomeration and cell debris. The combination of immobilized proteolytic digestion, with motion of fluids generated by controlled microwave and/or acoustic waves or pulses, and the continuing and controlled suction by the use of a vacuum pump help significantly fluid motion and oscillation, biomolecule solubility, and smooth transport of biomolecules through the transport passages, tubing, or capillaries.

Figure 7:
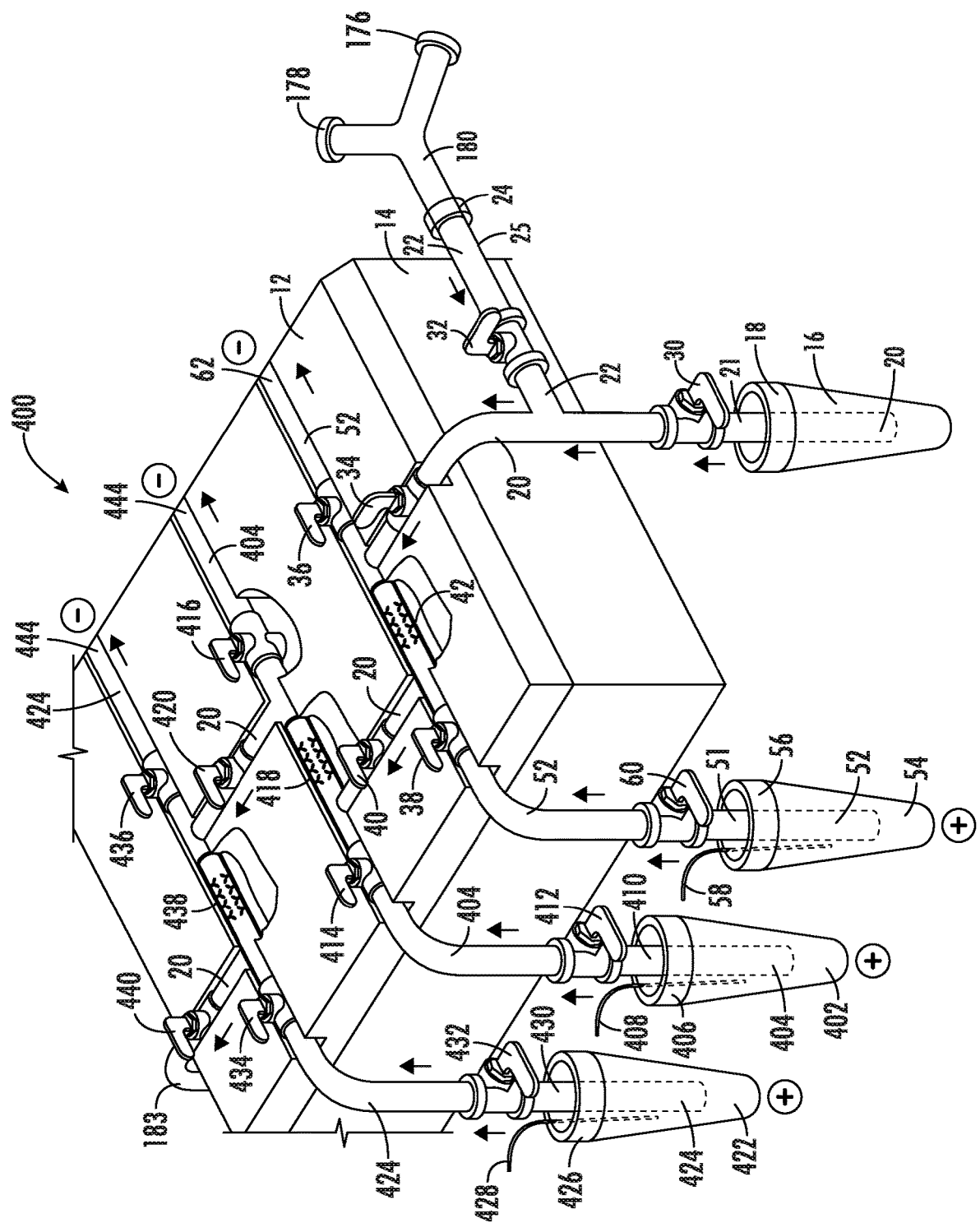
FIG. 7 is a diagrammatic perspective view that illustrates an embodiment of the portable biomarker analyzer electrophoresis apparatus including multiple analyte concentrator-microreactor (ACM) devices, each with the corresponding separation passages or capillaries and their respective containers or vessels, and an auxiliary transport passage or capillary with a terminal connector or coupler to connect to external sample collection systems.
Figure 8:
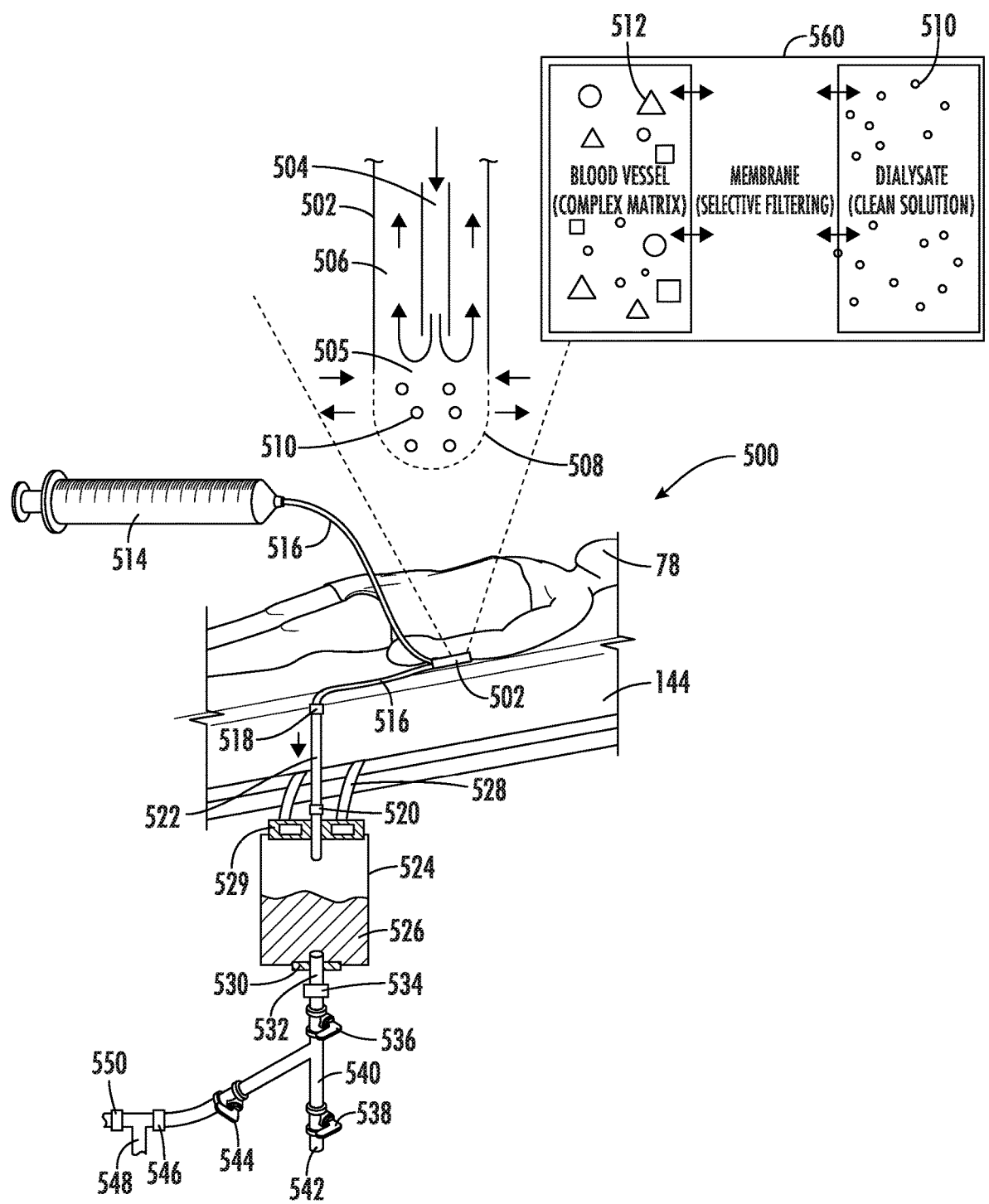
FIG. 8 is a diagrammatic perspective view that illustrates an intravenous collection system to collect a blood dialysate from an individual using a flexible microdialysis probe inserted into a blood vessel, and the dialysate drained into a collection container to be connected to a portable biomarker analyzer electrophoresis instrument for analysis.

Portable point-of-care IACE biomarker analyzer instrument shown in FIG. 1 can include two or more analyte concentrator-microreactor (ACM) devices 42 positioned in separation passage or capillary 52, or in a separate separation passage or capillary, as shown in FIG. 7. Plurality of analyte concentrator-microreactor (ACM) devices can be used as separate and independent controlled microenvironments having different immobilized biorecognition affinity ligands to capture a panel of biomarkers, including biomolecular and particle entities. Comprehensive information can be obtained from a panel of biomarkers present in biological fluids and assayed in a single platform.

Portable biomarker analyzer electrophoresis apparatus 10 and portable biomarker analyzer device 190 shown in FIGS. 1, 2, and 3, in conjunction with Foley catheter urine collection system 140 and exhaled breath and oral fluid collection system 70 and the minimally invasive microdialysis probe sample collection technique, as shown in FIG. 8, can serve as a single modular platform to determine a comprehensive panel of different types of biomarkers to make possible the diagnosis and prognosis of a disease accurately, consistently, and reliable at the earlier stages of its formation, a continuous monitoring throughout the evolution of the disease, and maintaining a regular surveillance of the effectiveness of the therapy.

Figure 4:
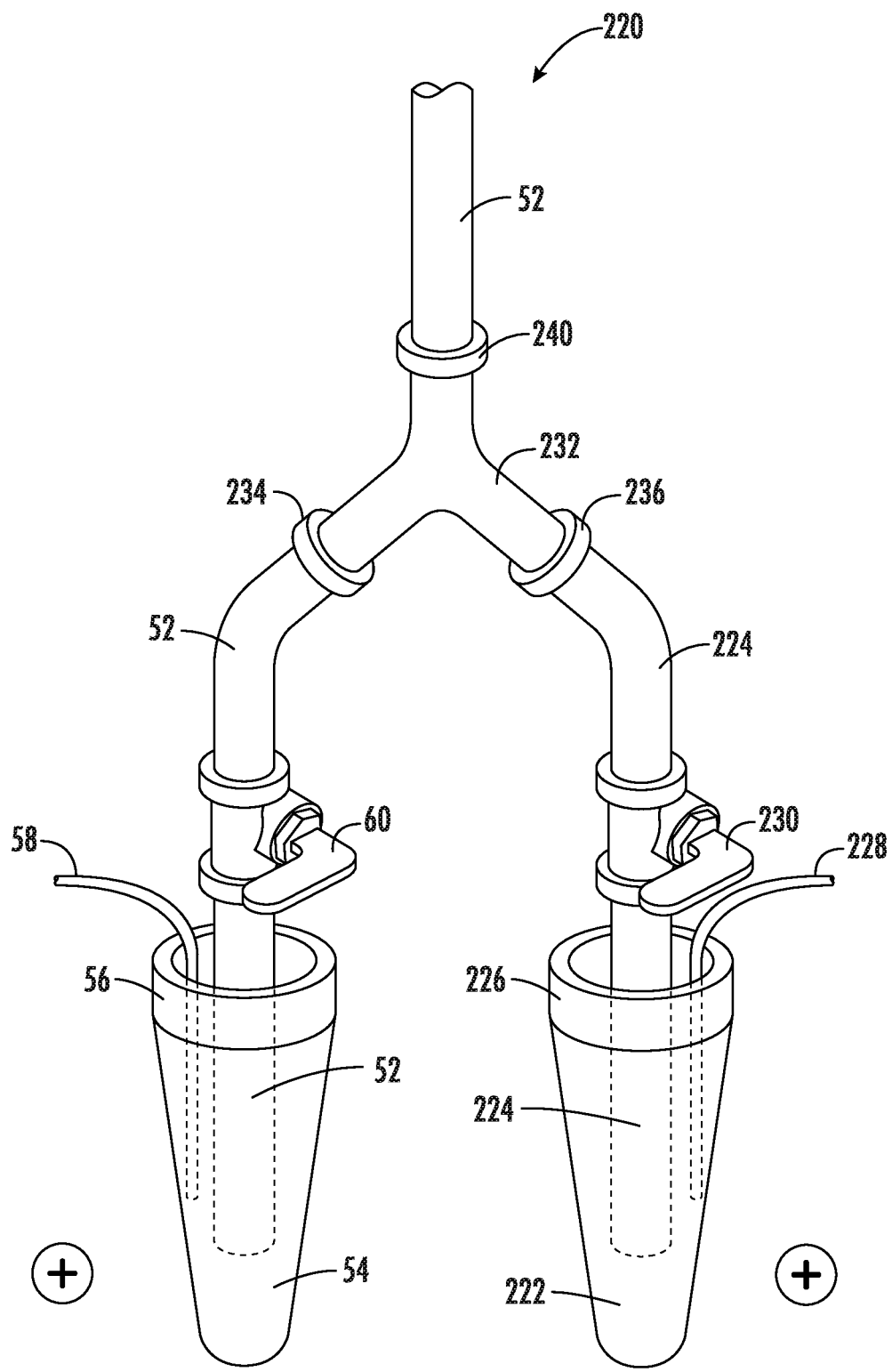
FIG. 4 is an enlarged perspective view of a container or reservoir sampling system where two containers are positioned in parallel and each container separately and independently carries a different chemical composition buffer or solution and they operate separately and independently in coordination with the separation passage or capillary. Each container has imbedded in the buffer or solution a separately and independently separation passage or capillary, which are connected by a Y-connector to form a single separation passage or capillary.

FIG. 4 illustrates container or reservoir sampling system 220 where two containers or vessels 54 and 222 are positioned in parallel and each container or separately and independently carry a different chemical composition buffer or solution and they operate separately and independently in coordination with separation passage or capillary 52. Container or vessel 54 with cap 56 contains an appropriate separation buffer or solution in which separation passage or capillary 52 is embedded. Container or vessel 54 with cap 56 also allows the introduction of tube 58 where an electrode composed of platinum-iridium is inserted, and where an inert gas such as helium and argon can also be introduced to create pressure to pass and move separation buffer or solution into separation passage or capillary 52. Container or vessel 54 with cap 56 form a hermetic environment to avoid any leakage of fluid and prevent the entrance of air that may form unwanted bubbles into separation passage or capillary 52. On the opposite side, is positioned container or vessel 222 with cap 226 carrying an elution buffer or solution, or an elution buffer or solution containing a chromophore tagging substance to derivative one or more captured target analytes by one or more biorecognition affinity ligands immobilized to analyte concentrator-microreactor (ACM) device 42, as shown in FIG. 2. Referring to FIG. 4, similar to container or vessel 54, container or vessel 222 with cap 226 also allows introduction of tube 228 where an electrode composed of platinum-iridium is inserted, and where an inert gas such as helium and argon can also be introduced to create pressure to pass and move elution buffer or solution into the separation passage or capillary. Container or vessel 222 with cap 226 also forms a hermetic environment to avoid any leakage of fluid and prevent the entrance of air that may form unwanted bubbles into connecting passage or capillary 224 and into the main separation passage or capillary 52. The passages or capillaries 52 and 224 embedded into containers or vessels 54 and 222, respectively, are connected to separation passage or capillary 52 by split or bifurcation tube connector 232 using adapters or connectors 234, 236, and 240. For two containers or vessels 54 and 22 to operate, they are coordinated to function independently, separately, and sequentially using valves 60 and 230 respectively, and in synchronization with the rest of the valves described in FIG. 2.

The simple and independent computer-controlled operation system of the two micro-valves 60 and 230 avoids the use of a turntable or carrousel for changing buffers or solutions from one container to another and protects possible contamination if a malfunction operation of the carrousel where to occur. Each of micro-valves 60 and 230 can work with two switch on-off mechanism to operate. The valve system can be switched on/off by adapting two micro-valve systems working in-tandem and operated by separated and independent controls. In one embodiment, two pieces of the same separation passage or capillary 52 can be connected hermetically by a plastic sleeve with approximately 1 to 3 mm of plastic sleeve connection capillary. Separation passage or capillary 52 can be formed of a plurality of plastic tubes, such as two or four plastic tubes, creating a protective layer of thicker tube diameter than a single plastic sleeve. The plurality of plastic tubes can be placed one on top of the other with their respective diameters to fit. A pressing pinch valve can put enough pressure on the connecting plastic sleeve that it will disrupt the passage of fluid, without altering or damaging the connecting plastic sleeve. When the pressure generated by the plastic sleeve is removed, then the connection will be re-established to allow the passage of fluid again. Because two pressing bars serving as pinch valves can be installed to press the multi-layer tubes, each micro-valve 60 and 230 can then be operated separately and independently and activated by a computer-controlled system. A similar micro-valve operating double-control system can be used for individually computer controlled micro-valves 30, 32, 38, 40, 60, 101, 103, 106, 160, 172, 174, and 264 as shown in FIG. 2.

Hermetically sealed isolation chambers to place a patient affected by an infectious disease may have profound negative psychological effects on the patient, but to place in a small hermetically sealed chamber a portable miniaturized point-of-care instrument or device to assess the progress of a patient's health on continuous basis, can be of significant advantage to the patient and to the caregivers personnel working with the patient, without affecting the mental health of the patient. Rapid turn-around and communication of accurate results is critical to guide clinical decisions and follow-up action, in particular in providing continuous information for a better care. FIG. 4, as well as FIG. 2 and FIG. 3, depict the portable biomarker analyzer electrophoresis apparatus 10 and portable biomarker analyzer devices 190, which are portable and miniaturized and have the capabilities to provide a comprehensive panel of biomarkers for patient suffering of an infectious disease, under protective free-contagious operating conditions. Portable biomarker analyzer electrophoresis apparatus 10 and portable biomarker analyzer device 190 shown in FIG. 2 and FIG. 3 have benefits in resources-limited setting, and comprehensive data information can be shared with larger medical institutions with aid of telemedicine connecting the instrument information with data management system.

Figure 5:
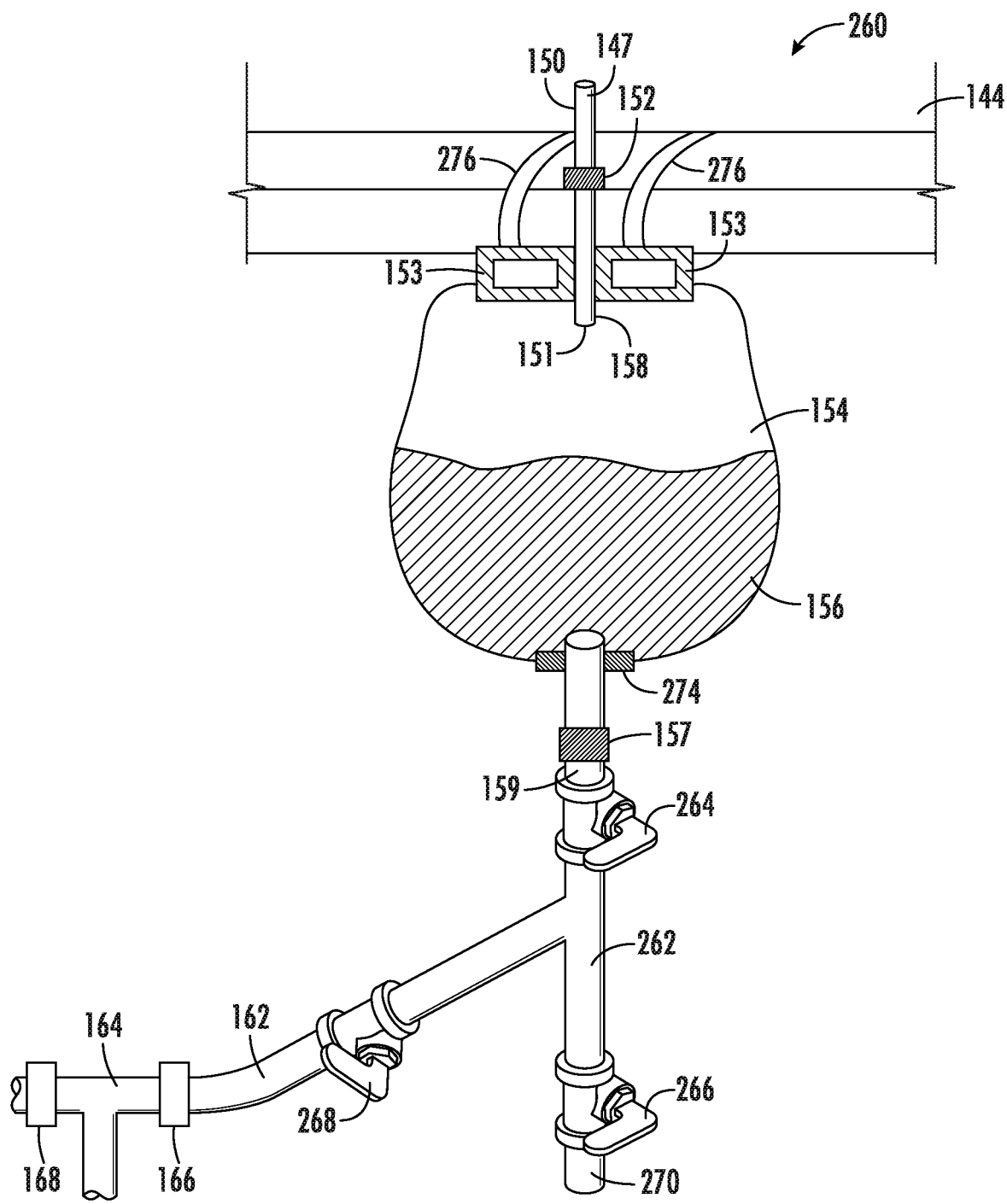
FIG. 5 is an enlarged perspective view of a coupling or attachment system that is connected to a container, reservoir or drainage bag connected to a Foley catheter.

FIG. 5 illustrates urine collection system 260 comprising urine collection bag 154 coupled to Foley catheter 146 that serves as a reservoir or drainage for urine 156 obtained from the bladder of individual 78 as shown in FIG. 2. Urine collecting bags coupled to a Foley catheter collection system are normally used for the elimination of the urine produced by an individual. Urine collection bag or reservoir 154 is used not only to collect and eliminate urine 156 out of the bag it is also used to take a portion of urine 156 and to assay for the presence of biomarkers in the urine and be able to monitor the health condition of an individual on a continuous basis, for example every one or two hours, as the urine is drained out of the bladder of an individual. Urine collection bag or reservoir 154 can be formed of a resistant plastic and is connected with support or holder device 153 to be positioned on side of bed 144, a wheelchair or to the leg of the and individual or patient 78 (shown in FIG. 2) to hold weight of the bag for a collected volume of urine.

FIG. 5 shows a portion of angle connector 150 coupled to tube 158 using adapters or connectors 148 and 152, as shown in FIG. 2. The inner surface of straight tube portion 147 of angle connector 150 or the entire inner surface of angle connector 150 can be coated with digestive enzymes with the purpose of breaking down larger biopolymers present in the urine to smaller molecular entities, as well as the digestion of entire particle entities or granular materials. The digestion of portion of structural components of bacteria or other particle entities, or entire cellular entities such as blood cells, bacteria, subcellular entities, viruses, and exosomes, can provide potential signature biomarkers for specific identification of bacteria, viruses, and exosomes. The resulting digestive products derived from larger biopolymers, such as peptides, oligonucleotides, small glycan and lipid substances, or products derived from exosomes can provide additional biomarkers of a clinical condition of the patient due to an alteration of an enzymatic pathway, or an organ failure, or trauma. The digestive products of bacteria, viruses or other microorganisms can provide biomarkers of an infectious disease process and also be a unique recognition identification characteristic for each microorganism. A panel of biomarkers that can be obtained using portable biomarker analyzer electrophoresis apparatus 10 and portable biomarker analyzer device 190 as shown in FIGS. 1, 2, and 3 can provide comprehensive information about the type of disease affecting a patient, the evolution and state of severity of the disease, and the effect of therapy. In the case of an infectious disease, the biomarkers can provide information about the type of microorganism affecting an individual, the response of the body by producing antibodies, inflammatory substances, connective tissue related substances and many others, and also to aid and guide the rational use of antibiotics or antiviral therapies.

FIG. 5 also shows additional digestive embodiments using immobilized digestive enzymes to obtain signature biomarkers for the identification of microorganisms and/or signature biomarkers generated by the response of the body to the attacks by microorganisms. Tube 159 can be hermetically sealed to urine collection bag or reservoir 154 and reinforced by support system 274. Tube 159 can be connected to tube 270 to drain urine 156 out of urine collection bag or reservoir 154 using splitter tube 262. Micro-valve 264 is positioned between tube 159 and splitter tube 262. Micro-valve 266 is positioned between tube 270 and splitter tube 262. Micro-valve 268 is positioned between transport passage or capillary 162 and splitter tube 262. Tube 159 containing filter 157 and positioned adjacent to micro-valve 264 can have large porosity and also contain digestive enzymes immobilized to a surface matrix forming the filter. Additionally, splitter tube 262 and adapter or connector 164 can have digestive enzymes immobilized to their inner surfaces. Adapter or connector 164 can be a T-shaped tube. Adapter or connector 164 is connected to transport passage or capillary 162 by adapter or connector 166. The continuing digestion of large biomolecular entities, aggregated particles, and granular materials allows the generation of small molecules as source of potential biomarkers, and contribute to the maintenance of a clogging-free system for moving the sample smoothly by way of the transport passages, or capillaries 162, 180, 22, and 20, as shown in FIG. 2, from the sample collection points of exhaled breath and oral fluid collection system 70 and Foley catheter urine collection system 140, passing through analyte concentrator-microreactor (ACM) device 42 positioned in separation passage or capillary 52, all the way to trap or waste container 182. The combination of a urine collection system coupled to a two-dimensional capture-separation technology point-of-care instrument or device provides improved technological advantages for obtaining a panel of biomarkers. A Multibiomarker panel signature is advantageous and crucial for an early and accurate diagnosis and prognosis. A combination of host biomarkers with viral antigen detection, in an infectious disease, can provide valuable in clinical care to optimize therapeutic decision making and may exclude bacterial co-infection, avoiding the use of inappropriate microbial therapy Clinical practice relies on the use of specific biological parameters or biomarkers which can be correlated with the onset, establishment, development and therapeutic response of diseases. It is advantageous that the source of the biomarkers is from non-invasive sampling, such as exhaled breath, saliva and urine specimens, allowing for frequency of biomarkers testing using cost-effective diagnostic technologies.

Figure 6:
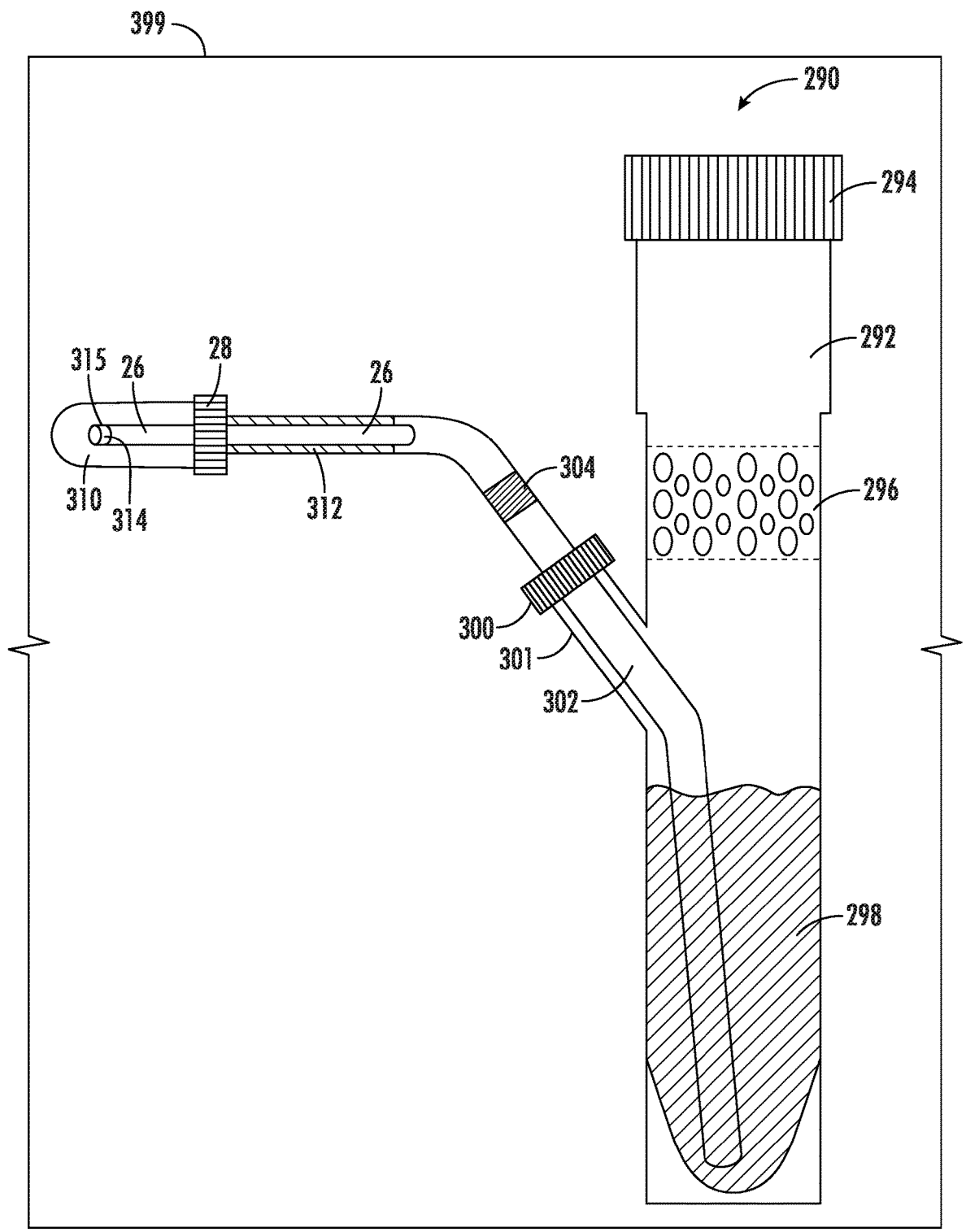
FIG. 6 is an enlarged perspective view of a container or vessel to collect and transport a biological fluid having safety and protected snap-on caps to avoid leakage and contamination and containing a coupler or adapter to be coupled to an analytical separation instrument.

FIG. 6 illustrates sampling collection system 290 comprising a container or vessel 292 with side arm 301 to collect and transport a biological fluid or specimen 298. Container or vessel 292 can have safety and protected snap-on caps 294 and 300 to avoid leakage and contamination of collected specimen 298. Sampling collecting system 290 can be used to collect and transport primarily mouth or oral fluid and urine specimens. As specimen 298 is collected, it is passed through filter 296 to retain conglomerated material that can be obtained from the whole mouth fluid or urine specimens respectively in filter 296. Human whole mouth, oral or buccal fluid is a broad term which include saliva, gingival crevicular fluids, oral mucosa transudate, mucus secretions from the nasal cavity and the pharynx, serous secretions, expectorated bronchial and nasal secretions, exosomes, viruses, bacteria, as well as products resulting from bacterial metabolism, food debris, and desquamated epithelial cells and is a source of nucleic acids, proteins, peptides, metabolites and other biomolecules (S. P. Humphrey, R. T. Williamson. The Journal of Prosthetic Dentistry, volume 85, pages 162-169, 2001). Urine is also a source of all of these biomolecules, and in addition it may have some epithelial cells, non-epithelial cells (blood cells), casts from aggregation of proteins, clamping of cell together, salts/crystals, microorganisms, as well as products resulting from bacterial metabolism, exosomes, bacteria, viruses, and some small amount of mucus. Urine and saliva are not completely sterile specimens, they can get contaminated with small amounts of microorganisms, even if a person does not have an infection. The stability of some biomarkers present in the collected oral fluid, saliva or urine may be affected by the change in pH. The presence of certain preservatives can aid to maintain acidic pH, such as boric acid or acetic acid. Other preservatives, such as bicarbonate salts or sodium hydroxide may provide a more alkaline pH.

Filtration of mouth or oral fluid and urine is advantageous to remove unwanted aggregated materials and/or cellular clamps to obtain a clean biological fluid for further analysis using the portable biomarker analyzer electrophoresis apparatus 10 and portable biomarker analyzer device 190 as shown in FIGS. 1, 2, and 3. The target analytes are biomolecules and smaller particles such as virus and exosomes, as well as products resulting from bacterial metabolism from normal microbiota or an infection. Referring to FIG. 6, Two filters, 296 and 304, are used in sample collection system 290 to retain unwanted materials such as larger aggregates. Filters 296 and 304, in addition to be selective for the process of filtration, can include digestive enzymes immobilized to a matrix forming the filter, which aid in the breakdown of larger biomolecules into simple and smaller biomolecules. Cap 300 can hermetically seal support 312 to flexible tube 302.

Once specimen 298 is collected in container or vessel 292 with hermetically sealed caps 28, 294, and 300 it is ready for transport to portable biomarker analyzer 10 as shown in FIG. 1. Cap 300 can serve also as a coupler adapter where flexible tube 302 can be inserted into container or vessel 292, all the way to the bottom of container or vessel 292, to be in contact with specimen 298. Flexible tube 302 has an additional selective filter 304, also with digestive enzymes immobilized to the matrix of the membrane. Coupling tube 26 can be within flexible tube 302. Coupling tube 26 is of a smaller diameter than flexible tube 302. Coupling tube 26 connects sampling collection system 290 with portable biomarker analyzer 10 shown in FIG. 1. Coupling tube 26 is firmly secured and hermetically sealed by support 312 within flexible tube 302, permitting only the passage of the collected biological specimen, such as urine or saliva, through coupling tube 26. Outlet end 315 of coupling tube 26 has cap 314 avoiding escaping of the collected biological fluid from sampling collection system 290. External protection tube 310 is coupled to cap 28. External protection tube 310 can aid in transportation of sampling connection system 290. Cap 28 can also be used as an adapter or connector.

Transportation box, 399 can be positioned around sampling collection system 290. Transportation box 399 provides protection against outside influences during shipping and can be made lightweight and impact resistant.

Sampling collection system 290 can be coupled to portable biomarker analyzer 10 shown in FIG. 1, by removing protection tube 310 and protective cap 314, shown in FIGS. 1 and 7, and connecting to transport passage or capillary 22 of portable biomarker analyzer device 10, with couplers or adapters 24 and 28 to create a sealed and hermetic connection, as shown in FIG. 1. Analyte concentrator-microreactor (ACM) 42 can be manufactured as a detachable and replaceable embodiment and can be shipped to and from a remote area in transportation box 399, facilitating sample collection and transportation under appropriate and safe conditions. Sealed inlet and outlet end or Snap-on tube caps as shown in FIG. 6 can provide protection to avoid the leakage of optimized fluid for transportation, and can preserve the integrity and stability of the immobilized affinity ligands and the target analytes to be analyzed, allowing to survive shipping and also to provide a safe enclosure to avoid contamination or infection to handlers.

FIG. 7 illustrates an embodiment comprising portable integrated multidisciplinary biomarker analyzer system 400 which includes three analyte concentrator-microreactor (ACM) devices 42, 418, and 438, each respectively connected to corresponding separation passages or capillaries 52, 404, and 424, and to transport passage or capillary 20. Transport passage or capillary 22 is connected to main transport passage 20 and also to adapter or connector 180 to attach external collection systems capable of providing diverse types of biological fluid specimens for analysis. Transport passage or capillary 20 can be a main transport passage or capillary and transport passage or capillary 22 can be a secondary or auxiliary transport passage or capillary. Terminal splitter adapter or connector 180 can be a splitter having two adapters or connectors 176 and 178 serving as a connection points for sample collection systems, such as portable exhaled breath and oral fluid collection system 70 and Foley catheter urine collection system 140 shown in FIG. 2, or intravenous microdialysis blood collection system shown in FIG. 8.

Transport passage or capillary 20, transport passage or capillary 22, and separation passages or capillaries 52, 404, and 424, along with the valving system that directs the flow of fluid along a desired path through transport passages or capillaries 20 and 22 and separation passages or capillaries 52, 404, and 424 can be incorporated into platform 12 of portable integrated multidisciplinary biomarker analyzer system 400 in a variety of ways. The valving system comprising microvalves 30, 32, 34, 36, 38, 40, 60, 412, 414, 416, 420, 432, 434, 436, and 440 can work in a synchronized manner manually or controlled by computer.

Each of analyte concentrator-microreactor (ACM) devices 42, 418, and 438 can have more than one biorecognition affinity ligand to capture different target analytes present in a single biological sample. Once the different target analytes are captured by the analyte concentrator-microreactor (ACM) devices 42, 418, and 438, followed by a cleaning buffer or solution, the elution process to release the different target analytes from each corresponding analyte concentrator-microreactor (ACM) device 42, 418 and 438 is performed independently and sequentially until the separation, detection, quantification and characterization have been completed. Conversely, analyte concentrator-microreactor ACM devices 42, 418 and 438 can have more than one biorecognition affinity ligand to capture one single target analyte present in a sample. For example, if there are three biorecognition affinity ligands immobilized to analyte concentrator-microreactor (ACM) device 42 aimed at three different epitopes of target analyte-A, then only target analyte-A will be captured from a biological sample under study. Similarly, if analyte concentrator-microreactor (ACM) device 418 has three biorecognition affinity ligands aimed to capture target analyte-B present in the same biological fluid, then only analyte-B will be captured by analyte concentrator-microreactor (ACM) device 418. Similarly, if analyte concentrator-microreactor (ACM) device 438 has three biorecognition affinity ligands aimed to capture target analyte-C present in the same biological fluid, then only analyte-C will be captured by analyte concentrator-microreactor (ACM) device 438. It is also possible, because of polyreactivity with each of the biorecognition affinity ligands, some closely structurally related target analytes can be captured at each of the analyte concentrator-microreactor (ACM) devices 42, 418 and 438. Once the different target analytes are captured by analyte concentrator-microreactor (ACM) devices 42, 418, and 438, followed by a cleaning buffer or solution, the elution process to release the different target analytes from each corresponding analyte concentrator-microreactor (ACM) devices 42, 418 and 438 is performed independently and sequentially until the separation, detection, quantification and characterization have been completed. The process of release of the bound target analytes to analyte concentrator-microreactor (ACM) devices 42, 418 and 438 can be made as a stepwise elution, in which the composition of the elution buffer or solution is changed in steps. Conversely, the release of the bound target analytes can be isocratic at a one-step elution using a higher concentration of eluent material or composition of the elution buffer or solution.

The steps to proceed if the sample is introduced from container 16 are performed by closing and opening corresponding microvalves. Microvalves 32, 36, 38, 414, 416, 434, and 436 will be closed, and microvalves 30, 34, 40, 420, and 440 will be open. The process of sample introduction can be performed using a controlled suction from a vacuum pump localized at outlet end 183, or by pressure provide by an inert gas, such as argon or helium, from a tubing inserted (not shown) into container 16, hermetically sealed by cap 18. After the target analytes have been captured by the corresponding biorecognition affinity ligands immobilized at inner surfaces of analyte concentrator-microreactor (ACM) devices 42, 418, and 438, a process of removing unwanted materials non-specifically bound to the inner surface of transport passage or capillary 20, and the inner surface of analyte concentrator-microreactor ACM devices 42, 418 and 438, starts from container 16 that has been replaced with a cleaning buffer or solution. The process of buffer or solution introduction into transport passage or capillary 20 is identical to the introduction of a sample under study.

Once the target analytes are bound to the corresponding biorecognition affinity ligand immobilized to analyte concentrator-microreactor (ACM) devices 42, 418, and 438, and the system has been cleaned with a cleaning buffer or solution, then microvalves 30, 32, 34, 40, 420, and 440 are closed and the elution process starts in a sequential order. First elution and separation processes are carried out at separation passage or capillary 52. For these operations, microvalves 60, 38, and 36 are open. A small amount or plug of an elution buffer or solution localized within container 54 is introduced into separation passage or capillary 52 using a pressure generated by an inert gas, such as argon or helium introduced through tube 58. Container 54 is replaced by another identical container or vessel having an appropriate separation buffer. At this point, the process of elution and separation of the released bound target analytes to analyte concentrator-microreactor (ACM) device 42 is carried out by switching on a power supply connected to a platinum-iridium electrode placed in tube 58 and immersed into separation buffer within container 54. Depending on the chemical constitution of the separation buffer and the viscosity of the separation matrix, motion of the released target analytes in the separation buffer can be carried out from inlet side 51 of container 54, all the way to outlet side 62, by electrical motion, electroosmotic flow, mechanical pressure, or a combination of electroosmotic flow and mechanical pressure. At outlet side 62 of separation passage or capillary 52 there is another container with an electrode (not shown) serving as an electrical grounding area. Also, at outlet side 62 of separation passage or capillary 52 are positioned one or more detectors for on-line, in-line, or off-line detection. The detectors can include an ultraviolet-visible detector, fluorescence, laser-induced florescence, amperometric-electrochemical, radiometric, phosphorescence, chemiluminescence, mass spectrometer, circular dichroism, or a combination of these detectors. After obtaining the information of detection, quantification, and/or partial characterization of each individual separated target analyte and their internal standards, a similar process of elution is performed for those analytes bound to analyte concentrator-microreactor (ACM) devices 418, and 438. The entire system can be washed, cleaned, and conditioned with the respective buffers or solutions and a new process can be started.

When the sample is introduced from the inlet side of transport passage or capillary 22, an identical protocol for capturing, cleaning, elution, separation, detection, quantification and partial characterization, is performed as the one described when a sample is introduced from container 16.

Portable integrated multidisciplinary biomarker analyzer system 400 has been designed as a comprehensive instrumentation solution for complex systems in a compacted miniaturized format. Additional operations can be carried out for in tandem use of analyte concentrator-microreactor (ACM) devices, serving as a microreactor and a concentrator in a coordinated fashion. For example, analyte concentrator-microreactor (ACM) 42 serving as a microreactor, can have immobilized at an inner surface one or more digestive enzymes to cleave biomolecules or large cellular or molecular entities. The resulting digested small and selective target analyte molecules can then be captured by one or more biorecognition affinity ligands immobilized to analyte concentrator-microreactor (ACM) device 418 and/or analyte concentrator-microreactor (ACM) device 438, serving as concentrators. The opening and closing of the microvalves, and the rest of the protocol to clean, elute, separate and analyze the released target analytes from analyte concentrator-microreactor (ACM) devices 418 and 438 are identical as the one described above.

There are multiple advantages when using portable integrated multidisciplinary biomarker analyzer system 400. It is portable, transportable, and it can generate a panel of biomarkers from one or more biological specimens, providing a comprehensive instrumentation solution for complex systems. Because the immobilized biorecognition affinity ligands to the ACM devices are re-usable several times, it is cost-effective, and several samples can be analyzed for a same patient during the course of 24 hours, yielding a more precise and accurate diagnosis and prognosis and monitoring the effectiveness of treatment. Portable integrated multidisciplinary biomarker analyzer system 400 uses small amounts of samples and reagents, in the order of a few microliters or milliliters. It is environmentally friendly, because of very small amounts of organic solvents used. It is easy to use, and it can be operated almost entirely by computer control. With the use of miniaturized laser-induced fluorescence detectors equipped with inexpensive and long duration light-emitting diode (LED) lamps, it is possible to achieve highly sensitive measurements of target analytes found at very small concentrations in biological fluids. Because of the two-dimensional principle of immunoaffinity capillary electrophoresis and the rigorous protocol permitting more than one type of biorecognition affinity ligand immobilized to the ACM device, the method and system of portable integrated multidisciplinary biomarker analyzer system 400, the biomarker analyzer instrument has very low probability of obtaining false positive and false negative results. Even closely structurally related molecular entities that can be captured by the immobilized biorecognition affinity ligands, can be separated and identified from the main desired target analytes and their presence can be discarded from the data evaluation, increasing significantly accuracy and reliability of the test under study.

FIG. 8 illustrates intravenous microdialysis blood collection system 500 to collect a blood dialysate from individual 78 using flexible microdialysis probe 502 inserted into a blood vessel with the guide of a needle, and dialysate 526 drained into collection container 524 to be connected to a portable integrated multidisciplinary biomarker analyzer system 99 or 400 (shown in FIGS. 2 and 7) for analysis.

Syringe 514, containing a physiological buffer, the perfusate, is slowly flushed through inflow tube 504 of microdialysis probe 502 using a syringe pump (not shown) at a controllable flow of fluid, usually at flow rates of less than about 1 microliter per minute, and can be used at a range fluctuating from about 0.3 to about 3.0 microliters per minute. Semi-permeable membrane 508 is positioned at end 505 of inflow tube 504. Semi-permeable membrane 508 acts as physical barrier, where the perfusate or perfusion fluid enter in an equilibrium with blood components crossing semi-membrane 508, forming dialysate 506 containing small molecular weight blood constituents 510. Mechanism of microdialysis 560 illustrates that large biomolecules 512, such as blood cells and bacteria, cannot cross semi-permeable membrane 508. Semi-permeable membrane 508 provides selective filtering by permitting only small molecular weight blood constituents 510 present in dialysate 506, which is usually a clean solution. Dialysate 506 exits microdialysis probe 502 through outflow tube 506 into exit tubing 516 connecting to container or vessel 524 and stored as dialysate 526. Polymer membranes with well-defined surface chemistry and pore sizes greater than 500 nanometers can be used allowing filtering through of nanoparticles of less than about 200 nanometers, a preferable condition to recover exosomes from intravenous blood dialysates. Collected dialysate 526 can be transported to splitter connector 540 and to transport passage or capillary 22 shown in FIGS. 2 and 7 for analysis of the content of the blood microdialysate using portable biomarker analyzer device 10 shown in FIG. 2. Container or vessel 524 can be attached to bed 144 where individual 78 is positioned, using holders 528 attached to support 529. Tube 522 connect to exit tubing 516 and to container or vessel 524 using adapters or couplers 518 and 520. Container or vessel 524 is connected to tube 522 attached by support 529, and to tube 532 attached by support 530. Tube 532 is connected to microvalve 536. Filter 534 can be connected to tube 532 to where digestive enzymes are immobilized to a matrix of filter 534 to digest any nanoparticles or large biomolecules that have passed through semi-permeable membrane 508, localized at the tip of the microdialysis probe, and are present in clean dialysate 506. Splitter connector 540 can also have digestive enzymes immobilized to an inner surface, used for the same purpose of digesting larger macromolecules or nanoparticles. Microvalve 536 controls flow of dialysate 526 to enter splitter connector 540. Microvalve 538 is used to exit a cleaning solution, if there is a need to clean the system after a few uses. Microvalve 544 permits the transport of dialysate 526 to transport passage or capillary 22 shown in FIGS. 2 and 7. T-shaped tube 548 is connected to liquid vessel or container 170 (shown in FIG. 2), containing a solution with detergent to maintain a smooth flow. The process of transporting the dialysate 526 all the way to trap or container 182, using a controlled suction provided by vacuum pump 186, and passing through analyte concentrator-microreactor (ACM) device 42 as shown in FIG. 2 is the same as described in FIG. 2. The analysis of the target analytes and system operation of portable biomarker analyzer electrophoresis apparatus 10 as shown in FIG. 2 is also the same as the protocol described in FIG. 2. Intravenous blood collection system 500 has the advantages that all components used in this system are miniaturized, permitting the maximum efficiency in the analysis with the minimum loss of material that are present in a small volume of dialysate.

Portable biomarker analyzer electrophoresis apparatus 10 or portable biomarker analyzer device 190 and portable integrated multidisciplinary biomarker analyzer system 99 or 400 including a central processing unit (CPU) system that executes instructions using electronic circuitry and a computer which can be combined in an artificial intelligence system can be used in conjunction with telemedicine in remote places. The CPU system can include a memory having reference data corresponding to first and second diseases; and a CPU that controls the operation of biomarker analyzer electrophoresis apparatus 10 or portable biomarker analyzer device 190 or portable integrated multidisciplinary biomarker analyzer system 99 or 400 in both the first and second disease modes and compares data relative to the biomarkers detected at a biomarker detection zone with the reference data, the CPU can transmit data detected in the detection zone over the Internet to an evaluator; and the CPU can receive from the evaluator feedback relative to the first and/or second disease. The CPU system can also include an updatable memory operatively connected to the CPU and positioned remote from the CPU.

Although intravenous blood microdialysis can have great utility in monitoring patients in critical conditions, the system is considered a semi-invasive procedure, because to insert the catheter or microdialysis probe into the blood vessel it must be guided with a metal needle similar to the one described in the literature (J. P. Shah, T. M. Phillips, J. V. Danoff, L. H. Gerber. Journal of Applied Physiology, volume 99, pages 1977-1984, 2005), keeping sealed the connection to avoid any type of contamination and taped to the arm to avoid any disconnection from the arm of individual 78. The rest of the components of the microdialysis probe 502 can be made of flexible silicone, for example a liquid silicone rubber manufactured as Silastic™ registered to Dow Corning, or an inert silicone elastomer material to permit flexibility of the system. Furthermore, semi-permeable polymer membranes can be customized to well-defined surface chemistry and pore sizes, where digestive enzymes can be immobilized to their surfaces. Limited proteolysis in these porous membrane reactors containing different types of digestive enzymes can be achieved (J. Dong, W. Ning, W. Liu, M. L. Bruening. Analyst, volume 142, pages 2578-2586, 2017). Controlled digestion of biomolecules and larger biological entities can generate smaller molecular species, increasing the number of signature biomarkers, and therefore, allowing a comprehensive monitoring of a patient under study. The catheter or microdialysis probe, in addition of being inserted into a blood vessel, it might also be inserted into an implantable port that has attached a catheter into a large vein, and it is used for drug injection, usually for chemotherapy.

The processing of data generated by portable biomarker analyzer electrophoresis apparatus 10, or portable biomarker analyzer device 190 or portable integrated multidisciplinary biomarker analyzer system 99 or 400 can be controlled by a central processing unit (CPU) capable of organizing and storing the results and the data can be secured via the Internet to a super-computer with a high level of performance containing a large-scale inventory of a fingerprint database of biomarkers for diagnosis and prognosis of diseases.

Electronic clinical data is the preferred mode of keeping information of a patient health status, as well as maintaining an organized and controlled information of clinical trials. The electronic data information has many advantages, such as reducing error-prone working steps, quality improvements, ensure stable and complete data transfer, share data with other systems, provide new functionality for data integration and automatic analysis, and to save time and money.

Detecting invisible fingerprints is an important task in forensic science, a branch of science that helps criminal investigations by collecting and analyzing evidence from crime scenes. Each fingerprint pattern is unique to a specific person, and therefore a very reliable way of identifying a suspect. Similarly, with the help of supercomputing resources to create machine and deep-learning techniques in an era of artificial intelligence, it is to possible to develop new approaches to mining big data capable to predict how genes, proteins and small molecules interact inside a cell. The emerging technologies of genomics, proteomics, metabolomics, transcriptomics, and other "omics" provide significant information of "molecular fingerprints", which is advancing the field of cancer biology and other chronic diseases with better understanding of disease progression, metastasis, prediction to response to therapy, and estimation of risk assessment of getting a disease. Unique fingerprints composed of molecular changes are captured and subjected to interpretation with the goal of class discovery, comparison or prediction (as described in Bailey, W. J., Ulrich, R. Expert Opinion in Drug Safety 2004, volume 3, pages 137-151).

The use of machine learning algorithms and learning models to predict cancer based on collected data in routine blood analysis of certain "predictor" biomarkers has significant value. Artificial intelligence has the inherent ability to process massive amount of data unique to the individual, helping in the prediction of diseases with increasing individual accuracy (as described in Pham, H., Pham, D. H. Concurrency and Computation Practice and Experience 2019, https://doi.org/10.1002/cpe.5467). The comprehensive biomarker data information generated by portable biomarker analyzer electrophoresis apparatus 10 or portable biomarker analyzer device 190 or portable integrated multidisciplinary biomarker analyzer system 99 or 400 can be connected to supercomputers via the Internet for data analysis and evaluation and can be of great value to support clinical decision-making, which is central to personalized medicine both in the clinic and research.

The processing of data generated by portable biomarker analyzer electrophoresis apparatus 10, or portable biomarker analyzer device 190 or portable integrated multidisciplinary biomarker analyzer system 99 or 400 can be used to determine results for accurate and effective diagnosis and prognosis data of a disease provided by the supercomputer which can be sent via the Internet using a secure and codified system to a family physician to start a treatment or to order tests in case of a mismatching with medical imaging information and/or clinical diagnosis of individual 78 based on signs, symptoms and medical history.

Biomarkers have been used as prognostic and predictors of diseases. A prognostic biomarker is clinical or biological characteristic that provides information on the likely patient health outcome (e.g. disease recurrence) irrespective of the treatment. A predictive biomarker indicates the likely benefit to the patient from the treatment, compared to their condition at baseline.

Biomarkers can be able to reflect the entire spectrum of disease, from the early manifestations to terminal stages. Therefore, the development of any biomarker should precede or go in parallel with standard designs to determine specificity, sensitivity, stability, accuracy, reliability, interpretability, and feasibility. Otherwise, incomplete or wrongful set of biomarkers may lead to a misinterpretation of results. Owing the low sensitivity and specificity of many biomarkers, the use of a panel of biomarkers is preferred in the diagnosis of a disease. A comprehensive panel of biomarkers can improve predictive performance and diagnostic accuracy over individual markers.

Processing of data generated by portable biomarker analyzer electrophoresis apparatus 10, or portable biomarker analyzer device 190 or portable integrated multidisciplinary biomarker analyzer system 99 or 400 provides inexpensive, reliable, robust, and rapid determination of data to generate a panel of biomarkers which can help in the early diagnosis and timely intervention of a disease.

If the results of diagnosis and prognosis of a disease generated by processing of data generated by portable biomarker analyzer electrophoresis apparatus 10, or portable biomarker analyzer device 190 or portable integrated multidisciplinary biomarker analyzer system 99 or 400 provided by the supercomputer and sent via the Internet to the family physician is correct and matching with medical imaging information and/or a clinical diagnosis of the patient, then the fingerprint biomarker information and disease information can be sent back to portable biomarker analyzer electrophoresis apparatus 10, or portable biomarker analyzer device 190 or portable integrated multidisciplinary biomarker analyzer system 99 or 400 to be stored and used for matching with another set of identical biomarkers obtained from a sample specimen of a different patient.

Relevant biomarkers of wellness and disease can be stored into a supercomputer to create a selected "literature bank" of billions of data points of an entire biological signature of proteins, peptides, nucleic acids, glycans, lipids, metabolites, and additional information of family history of diseases, and clinical signs and symptoms that are collected each time that visit a patient visit a doctor. These signature data points can be systematically stored for a large population generating a ranked list of conditions and diseases to then compare such "data mining" information with the information generated by portable biomarker analyzer electrophoresis apparatus 10, or portable biomarker analyzer device 190 or portable integrated multidisciplinary biomarker analyzer system 99 or 400 and stored in the CPU. It is advantageous to identify the accuracy and reliability of biomarkers based on its sensitivity (the ability to identify "sick" people) and specificity (the ability to differentiate between "healthy" and "sick" people). Public data deposition in genomics and proteomics repositories, and data mining can be used value in advancing biomarker discovery and medical science.

If the results of diagnosis and prognosis of a disease generated by processing of data generated by portable biomarker analyzer electrophoresis apparatus 10, or portable biomarker analyzer device 190 or portable integrated multidisciplinary biomarker analyzer system 99 or 400 provided by the supercomputer and sent via the Internet to the family physician is correct and matching with the medical imaging information and/or the clinical diagnosis of the patient, then the fingerprint biomarker information and disease information is sent back to portable biomarker analyzer electrophoresis apparatus 10, or portable biomarker analyzer device 190 or portable integrated multidisciplinary biomarker analyzer system 99 or 400 to be stored and used for continuing monitoring of the evolution of the disease in the same patient during a specified time by consecutive testing of the same biomarkers, changes in the qualitative and quantitative profile of the biomarkers, appearance of new biomarkers, or modification of one or more biomarkers, or disappearance of one or more biomarkers, and the monitoring of the effectiveness of the treatment.

Frequent testing of one or a panel of biomarkers is advantageous to the patient and to the physician. In the case of self-monitoring blood glucose in diabetic patients, it allows the determination of glucose on frequent basis, confirming hypoglycemia or hyperglycemia, and thereby facilitating therapeutic adjustment to achieve long-term goals. Frequent testing facilitates patient education about the disease and its management given patients more self-care responsibilities and motivating people toward healthier behavior. The determination of a panel of biomarkers provides clinical effectiveness and cost effectiveness. Biomarkers have the potential to improve medical and pharmacy payer policies across therapeutic applications ranging from central nervous system and cardiovascular disorders to immune system and inflammatory diseases. In the case of the inflammatory disease rheumatoid arthritis, where prevalence is high and biologic medications are expensive, biomarker testing can ensure the appropriate clinical use of most costly medicines.

Portable biomarker analyzer electrophoresis apparatus 10, or portable biomarker analyzer device 190 or portable integrated multidisciplinary biomarker analyzer system 99 or 400 can generate a panel of biomarkers which can help significantly in providing frequent tests at low cost. Analyte concentrator-microreactor (ACM) device 42 can contain well-oriented biorecognition affinity ligands immobilized covalently that are stable and can be re-used multiple times, reducing significantly the cost of each test.

Portable biomarker analyzer electrophoresis apparatus 10, or portable biomarker analyzer device 190 or portable integrated multidisciplinary biomarker analyzer system 99 or 400 can be used in a data-driven strategy of matching a panel of biomarkers generated by the use of portable biomarker analyzer electrophoresis apparatus 10, or portable biomarker analyzer device 190 or portable integrated multidisciplinary biomarker analyzer system 99 or 400 from one or more sample specimens with a large-scale of disease-identifying biomarkers obtained from patient data sets being used as fingerprints of diagnosis and prognosis of diseases for increasing the accuracy, sensitivity and specificity of the disease, and providing a rapid and effective health screening technology and delivering the best treatment to a patient.

Effective integration of data-driven and knowledge-based approaches for biomarker identification has been recognized as key to improving the identification of high-performance biomarkers that are necessary for identifying molecular biomarkers of disease processes Data-driven, knowledge-based approaches to improve predictive performance of biomarkers can contribute to identification of biomarker signatures or fingerprints for disease classification facilitating precision medicine. Precision medicine is aimed to deliver "the right drug for the right patient at the right time." Having a comprehensive high-performance chemical and/or biochemical biomarker signature can make it possible to predict whether a certain therapy will be effective for individual 78. Physicians can use molecular biomarkers to guide all aspects of care for patients with cancer or at risk of developing cancer. For highly targeted therapies, diagnostic tests integrating biomarker technology to identify prospectively the appropriate patients for treatment can be useful for clinical development.

Portable biomarker analyzer electrophoresis apparatus 10, or portable biomarker analyzer device 190 or portable integrated multidisciplinary biomarker analyzer system 99 or 400 can be capable of generating a panel of clinically meaningful biomarkers which can help significantly in providing an effective health screening technology for better diagnosis, prognosis, and treatment of patients.

Portable biomarker analyzer electrophoresis apparatus 10, or portable biomarker analyzer device 190 or portable integrated multidisciplinary biomarker analyzer system 99 or 400 can determine biomarkers of diagnosis and/or prognosis present in a biosample which are generated during a healthy or a disease state and can be constituents or biomolecules of a same group or category such as proteomics or peptidomics, or a different group such as genomics or transcriptomics, glycomics, lipidomics, and metabolomics, or a combination of one or more biomarkers belonging to different groups.

Biomarkers are important for screening and to discriminate a healthy individual from one having an asymptomatic disease, and from one having an advance stage of a disease. The evolution of molecular medicine, including a broad range of biomarkers, can play a significant role in reshaping medicine. The fundamental definitions and concepts of biomarkers are complex, depending on their respective uses in patient care, clinical research, or therapeutic development. Biomarkers can be distinguished on the following categories: diagnostic biomarkers which incorporate disease detection, prognostic biomarkers that represent prediction of the course of a particular disease (e.g. recurrence, progression and survival), and predictive biomarkers that would allow for prediction of the response to treatment which could be subsequently applied in patient assessment.

If part of a gene is altered (e.g., one or more mutations), the protein expressed of that gene is also altered (e.g., change in one or more amino acids). However, only a small percentage of mutations cause genetic diseases. Some mutations that alter the sequence of a gene do not change the function of the protein made by the gene. A very small percentage of mutations may have a positive effect. Therefore, not all biomarkers should be focused only in genetic biomarkers. Cell proteins can also be used for diagnosing disease and disease control.

Portable biomarker analyzer electrophoresis apparatus 10, or portable biomarker analyzer device 190 or portable integrated multidisciplinary biomarker analyzer system 99 or 400 is capable of generating a panel of clinically meaningful biomarkers as individual group of biomarkers, or as a combination of critical biomarkers of each group.

Portable biomarker analyzer electrophoresis apparatus 10, or portable biomarker analyzer device 190 or portable integrated multidisciplinary biomarker analyzer system 99 or 400 can determine if one or a panel of biomarkers of diagnosis and/or prognosis present in one or more biological fluids or biosamples from individual 78 to provide comprehensive information to identify a particular infectious microorganism such as a virus or bacteria, the individual body response to the infection by the microorganism such as the production of specific antibodies immunoglobulin M (IgM) and/or immunoglobulin G (IgG), an additional inflammatory response caused by the infectious microorganism including cytokines and/or chemokines, extra biomarkers causes by the infectious microorganism increases levels of collagens, collagen-derived peptides, prolyl hydroxylases, hydroxyproline-containing peptides, proline, hydroxyproline, lysyl oxidase, C-reactive protein, procalcitonin, ferritin, and/or circulation cellular and exosome constituents when compared to a non-infected individual.

Distinct patterns of circulating cytokines and acute-phase responses have been used for guiding the diagnosis and management of infectious diseases. For example, when referring to the inflammatory response to viral (IL-18/ferritin) and bacterial (IL-6/CRP) infections presents with specific plasma patterns of immune biomarkers.

It is desirable to differentiate infectious diseases causes by viral pathogens from bacterial pathogens. In cases such as community-acquired pneumonia, clinical signs and symptoms causes by virus or bacteria overlap significantly. The uncertainty is further exacerbated by the fact that direct isolation of possible causative agent from the lower respiratory tract is invasive and therefore rarely performed. Medical history, physical findings, and other ancillary medical tests are frequently similar for different causative agents and do not provide definitive discrimination. Misdiagnosis of disease etiology may alter the trajectory of patient care, including over and under use of antibiotics, with fundamental individual and global health consequences. Disease manifestations caused by microbial pathogens may vary from mild to severe, and in some cases requiring admission and hospitalization in intensive care units. Therefore, as soon as the early manifestations of symptoms of the disease appear, the sooner is the need to have an accurate and precise diagnosis to start the appropriate therapy. Pro- and anti-inflammatory cytokines have been associated to infectious disease. For example, in the case of human respiratory syncytial virus a few cytokines have been highlighted as biomarkers of diagnosis of the severity of the disease. Among these biomarker cytokines are, interleukin-8 (IL-8), interferon-alpha (IFN-alpha), interleukin-6 (IL-6), and the Th2-type cytokines thymic stromal lymphopoietin (TSLP), interleukin-3 (IL-3), and interleukin-33 (IL-33) (as described in Vazquez, Y., Gonzalez, L., Noguera, L., Gonzalez, P. A., Riedel, C. A., Bertrand, P., Bueno, S. M. Frontiers in Immunology 2019, volume 10, 1154, doi: 10.3389/fimmu.2019.01154). In the case of community-acquired bacterial infection, significant elevation of cytokines (IL-1Ra, IL-2, IL-6, and TNF-alpha) were found in the serum of patient with bacterial infections, when compared with viral infections (as described in Holub, M., Lawrence, D. A., Andersen, N., Davidova, A., Beran, O., Maresova, V., Chalupa, P. Mediators of inflammation 2013, volume 2013, 190145, http://dx.doi.org/10.1155/2013/190145). In the case of the severe acute respiratory syndrome (SARS), plasma cytokine and chemokine profiles showed markedly elevated Th1 cytokine interferon (IFN)-$\gamma$, inflammatory cytokines interleukin (IL)-1$\beta$, IL-6 and IL-12, neutrophil chemokine IL-8, monocyte chemoattractant protein-1 (MCP-1), and Th1 chemokine IFN-$\gamma$-inducible protein-10 (IP-10) for at least two weeks after disease onset, but there was no significant elevation of inflammatory cytokine tumor necrosis factor (TNF)-$\alpha$ and anti-inflammatory cytokine IL-10 (as described in Lam, C. W. K., Chan, M. H. M., Wong, C. K. The Clinical Biochemist Reviews 2004, volume 25, pages 121-1323).

The development of a cytokine storm is a potentially fatal immune condition characterized by rapid proliferation and hyperactivation of T cells, macrophages, natural killer cells and the overproduction of more than 150 inflammatory cytokines and chemical mediators released by immune or nonimmune cells. In SARS-CoV infected patients, high levels of serum pro-inflammatory cytokines (IFN-$\gamma$, IL-1, IL-6, IL-12, and TGF$\beta$) and chemokines (CCL2, CXCL10, CXCL9, and IL-8) were detected in cases of severe disease compared to patients with uncomplicated SARS (as described in Sun, X., Wang, T., Cai, D., Hu, Z., Chen, J., Liao, H., Wei, H., Zhang, Z., Qiu, Y., Wang, J., Wang, A. Cytokine & Growth Factor Reviews 2020, https://doi.org/10.1016/j.cytogfr.2020.04.002). Initial immune and inflammatory responses induce a severe cytokine storm during the rapid progression phase of COVID-19. Early evaluation and continued monitoring of cardiac damage (cTnI and NT-proBNP) and coagulation (D-dimer) after hospitalization may identify patients with cardiac injury and predict COVID-19 complications.

Many COVID-19 patients who have been admitted to intensive care, required mechanical ventilation, or died, had a comorbidity, of which the most common was hypertension. This description of the group in whom SARS-CoV-2 infection is most lethal is also highly representative of patients suffering with idiopathic pulmonary fibrosis (IPF). IPF characteristically affects men in their seventh or eighth decade of life, commonly with comorbidities such as hypertension, diabetes, and ischemic heart disease, and with a history of cigarette smoke exposure (as described in George, P. M., Wells, A. U., Jenkins, R. G. The Lancet-Respiratory Medicine 2020, https://doi.org/10.1016/S2213-2600(20)

30225-3). Pulmonary fibrosis is characterized by disturbances of extracellular matrix protein deposition resulting from fibroblast activation and proliferation. Overexpression of collagen and the enzymes involved in collagen biosynthesis, such as prolyl-hydroxylases, lysyl hydroxylase, proline and hydroxyproline is a hallmark of organ fibrosis (as described in Desogere, P., Tapias, L. F., Hariri, L. P., Rotile, N.J., Rietz, T. A., Probst, C. K., Blasi, F., Day, H., Mino-Kenudson, M., Weinreb, P., Violette, S. M., Fuchs, B. C., Tager, A. M., Lanuti, M., Caravan, P. Science Translational Medicine 2017, volume 9, eaaf4696, doi:10.1126/scitranslmed.aaf4696; Prockop, D. J., Kivirikko, K. I., Tuderman, L., Guzman, N. A. The New England Journal of Medicine 1979, volume 301, pages 13-23 and 77-85).

Determination of the serology for antibodies present in viral infections, such as immunoglobulins A, G and M (IgA, IgG and IgM) has been quantified in serum or plasma of infected individuals. The values of these immunoglobulins have been used for differentiation of seronegativity, acute primary infection, or past infection for viral infections (as described in Journal of Clinical Microbiology 2001, volume 39, pages 3902-3905).

The serum levels of C-reactive protein (CRP), procalcitonin (PCT) and ferritin are markedly increased in very severe compared with severe COVID-19. Increased CRP, PCT and ferritin level might correlate to secondary bacterial infection and associated with poor clinical prognosis (as described in Zhou, B., She, J., Wang, Y., Ma, X. Research Square 2020, doi:10.21203/rs.3.rs-18079/v1; Lippi, G., Plebani, M. Clinica Chimica Acta 2020, volume 505, pages 190-191).

Portable biomarker analyzer electrophoresis apparatus 10, or portable biomarker analyzer device 190 or portable integrated multidisciplinary biomarker analyzer system 99 or 400 is capable of generating a panel of clinically meaningful biomarkers of importance in the differentiation between viral and bacterial infections and the monitoring of the disease from the early stage to the advancement of the severity of the disease.

Foley catheter urine collection system 140 and the exhaled breath and oral fluid collection system 70 can work in coordination and in sequential order to maximize the amount of biomarkers obtained from individual 78 monitored by a healthcare professional in a hospital setting, a transportation vehicle such an ambulance, a doctor's office biaclinical setting, and potentially at the patient's home.

It is desirable that critical tests can be performed in remote places, far away from a medical facility, or during the air or ground transport of critical ill patients as a potential opportunity to improve patient care. A rapid and accurate diagnosis obtained by a panel of clinical important biomarkers, the capability of better communication and data transfer through digital and wireless technology, linked to a medical workstation with supercomputers, can provide a rapid therapeutic intervention and save the life of a person in critical conditions. Telemedicine is a key component of medical care on the International Space Station where astronauts and cosmonauts stay for long period of time in the world's most remote environment. Substances found in exhaled breath, saliva and urine can be useful indicators and potential biomarkers of various diseases and metabolic activities, facilitating disease diagnosis and/or toxic conditions. Life-threating emergencies, such as heart attack, serious head injury, poisoning, pregnancy-related problems, severe abdominal pain, loss of consciousness, convulsions, sepsis, and diabetic coma are just some of the most common medical situations that require a rapid and accurate diagnosis to start the most appropriate treatment to a patient. The knowledge, skills, and attitudes that prevail in critical care medicine are useful attributes in the management of critical ill patients. The right diagnosis made in a timely manner lead to the best treatment, and a patient has the best opportunity for a positive health outcome, Diagnostic error is a diagnosis that is missed, wrong or delayed, as detected by some subsequent definitive test or finding.

Primary prevention includes those measures that prevent the onset of illness before the disease begins, for example, immunization against an infectious disease. Secondary prevention includes those measures that lead to early diagnosis and prompt treatment of a disease. Portable biomarker analyzer electrophoresis apparatus 10, or portable biomarker analyzer device 190 or portable integrated multidisciplinary biomarker analyzer system 99 or 400 are capable of generating a panel of clinically meaningful biomarkers from exhaled breath, saliva and urine, useful for the determination of a diagnosis even before symptoms manifest.

E-health is often used as a generic term to describe all forms of Information and Telecommunication Technology (ICT) related to the field of medicine. Telemedicine is a subset of E-health and refers only to the use of electronic information and communication technologies to provide and support healthcare when distance separate participants.

Rural residents often encounter barriers to healthcare that limit their ability to obtain the care they need. In order for rural residents to have sufficient access, necessary and appropriate healthcare services must be available and obtainable in a timely manner. Primary care and early diagnosis are crucial in the frame of containing costs, providing more efficacious actions thus preventing unnecessary hospital accesses, improving timeliness of care and reducing waiting lists. Delayed disease diagnosis, as a consequence of poor access to healthcare services, has been demonstrated as one of the major problems in rural communities. Point-of-care diagnostics using portable biomarker analyzer electrophoresis apparatus 10, or portable biomarker analyzer device 190 or portable integrated multidisciplinary biomarker analyzer system 99 or 400 has the potential to improve healthcare access in settings that have limited laboratory infrastructure. Use of point-of-care diagnostics generated by portable biomarker analyzer electrophoresis apparatus 10, or portable biomarker analyzer device 190 or portable integrated multidisciplinary biomarker analyzer system 99 or 400 can ensure the completion of the test and the treatment cycle in the same encounter, which has immense potential to reduce diagnostic and treatment delays and to impact patient outcomes.

Point-of-care diagnostics using portable biomarker analyzer electrophoresis apparatus 10, or portable biomarker analyzer device 190 or portable integrated multidisciplinary biomarker analyzer system 99 or 400 is capable of generating a panel of clinically meaningful biomarkers from exhaled breath, saliva and urine, useful for the determination of a diagnosis even before symptoms manifest. Point-of-care diagnostics using portable biomarker analyzer electrophoresis apparatus 10, or portable biomarker analyzer device 190 or portable integrated multidisciplinary biomarker analyzer system 99 or 400 can qualify for the thematic content of the World Health Organization known as ASSURED (Affordable, Sensitive, Specific, User friendly, Rapid, and to Enable and Deliver to those who need it).

Point-of-care diagnostics using portable biomarker analyzer electrophoresis apparatus 10, or portable biomarker analyzer device 190 or portable integrated multidisciplinary biomarker analyzer system 99 or 400 to determine a panel of biomarkers generated by the use of one or more analyte concentrator-microreactor (ACM) devices 42 is advantageous to understand why in some people with COVID-19 the immune system secretes too many cytokines generating a cytokine storm and in others there is no formation of a cytokine storm, and why COVID-19 kills some people and spares others.

Cytokine storms are associated with a wide variety of infectious and noninfectious diseases. It is desirable to provide an improved understanding of the molecular events that precipitate a cytokine storm, of the contribution such a "storm" makes to pathogenesis, or of what therapeutic strategies might be used to prevent the storm or stop it once it has started. Many cytokines have multiple and sometimes unrelated functions that depend on the target cell or on the presence or absence of other cytokines.

COVID-19, a disease caused by the virus known as severe acute respiratory syndrome coronavirus 2 or SARS-CoV-2, has manifested a wide range of uncertain symptoms. According to a study from Italy, some 43 percent of people with the virus have no symptoms. Others have mild symptoms, and others have severe symptoms developing respiratory failure, septic shock, and/or multiple-organ failure. Many others keep feeling better and eventually they totally recover. There is a big difference in how people handle the virus. It has been found that Latinos and African Americans (low socioeconomic status) have died at significantly higher rates than white Americans, as well as those individuals called "high-risk" people, which are older and have chronic medical conditions, such as obesity, diabetes, and high blood pressure (as described in Hamblin, J. The Atlantic-Health 2020, April 21).

The body's first line of defense, the innate immune response, starts right after an infection is taken place killing the virus and any cells damaged by it. The second line of defense, the adaptive immune response, kicks in days later if any virus remains, employing what it has learned about the virus to mobilize a variety of special forces such as T cells and B cells.

The flu is a fast-moving infection that attacks certain target cells on the surface of the upper respiratory system and kills almost all of the target cells within two to three days. The death of these cells deprives the virus of more targets to infect and allows the innate immune response time to clear the body of almost all of the virus before the adaptive system comes into play.

In the case of COVID-19, which targets surface cells throughout the respiratory system including in the lungs, has an average incubation of six days and a much slower disease progression. It appears that the adaptive immune response may kick in before the target cells are depleted, slowing down the infection and interfering with the innate immune response's ability to kill off most of the virus quickly. This longer duration of viral activity may lead to an overreaction of the immune system, called a cytokine storm, which kills healthy cells, causing tissue damage. Furthermore, if the virus is not completely cleared, and the target cells regenerate, the virus can take hold again and reach another peak.

COVID-19 vaccines can be made focusing on the generation of a good immune response generating effective antibodies. These proteins are made by B cells and ideally latch onto SARS-CoV-2 and prevent it from entering cells. T cells, in contrast, thwart infections in two different ways. Helper T cells spur B cells and other immune defenders into action, whereas killer T cells target and destroy infected cells. The severity of disease can depend on the strength of these T cell responses. Activation and priming of innate and adaptive immune responses should result in pathogen clearance and recovery. However, in a proportion of infected individuals, SARS-CoV, MERS-CoV and likely SARS-CoV2 evade immune system recognition through suppression of these mechanisms, a phenomenon associated with more severe disease and poorer prognosis (as described in Felsenstein, S., Herbert, J. A., McNamara, P. S., Hedrich, C. M. Clinical Immunology 2020, volume 215, 108448, doi: 10.1016/j.clim.2020.108448).

It is possible to separate different sub-populations of peripheral blood mononuclear cells (lymphocytes and monocytes) on the basis of the immunological identity of the surface of cells using density perturbation methods involving antibody-coated dense polystyrene beads.

Point-of-care diagnostics using portable biomarker analyzer electrophoresis apparatus 10, or portable biomarker analyzer device 190 or portable integrated multidisciplinary biomarker analyzer system 99 or 400 can isolate and concentrate peripheral blood mononuclear cells, then separate, detect, quantify and characterize the individually separated cell types. Point-of-care diagnostics using portable biomarker analyzer electrophoresis apparatus 10, or portable biomarker analyzer device 190 or portable integrated multidisciplinary biomarker analyzer system 99 or 400 is capable of the isolation of bacteria cells, viruses and polymeric particles.

Stressors play a significant role in diseases. For example, cytokines like IL-6 can be elevated by a single night of bad sleep. Over the course of a lifetime, the effects of daily and hourly stressors accumulate. Experts theorize that whether a coronavirus infection takes a turn for the worse depends on a person's immune response. The virus matters, but the host response matters at least as much, and probably more. For reasons that are not entirely clear, some people, especially the elderly and sick, may have dysfunctional immune systems that fail to keep the response to particular pathogens in check. This could cause an uncontrolled immune response, triggering an overproduction of immune cells and their signaling molecules and leading to a cytokine storm often associated with a flood of immune cells into the lung. Genetic and environmental risk factors, as well as sex disparity, can help explain the severity of infections.

It is desirable to determine the mechanisms which can trigger infection with COVID-19 in a person with diabetes. The most common mechanisms include chronic inflammation, increased coagulation activity, immune response impairment and potential direct pancreatic damage by SARS-CoV-2. Scientists have found that patients with obesity or diabetes showed immune systems that were not working properly, with an impairment of white blood cells called Natural Killer (NK) cells and B cells, both of which help the body fight off infections. Type 2 diabetes has been linked with impairment of the very system in the body that helps to fight off infections like COVID-19 and could explain why a person with diabetes is at high risk for a severe infection.

People with conditions that affect the cardiovascular system, such as heart disease and hypertension, generally suffer worse complications from COVID-19 than those with no preexisting conditions, according. In one scenario, by attacking the lungs directly, the virus might deplete the body's supply of oxygen to the point that the heart must work harder to pump oxygenated blood through the body. The virus might also attack the heart directly, as cardiac tissue contains angiotensin-converting enzyme 2 (ACE2), a molecule that the virus plugs into to infect cells. In some individuals, COVID-19 can also kickstart an overblown immune response known as a cytokine storm, wherein the body becomes severely inflamed and the heart could suffer damage as a result. It is known that smoke exposure increases the number of ACE2 receptors in the lungs which is the receptor that SARS-CoV-2 plugs into to infect cells. Other factors influencing the SARS-CoV-2 infection is blood type. Individuals with blood types in the A group (A-positive, A-negative and AB-positive, AB-negative) were at a higher risk of contracting the disease compared with non-A-group types. People with O blood types (O-negative and O-positive) had a lower risk of getting the infection compared with non-O blood types. Why blood type might increase or decrease a person's risk of getting SARS-CoV-2 is not known. A person's blood type indicates what kind of certain antigens cover the surfaces of their blood cells. These antigens produce certain antibodies to help fight off a pathogen. Another factor is the genetic factor. For example, specific combinations of human leukocyte antigen (HLA) genes, which train immune cells to recognize germs, may be protective against SARS-CoV-2, while other combinations leave the body open to attack. HLAs represent just one cog in our immune system machinery, though, so their relative influence over COVID-19 infection remains unclear.

Another factor characterizing COVID-19 is coagulation abnormalities. Although most patients with coronavirus disease 2019 (COVID-19) predominantly have a respiratory tract infection, a proportion of patients progress to a more severe and systemic disease, characterized by treatment-resistant pyrexia, acute lung injury with acute respiratory distress syndrome (ARDS), shock, and multiple organ dysfunction, associated with substantial mortality. Many patients with severe COVID-19 present with coagulation abnormalities that mimic other systemic coagulopathies associated with severe infections, such as disseminated intravascular coagulation (DIC) or thrombotic microangiopathy, but COVID-19 has distinct features. Coagulopathy in patients with COVID-19 is associated with an increased risk of death. Furthermore, the relevance of COVID-19-coagulation abnormalities are becoming increasingly clear as a substantial proportion of patients with severe COVID-19 develop, sometimes unrecognized, venous and arterial thromboembolic complications. Coronavirus infections are also associated with a remarkable activation of the fibrinolytic system. In addition, plasma concentrations of tissue-type plasminogen activator (t-PA) were 6-times higher in patients infected with human severe acute respiratory syndrome coronavirus 1 (SARS-CoV-1) than in patients with no infection. Inflammation-induced endothelial cell injury could result in massive release of plasminogen activators, which could explain the high concentrations of D-dimer and fibrin degradation products in patients with severe COVID-19. The D-dimer is a fibrin degradation product, a small protein fragment present in the blood after a blood clot is degraded by fibrinolysis.

It is desirable to understand more about virus SARS-CoV-2 and the disease COVID-19. Currently it has been shown that those most affected by the virus are those having the following conditions: age, diabetes (type 1 and type 2), heart disease and hypertension, smoking, blood type, obesity, and genetic factors. Accordingly, all pertinent biomarkers that are elevated in patients with these factors or conditions are advantageous to have a better diagnosis of the disease, even before symptoms are manifested. Some of the most critical biomarkers to be measured in patients of COVID-19 are cytokines, chemokines, C-reactive protein, ferritin, the fibrin degradation product D-dimer, tissue-type plasminogen activator, collagen related peptides and enzymes, vitamin D, markers of renal function and markers of autoimmune diseases, blood platelet count, and circulating endothelial cells.

Point-of-care diagnostics using portable biomarker analyzer electrophoresis apparatus 10, or portable biomarker analyzer device 190 or portable integrated multidisciplinary biomarker analyzer system 99 or 400 is capable of generating a panel of clinically meaningful biomarkers from biological fluids or biosamples, including cell entities, subcellular entities, extracellular vesicles, their chemical and biochemical content, small molecular weight substances, biomolecules, simple and complex substances. Point-of-care diagnostics using portable biomarker analyzer electrophoresis apparatus 10, or portable biomarker analyzer device 190 or portable integrated multidisciplinary biomarker analyzer system 99 or 400 can analyze multiple biomarkers accurately, rapidly, and cost-effectively which can be advantageous in COVID-19 diagnostic testing.

It is to be understood that the above-described embodiments are illustrative of only a few of the many possible specific embodiments, which can represent applications of the principles of the invention. Numerous and varied other arrangements can be readily devised in accordance with these principles by those skilled in the art without departing from the spirit and scope of the invention.

What is claimed is:

1. A disease detection system, comprising:
a portable biomarker analyzer electrophoresis apparatus including: (a) a main transport passage; (b) a secondary transport passage; (c) a plurality of separation passages, each of the separation passages having a separation passage overlapping portion that overlaps a different portion of the main transport passage, the separation passage overlapping portion of each of the separation passages has a staggered configuration where the main transport passage and the separation passages connect at two separate and distinct points, the respective separation passage overlapping portions includes an elongated separation passage portion, the plurality of separation passages being separate and independently communicable upstream of the respective overlapping portions with a separation buffer supply or with a supply of an elution buffer or solution; (d) a different analyte concentrator-microreactor (ACM) device in each of the overlapping portions that isolates and concentrates a different biomarker from one or more biological sample specimens from an animal or organism, the one or more biological sample specimens being introduced into an inlet end of the main transport passage or an inlet end of the secondary transport passage; a first set of the different biomarkers being associated with a first disease and a different second set of the biomarkers being associated with a second disease, each of the analyte concentrator-microreactor (ACM) devices includes at least one affinity ligand capable of attracting the respective different biomarker from the one or more biological sample specimens; and (e) a valve system operable at least in part to control fluid flow through the main transport passage and the secondary transport passage from the inlet end of the main transport passage to an outlet end of the main transport passage and from the separation passages to a detection zone; a computer including a central processing unit (CPU) and an updatable memory, the updatable memory having reference data corresponding to first and second diseases, the central processing unit (CPU) executes instructions to control the operation of the portable biomarker analyzer electrophoresis apparatus and an evaluator in both first and second disease modes and compares data relative to the biomarkers detected at the detection zone with the reference data in the updatable memory, the central processing unit (CPU) transmits data detected in the detection zone over the Internet to the evaluator and the central processing unit (CPU) receives from the evaluator feedback relative to the first and/or second diseases, the valve system controlling the flow of a separation buffer in the separation passages introduced from the separation buffer supply or a plug of an elution buffer or solution in the separation passages introduced from the biomarker elution buffer supply in a sequential order from an inlet end of the respective separation passages to an outlet end of the respective separation passages, the detection zone located at the outlet end of the separation passages, the valve system being selectively operable in the first disease mode wherein biomarkers associated with the first disease are released from a first set of the analyte concentrator-microreactor (ACM) devices for delivery to the detection zone and in an alternative in the second disease mode wherein biomarkers associated with the second disease are released from a second set of the biomarker analyte concentrator-microreactor (ACM) devices for delivery to the detection zone, the biomarkers associated with the first disease delivered to the detection zone and the biomarkers associated with the second disease delivered to the detection zone being detected, quantified, and characterized by one or a plurality of simultaneously operating detectors localized in the detection zone; wherein the inlet end of the secondary transport passage has a coupling connection to a Foley catheter urine collection system, the coupling connection being a tubing connecting system containing one or more polymeric membrane filters forming a matrix configured for retaining aggregated materials or biomolecules, the tubing being a solid support configured to immobilize digestive enzymes, a detergent-containing buffer or solution received in said tubing connecting system to aid in the partial or total breakdown of cellular and vesicular entities or dissolution of clotting or biomolecular aggregates and maintain a smooth path of sample specimen through the tubing connection system, the Foley catheter urine collection system configured to collect the one or more biological sample specimens, wherein the evaluator includes instructions that the central processing unit (CPU) executes to determine a panel of biomarkers from the biomarkers associated with the first disease and the biomarkers associated with the second disease, wherein transport and passage through the secondary transport passage and the main transport passage of the biological sample specimen from the inlet side of the secondary transport passage and throughout the main transport passage passing through the analyte concentrator-microreactor (ACM) device all the way to the outlet side of the main transport passage to a trap or waste container localized at the outlet side of the main transport passage is made by the aid of a vacuum pump.

2. The system of claim 1 wherein the biological sample specimens are collected by the Foley catheter urine collection system, the biological sample specimens contain chemical, biological, cellular, subcellular, and vesicular constituents.

3. The system of claim 1 wherein the analyte concentrator-microreactor (ACM) device in each of the overlapping portions captures biomarker constituents present in urine from the Foley catheter urine collection system.

4. The system of claim 1 wherein each of the analyte concentrator-microreactors has one or a plurality of immobilized biorecognition affinity-concentrator ligands and/or one or a plurality of immobilized biorecognition affinity-reactor ligands.

5. The system of claim 4 wherein the biorecognition affinity-concentrator ligands are at least one aptamer, lectin, antibody, antibody fragment, metal ion, dye, biotin, avidin, cellular receptor, protein A, protein G, protein L, hormone, multiple adenosine phosphates, boronate, recombinant protein, fusion protein, chemically or biologically modified protein or nucleic acid, cellular or subcellular entity, cellular vesicle, vitamin, enzyme cofactor, enzyme inhibitor, enzyme substrate analog, natural or synthetic small molecule, metabolite, polysaccharide, modified polysaccharide, natural or synthetic biopolymer, complementary base sequence, histones, carrier protein, cytokines, ferritin, heparin, triazine, or cellular membrane; and wherein the biorecognition affinity-reactor ligands include at least one digestive enzyme comprising a proteolytic enzyme, protease, pepsin, trypsin, papain, bromelain, kallikrein; a peptidase, aminopeptidase, carboxypeptidase; a nucleic acid digestive enzyme, nuclease, exonuclease, deoxyribonuclease, ribonuclease; a carbohydrate digestive enzyme, amylase, maltase, lactase, pectinase, cellulase, glucanase, ucrase; a lipid digestive enzyme or lipase, artificial enzymes or synzymes.

6. The system of claim 1 wherein the different biomarkers from the one or more biological sample specimens comprise at least one of proteins, peptides, nucleic acids, lipids, oligosaccharides, cellular and subcellular entities, vesicular entities, viruses, bacteria, other species of microorganisms, ions, metabolites and small molecular weight molecules, inflammatory molecules, products of degradation, organic and inorganic molecules, volatile molecules, semi-volatile molecules, non-volatile molecules, or modified biomolecules.

7. The system of claim 1 wherein the inlet end of the main transport passage is alternatively in communication with a supply of a cleaning solution, a supply of a conditioning buffer, a supply of a sample specimen, a supply of a chromophore-containing solution, and a supply of a washing buffer.

8. The system of claim 1 wherein the inlet end of the secondary transport passage is alternatively in communication with a supply of a cleaning solution, a supply of a conditioning buffer, a supply of a sample specimen, and a supply of a washing buffer.

9. The system of claim 1 wherein the inlet end of the separation passage is alternatively in communication with a supply of a separation buffer, a supply of an elution solution, and a supply of an elution solution containing a chromophore.

10. The system of claim 1 wherein the detectors localized at the detection zone comprises an ultraviolet-visible detector, fluorescence, laser-induced florescence, amperometric-electrochemical, radiometric, phosphorescence, chemiluminescence, mass spectrometer, circular dichroism, or a combination of these detectors.

11. The system of claim 1 wherein a hermetically sealed container or vessel with screw-cap can have a tubular passage where a platinum-iridium electrode is guided into the container, and using the same tubular passage an inert gas is introduced into the container to generate pressure to move the separation buffer or an elution solution into the separation passage.

12. The system of claim 1 wherein the valve system comprises a first valve in the main transport passage upstream of one of the staggered configurations, a second valve in the main transport passage downstream of one of the staggered configurations, a third valve in the separation passage associated with one of the staggered configurations and upstream of one of the staggered configurations and a fourth valve in the separation passage and downstream of one of the staggered configurations, the third valve and the fourth valve of the valve system being selectively operable in a first disease mode and the valve system can be reinforced with a second auxiliary valve for each of the valves and operated and controlled independently by a computer-controlled system, or each of the valves can have a separated switch on and off mechanism working independently and controlled by a computer-controlled system.

13. The system of claim 1 wherein two analyte concentrator-microreactor (ACM) devices, one with immobilized biorecognition affinity-reactor ligands and a second with immobilized biorecognition affinity-concentrator ligands work separately and independently, to digest biomolecules into molecules having a smaller size and to capture or retain only a selected group of signature biomarker peptides, oligonucleotides, oligosaccharides, small-size lipids, glycopeptides or glycolipids.

14. The system of claim 1 wherein the biorecognition affinity-concentrator ligands immobilized to the analyte concentrator-microreactor (ACM) device comprises at least two capture reagents, of which the function of one is to capture a target biomarker present in the sample specimen, and the function of the other is to capture a known chemical or biochemical substance that serves the purpose of behaving as an internal standard control capable of monitoring the quality of the procedure, to determine reagents integrity, to assess the endurance to the action of washing and cleaning and elution reagents, to correct the variability of migration and peak areas of the target biomarker due to several factors, to predict the longevity of the analyte concentrator-microreactor (ACM) device after multiple uses, and to improve data quality.

15. The system of claim 1 wherein processing of the data generated by the portable biomarker analyzer electrophoresis apparatus controlled by instructions the central processing unit (CPU) executes to organize and store results, and submit results via the Internet to a supercomputer containing an inventory of a fingerprint database of biomarkers to determine diagnosis and prognosis of diseases and wherein results of accurate and effective diagnosis and prognosis data of a disease provided by the supercomputer is sent via the Internet using a secure and codified system to a family physician to start a treatment or to order new tests in case of a mismatching with medical imaging information and/or clinical diagnosis of a patient based on signs, symptoms and medical history and wherein if the results of diagnosis and prognosis of a disease provided by the supercomputer and sent via the Internet to the family physician is correct and matching with the medical imaging information and/or the clinical diagnosis of the patient, then fingerprint biomarker information and disease information is sent back to the central processing unit (CPU) of the portable biomarker analyzer electrophoresis apparatus for storage and use for continuing monitoring the evolution of the disease in the same patient during the time by consecutive testing of the same biomarkers, changes in the qualitative and quantitative profile of the biomarkers, appearance of new biomarkers, or modification of one or more biomarkers, or disappearance of one or more biomarkers, and the monitoring of the effectiveness of the treatment and wherein if the results of diagnosis and prognosis of a disease provided by the supercomputer and sent via the Internet to the family physician is correct and matching with the medical imaging information and/or the clinical diagnosis of the patient, then the fingerprint biomarker information and disease information is sent back to the central processing unit (CPU) of the portable biomarker analyzer electrophoresis apparatus for storage and use for matching with another set of identical biomarkers obtained from the sample specimen of a different patient.

16. The system of claim 1 wherein the panel of biomarkers determined by the evaluator are matched with disease-identifying biomarkers obtained from patient data sets being used as fingerprints of diagnosis and prognosis of diseases for increasing the accuracy, sensitivity and specificity of the disease, and providing a rapid and effective health screening technology and delivering the best treatment to a patient.

17. The system of claim 1 wherein the panel of biomarkers determined by the evaluator are constituents or biomolecules of a same group or category of proteomics or peptidomics, or a different group of genomics or transcriptomics, glycomics, lipidomics, and metabolomics, or a combination of one or more biomarkers belonging to different groups.

18. The system of claim 1 wherein the panel of biomarkers determined by the evaluator provide comprehensive information to identify a particular infectious microorganism including a virus, a bacteria and an individual body response to the infection by the microorganism including production of specific antibodies immunoglobulin M (IgM) and/or immunoglobulin G (IgG), an additional inflammatory response caused by the infectious microorganism including cytokines and/or chemokines, extra biomarkers causes by the infectious microorganism increases levels of collagens, collagen-derived peptides, prolyl hydroxylases, hydroxyproline-containing peptides, proline, hydroxyproline, lysyl oxidase, C-reactive protein, procalcitonin, tissue-type plasminogen activator, fibrin degradation product D-dimer, ferritin, and/or circulation cellular and exosome constituents when compared to a non-infected individual.

19. The system of claim 1 wherein the portable biomarker analyzer electrophoresis works in coordination and in sequential order to maximize the amount of biomarkers obtained from a patient monitored by a healthcare professional in a hospital setting, an ambulance, a doctor's office clinical setting, and at the patient's home to maximize the amount of biomarkers obtained from a patient monitored by a healthcare professional in a remote area using telemedicine to connect with a medical institution.

20. The system of claim 1 wherein the portable biomarker analyzer electrophoresis apparatus comprises at least two containers or vessels with caps providing hermetic and sealed protection, the at least two containers positioned at the inlet side of the separation passage or capillary, a first of the containers configured for receiving a separation buffer and a second of the containers configured for receiving an elution buffer or solution, with or without a chromophore, and each container having a tube inserted through a port into the container and serving as a guide for introducing an electrode through the tube, and as a conduit for introducing an inert gas to provide pressure for moving at least a plug of the fluid from the inside container into the separation passage or tubing.

21. The system of claim 1 wherein a urinary drainage collection bag is connected to the Foley catheter urine collection system, the Foley catheter urine collection system including a Foley catheter, a pumping system connected to the tubing connecting system or to an adaptor coupled to the Foley catheter prior to the urinary drainage collection bag or to an adaptor coupled to the Foley catheter after the urinary drainage collection bag.

\* \* \* \* \*